(12) United States Patent
Gaspard et al.

(10) Patent No.: US 12,097,231 B2
(45) Date of Patent: Sep. 24, 2024

(54) STEVIOL GLYCOSIDE COMPOSITIONS WITH REDUCED SURFACE TENSION

(71) Applicant: CARGILL, INCORPORATED, Wayzata, MN (US)

(72) Inventors: Dan S. Gaspard, Victoria, MN (US); Adam John Steinbach, Bloomington, MN (US); Adam T. Zarth, St. Louis Park, MN (US)

(73) Assignee: CARGILL, INCORPORATED, Wayzata, MN (US)

( * ) Notice: Subject to any disclaimer, the term of this patent is extended or adjusted under 35 U.S.C. 154(b) by 0 days.

(21) Appl. No.: 18/328,066

(22) Filed: Jun. 2, 2023

(65) Prior Publication Data

US 2024/0050506 A1 Feb. 15, 2024

Related U.S. Application Data

(63) Continuation of application No. 16/374,388, filed on Apr. 3, 2019, now Pat. No. 11,701,400, which is a continuation of application No. PCT/US2018/054804, filed on Oct. 8, 2018.

(60) Provisional application No. 62/676,722, filed on May 25, 2018, provisional application No. 62/569,279, filed on Oct. 6, 2017.

(51) Int. Cl.
| | |
|---|---|
| *A23L 27/30* | (2016.01) |
| *A23F 3/34* | (2006.01) |
| *A23L 2/56* | (2006.01) |
| *A23L 2/60* | (2006.01) |
| *A23L 2/68* | (2006.01) |
| *A23L 5/40* | (2016.01) |
| *A23L 27/00* | (2016.01) |
| *A61K 31/192* | (2006.01) |
| *A61K 31/235* | (2006.01) |
| *A61K 36/28* | (2006.01) |
| *B01D 15/36* | (2006.01) |
| *C07H 15/256* | (2006.01) |
| *C07K 1/16* | (2006.01) |
| *C07K 1/18* | (2006.01) |

(52) U.S. Cl.
CPC ............... *A61K 36/28* (2013.01); *A23F 3/34* (2013.01); *A23L 2/56* (2013.01); *A23L 2/60* (2013.01); *A23L 2/68* (2013.01); *A23L 5/40* (2016.08); *A23L 27/30* (2016.08); *A23L 27/36* (2016.08); *A23L 27/39* (2016.08); *A23L 27/88* (2016.08); *A61K 31/192* (2013.01); *A61K 31/235* (2013.01); *B01D 15/361* (2013.01); *C07H 15/256* (2013.01); *C07K 1/16* (2013.01); *C07K 1/18* (2013.01); *A23V 2002/00* (2013.01); *A23V 2200/15* (2013.01); *A23V 2250/258* (2013.01); *A61K 2236/31* (2013.01); *A61K 2236/39* (2013.01)

(58) Field of Classification Search
None
See application file for complete search history.

(56) References Cited

U.S. PATENT DOCUMENTS

| | | |
|---|---|---|
| 3,916,028 A | 10/1975 | Lee |
| 3,924,017 A | 12/1975 | Lee |
| 4,082,858 A | 4/1978 | Morita |
| 4,312,856 A | 1/1982 | Korduner |
| 4,495,170 A | 1/1985 | Beyts |
| 4,710,583 A | 12/1987 | Chmurny |
| 4,853,237 A | 8/1989 | Prinkkila |
| 4,906,480 A | 3/1990 | Kashket |
| 5,336,513 A | 8/1994 | Riemer |
| 5,681,569 A | 10/1997 | Kuznicki |
| 5,788,971 A | 8/1998 | Togasaki |
| 5,888,549 A | 3/1999 | Buchholz |
| 6,022,576 A | 2/2000 | Cirigliano |
| 6,337,095 B1 | 1/2002 | Jain |
| 6,426,112 B1 | 7/2002 | Boatright |
| 6,475,544 B1 | 11/2002 | Hiramoto |
| 6,589,588 B1 | 7/2003 | Wester |
| 6,635,774 B2 | 10/2003 | Roden |
| 6,900,240 B2 | 5/2005 | Empie |
| 6,989,171 B2 | 1/2006 | Portman |
| 7,279,184 B2 | 10/2007 | Gow |
| 7,291,352 B2 | 11/2007 | Gow |
| 7,294,353 B2 | 11/2007 | Gow |
| 7,651,717 B2 | 1/2010 | Shioya |
| 7,727,565 B2 | 6/2010 | Jani |
| 7,750,053 B2 | 7/2010 | Suzuki |
| 7,767,238 B2 | 8/2010 | Roy |

(Continued)

FOREIGN PATENT DOCUMENTS

| | | |
|---|---|---|
| CN | 1085073 A | 4/1994 |
| CN | 1100894 A | 4/1995 |

(Continued)

OTHER PUBLICATIONS

Messina D., et al. (2017) Maté tea and lipid profile in overweight women under caloric restriction. Ann Nutr. Metab. 71, 384 [abstract 144-1131]. DOI:10.1159/000480486.

(Continued)

*Primary Examiner* — Jyoti Chawla

(57) ABSTRACT

A steviol glycoside composition with reduced surface tension. The reduced surface tension steviol glycoside composition includes an aqueous solution of a steviol glycoside and a surface tension reducing compound in an amount effective to reduce surface tension. Method for reducing surface tension in a steviol glycoside solution includes contacting a steviol glycoside and a surface tension reducing compound.

23 Claims, 6 Drawing Sheets

(56) References Cited

U.S. PATENT DOCUMENTS

| | | |
|---|---|---|
| 7,838,044 B2 | 11/2010 | Abelyan |
| 7,879,376 B2 | 2/2011 | Boghani |
| 7,939,563 B2 | 5/2011 | Suzuki |
| 8,017,168 B2 | 9/2011 | Prakash |
| 8,076,491 B2 | 12/2011 | Karanewsky |
| 8,088,428 B2 | 1/2012 | Yamane |
| 8,092,795 B2 | 1/2012 | Tsuchiya |
| 8,178,148 B2 | 5/2012 | Fujii |
| 8,197,875 B2 | 6/2012 | Chien |
| 8,241,680 B2 | 8/2012 | Williams |
| 8,337,929 B2 | 12/2012 | Ogura |
| 8,367,137 B2 | 2/2013 | Prakash |
| 8,512,789 B2 | 8/2013 | Prakash |
| 8,524,304 B2 | 9/2013 | Prakash |
| 8,530,527 B2 | 9/2013 | Markosyan |
| 8,703,228 B2 | 4/2014 | Boghani |
| 8,940,350 B2 | 1/2015 | Prakash |
| 8,940,351 B2 | 1/2015 | Prakash |
| 8,956,678 B2 | 2/2015 | Prakash |
| 9,011,956 B2 | 4/2015 | Prakash |
| 9,060,537 B2 | 6/2015 | Mutilangi |
| 9,101,160 B2 | 8/2015 | Prakash |
| 9,101,161 B2 | 8/2015 | Prakash |
| 9,131,719 B2 | 9/2015 | Backes |
| 9,133,229 B2 | 9/2015 | Lee |
| 9,144,251 B2 | 9/2015 | Prakash |
| 9,149,051 B2 | 10/2015 | Prakash |
| 9,358,264 B2 | 6/2016 | Ibarra |
| 9,457,009 B2 | 10/2016 | Guthrie |
| 9,492,379 B2 | 11/2016 | Park |
| 9,510,611 B2 | 12/2016 | Purkayastha |
| 9,629,795 B2 | 4/2017 | Krammer |
| 9,636,373 B1 | 5/2017 | Akao |
| 9,775,822 B2 | 10/2017 | Prasad |
| 9,844,576 B2 | 12/2017 | Brownell |
| 9,848,624 B2 | 12/2017 | Ley |
| 9,889,107 B2 | 2/2018 | Guthrie |
| 9,962,356 B2 | 5/2018 | Prasad |
| 10,188,125 B2 | 1/2019 | Ozato |
| 10,376,521 B2 | 8/2019 | Zaworotko |
| 10,420,744 B2 | 9/2019 | Prasad |
| 10,602,758 B2 | 3/2020 | Dubois |
| 10,624,372 B2 | 4/2020 | Reichelt |
| 10,772,340 B2 | 9/2020 | Hotta |
| 10,780,170 B2 | 9/2020 | Purkayastha |
| 10,798,961 B2 | 10/2020 | Marcq |
| 10,849,339 B2 | 12/2020 | Prakash |
| 10,874,130 B2 | 12/2020 | Kim |
| 10,952,458 B2 | 3/2021 | Purkayastha |
| 10,973,794 B2 | 4/2021 | Forbes |
| 11,000,497 B2 | 5/2021 | Prasad |
| 2001/0051195 A1 | 12/2001 | Miljkovic |
| 2002/0068123 A1 | 6/2002 | Verhagen |
| 2002/0187239 A1 | 12/2002 | Miljkovic |
| 2002/0197386 A1 | 12/2002 | Hiramoto |
| 2003/0003212 A1 | 1/2003 | Chien |
| 2003/0008943 A1 | 1/2003 | Slone |
| 2003/0045473 A1 | 3/2003 | Sarama |
| 2003/0138537 A1 | 7/2003 | Bailey |
| 2003/0172392 A1 | 9/2003 | Mendu |
| 2004/0086619 A1 | 5/2004 | Zhong |
| 2004/0213881 A1 | 10/2004 | Chien |
| 2005/0079232 A1 | 4/2005 | Offord-Cavin |
| 2005/0106215 A1 | 5/2005 | Offord-Cavin |
| 2005/0118293 A1 | 6/2005 | Gow |
| 2005/0220868 A1 | 10/2005 | Lahl |
| 2006/0083838 A1 | 4/2006 | Jackson |
| 2006/0263475 A1 | 11/2006 | Jani |
| 2006/0280835 A1 | 12/2006 | Jani |
| 2006/0286202 A1 | 12/2006 | Boghani |
| 2007/0029258 A1 | 2/2007 | Takeda |
| 2007/0054023 A1 | 3/2007 | Bingley |
| 2007/0082106 A1 | 4/2007 | Lee |
| 2007/0116800 A1 | 5/2007 | Prakash |
| 2007/0116823 A1 | 5/2007 | Prakash |
| 2007/0116828 A1 | 5/2007 | Prakash |
| 2007/0116829 A1 | 5/2007 | Prakash |
| 2007/0116838 A1 | 5/2007 | Prakash |
| 2007/0116839 A1 | 5/2007 | Prakash |
| 2007/0128311 A1 | 6/2007 | Prakash |
| 2007/0292582 A1 | 12/2007 | Prakash |
| 2008/0014331 A1 | 1/2008 | Badalov |
| 2008/0063748 A1 | 3/2008 | Massey |
| 2008/0107787 A1 | 5/2008 | Prakash |
| 2008/0226788 A1 | 9/2008 | Chang |
| 2008/0226790 A1 | 9/2008 | Johnson |
| 2008/0261916 A1 | 10/2008 | Jaszberenyi |
| 2008/0286421 A1 | 11/2008 | DeLease |
| 2008/0292764 A1 | 11/2008 | Prakash |
| 2008/0292765 A1 | 11/2008 | Prakash |
| 2008/0292775 A1 | 11/2008 | Prakash |
| 2009/0004360 A1 | 1/2009 | Bingley |
| 2009/0053378 A1 | 2/2009 | Prakash |
| 2010/0028325 A1 | 2/2010 | Rocabayera Bonvila |
| 2010/0099857 A1 | 4/2010 | Evans |
| 2010/0112136 A1 | 5/2010 | Ward |
| 2010/0160224 A1 | 6/2010 | Thomas |
| 2010/0297327 A1 | 11/2010 | Stangle |
| 2010/0330244 A1 | 12/2010 | Nonaka |
| 2011/0033525 A1 | 2/2011 | Liu |
| 2011/0054022 A1 | 3/2011 | Poessel |
| 2011/0091394 A1 | 4/2011 | Abelyan |
| 2011/0104353 A1 | 5/2011 | Lee |
| 2011/0160311 A1 | 6/2011 | Prakash |
| 2011/0189360 A1 | 8/2011 | Yoo |
| 2011/0195161 A1 | 8/2011 | Upreti |
| 2011/0195170 A1 | 8/2011 | Shigemura |
| 2011/0293538 A1 | 12/2011 | Ley |
| 2012/0041078 A1 | 2/2012 | Tachdjian |
| 2012/0058236 A1 | 3/2012 | Fosdick |
| 2012/0064221 A1 | 3/2012 | Given |
| 2012/0076899 A1 | 3/2012 | Evans |
| 2012/0156351 A1 | 6/2012 | Miyazawa |
| 2012/0177602 A1 | 7/2012 | New |
| 2012/0196019 A1 | 8/2012 | Shi |
| 2012/0201935 A1 | 8/2012 | Krohn |
| 2013/0039932 A1 | 2/2013 | Park |
| 2013/0040036 A1 | 2/2013 | Zeller |
| 2013/0071521 A1 | 3/2013 | Lee |
| 2013/0209658 A1 | 8/2013 | Spelman |
| 2013/0251881 A1 | 9/2013 | Mutilangi |
| 2013/0274351 A1 | 10/2013 | Markosyan |
| 2013/0316066 A1 | 11/2013 | Brown |
| 2014/0004215 A1 | 1/2014 | Brownell |
| 2014/0094453 A1 | 4/2014 | Tachdjian |
| 2014/0155359 A1 | 6/2014 | Broze |
| 2014/0171519 A1 | 6/2014 | Prakash |
| 2014/0206634 A1 | 7/2014 | Liu |
| 2014/0295049 A1 | 10/2014 | Ragot |
| 2014/0302180 A1 | 10/2014 | Chapal |
| 2014/0309294 A1 | 10/2014 | Erfurt |
| 2014/0342078 A1 | 11/2014 | Hayes |
| 2015/0017284 A1 | 1/2015 | Prakash |
| 2015/0050410 A1 | 2/2015 | Luo |
| 2015/0125587 A1 | 5/2015 | Asano |
| 2015/0189904 A1 | 7/2015 | Prakash |
| 2015/0223510 A1 | 8/2015 | Lee |
| 2015/0289548 A1 | 10/2015 | Given |
| 2015/0320101 A1 | 11/2015 | Walton |
| 2015/0328179 A1 | 11/2015 | Nakashima |
| 2015/0344456 A1 | 12/2015 | Dull |
| 2015/0366253 A1 | 12/2015 | Shi |
| 2016/0100689 A1 | 4/2016 | Wang |
| 2016/0113316 A1 | 4/2016 | Nachbagauer |
| 2016/0165941 A1 | 6/2016 | Hofmekler |
| 2016/0183574 A1 | 6/2016 | Chen |
| 2016/0213039 A1 | 7/2016 | Kumar |
| 2016/0242452 A1 | 8/2016 | Mutilangi |
| 2016/0309761 A1 | 10/2016 | Brower, III |
| 2016/0316797 A1 | 11/2016 | Piorkowski |
| 2017/0006901 A1 | 1/2017 | Carlson |
| 2017/0055548 A1 | 3/2017 | Chakraborty |
| 2017/0095443 A1 | 4/2017 | Luo |
| 2017/0105432 A1 | 4/2017 | Karanewsky |

(56) References Cited

U.S. PATENT DOCUMENTS

| | | |
|---|---|---|
| 2017/0119032 A1 | 5/2017 | Patron |
| 2017/0119033 A1 | 5/2017 | Liu |
| 2017/0143012 A1 | 5/2017 | San Miguel |
| 2017/0156374 A1 | 6/2017 | Ackilli |
| 2017/0172191 A1 | 6/2017 | Prakash |
| 2017/0183326 A1 | 6/2017 | Kimoto |
| 2017/0273338 A1 | 9/2017 | Lee |
| 2017/0295827 A1 | 10/2017 | Prakash |
| 2017/0303574 A1 | 10/2017 | Luo |
| 2017/0354175 A1 | 12/2017 | Karanewsky |
| 2017/0362268 A1 | 12/2017 | Carlson |
| 2018/0000133 A1 | 1/2018 | Izumi |
| 2018/0002306 A1 | 1/2018 | Jiang |
| 2018/0086751 A1 | 3/2018 | Karanewsky |
| 2018/0092381 A1 | 4/2018 | Brijwani |
| 2018/0103670 A1 | 4/2018 | Recenti |
| 2018/0168212 A1 | 6/2018 | Markosyan |
| 2018/0177216 A1 | 6/2018 | Markosyan |
| 2018/0263269 A1 | 9/2018 | Prakash |
| 2018/0289042 A1 | 10/2018 | Bell |
| 2018/0296678 A1 | 10/2018 | Prakash |
| 2019/0116835 A1 | 4/2019 | Prakash |
| 2019/0142043 A1 | 5/2019 | Prakash |
| 2019/0175499 A1 | 6/2019 | Zhang |
| 2019/0274985 A1 | 9/2019 | Hotta |
| 2019/0313669 A1 | 10/2019 | Dubois |
| 2020/0009208 A1 | 1/2020 | Hwang |
| 2020/0023021 A1 | 1/2020 | Lewis |
| 2020/0054058 A1 | 2/2020 | Prakash |
| 2020/0085778 A1 | 3/2020 | Yamamoto |
| 2020/0138056 A1 | 5/2020 | Graz |
| 2020/0138765 A1 | 5/2020 | Prasad |
| 2020/0154737 A1 | 5/2020 | Dubois |
| 2020/0196649 A1 | 6/2020 | Mitchell |
| 2020/0197342 A1 | 6/2020 | Russo |
| 2020/0237845 A1 | 7/2020 | Suzuki |
| 2020/0275682 A1 | 9/2020 | Chakraborty |
| 2020/0305483 A1 | 10/2020 | Gan |
| 2020/0345049 A1 | 11/2020 | Galano |
| 2021/0037851 A1 | 2/2021 | Fraser |
| 2021/0051976 A1 | 2/2021 | Fraser |
| 2021/0084949 A1 | 3/2021 | Banavara |
| 2021/0092986 A1 | 4/2021 | Dubois |
| 2021/0128600 A1 | 5/2021 | Rauch |
| 2021/0153536 A1 | 5/2021 | Ozato |
| 2021/0236450 A1 | 8/2021 | Guthrie |
| 2021/0260013 A1 | 8/2021 | Lee |
| 2021/0267243 A1 | 9/2021 | Peterson |

FOREIGN PATENT DOCUMENTS

| | | |
|---|---|---|
| CN | 1144459 A | 3/1997 |
| CN | 1336333 A | 2/2002 |
| CN | 1615838 A | 5/2005 |
| CN | 1651398 A | 8/2005 |
| CN | 1253099 | 4/2006 |
| CN | 100341500 C | 10/2007 |
| CN | 102381974 A | 3/2012 |
| CN | 102771751 A | 11/2012 |
| CN | 102860438 A | 1/2013 |
| CN | 104397785 A | 3/2015 |
| CN | 102924544 B | 4/2015 |
| CN | 103656627 B | 9/2015 |
| CN | 103874411 A | 6/2016 |
| CN | 106138298 A | 11/2016 |
| CN | 107184482 A | 9/2017 |
| CN | 107455718 A | 12/2017 |
| DE | 29603759 U1 | 5/1996 |
| DE | 29808384 U1 | 8/1998 |
| EP | 0730830 A | 9/1996 |
| EP | 1186297 A2 | 3/2002 |
| EP | 1903890 A | 4/2008 |
| EP | 1716757 B1 | 7/2009 |
| EP | 1925208 B1 | 12/2011 |
| EP | 2340719 B1 | 2/2014 |
| EP | 2896301 B1 | 6/2016 |
| EP | 2643007 B1 | 8/2016 |
| EP | 3052074 A1 | 8/2016 |
| EP | 2625962 B1 | 6/2017 |
| EP | 3188604 A1 | 7/2017 |
| EP | 3257507 A1 | 12/2017 |
| EP | 3264919 A1 | 1/2018 |
| EP | 3097790 B1 | 5/2018 |
| EP | 2409696 B1 | 6/2018 |
| EP | 2753188 B1 | 1/2019 |
| EP | 2856883 B1 | 3/2019 |
| EP | 2692243 B1 | 6/2019 |
| EP | 3397072 B1 | 7/2019 |
| EP | 3513663 A1 | 7/2019 |
| EP | 3169166 B1 | 8/2019 |
| EP | 3524062 A2 | 8/2019 |
| EP | 2934181 B1 | 9/2019 |
| EP | 2124647 B2 | 12/2019 |
| EP | 3228195 B1 | 1/2020 |
| EP | 3544445 B1 | 5/2020 |
| FR | 2138067 B1 | 6/1976 |
| GB | 2348104 A | 5/1999 |
| JP | 54147976 A | 11/1979 |
| JP | 63173531 A | 7/1988 |
| JP | 0195739 A | 4/1989 |
| JP | 0427374 A | 1/1992 |
| JP | 04145048 A | 5/1992 |
| JP | 0638723 A | 2/1994 |
| JP | 07123921 A | 5/1995 |
| JP | 07135938 A | 5/1995 |
| JP | 0823939 A | 1/1996 |
| JP | 0994080 A | 4/1997 |
| JP | 09221667 A | 8/1997 |
| JP | 09266767 A | 10/1997 |
| JP | 10179079 A | 7/1998 |
| JP | 10183164 A | 7/1998 |
| JP | 10248501 A | 9/1998 |
| JP | 119189 A | 1/1999 |
| JP | 11299473 A | 11/1999 |
| JP | 2000063827 A | 2/2000 |
| JP | 2000308477 A | 11/2000 |
| JP | 2001321115 A | 11/2001 |
| JP | 2003204756 A | 7/2003 |
| JP | 2002021938 A1 | 1/2004 |
| JP | 2004528050 A | 9/2004 |
| JP | 2006006318 A | 1/2006 |
| JP | 2006104229 A | 4/2006 |
| JP | 2007143528 A | 6/2007 |
| JP | 2009517022 A | 4/2009 |
| JP | 2009523407 A | 6/2009 |
| JP | 2010521166 A | 6/2010 |
| JP | 2011045305 A | 3/2011 |
| JP | 2011168543 A | 9/2011 |
| JP | 2012005483 A | 1/2012 |
| JP | 2012110322 A | 6/2012 |
| JP | 2012240949 A | 12/2012 |
| JP | 20110711791 A | 4/2013 |
| JP | 2015506718 A | 3/2015 |
| JP | 2015511498 A | 4/2015 |
| JP | 2017121221 A | 7/2017 |
| JP | 2017123788 A | 7/2017 |
| JP | 20160848871 A | 9/2017 |
| JP | 2018085964 A | 6/2018 |
| JP | 6710115 B2 | 6/2020 |
| JP | 2019230013 A | 6/2020 |
| KR | 101500485 B1 | 3/2015 |
| PH | 12011000255 A | 7/2011 |
| WO | 1998042209 A1 | 10/1998 |
| WO | 1999030576 W | 6/1999 |
| WO | 2000030464 A1 | 6/2000 |
| WO | 2000062628 A1 | 10/2000 |
| WO | 2000069282 A1 | 11/2000 |
| WO | 2001097624 A1 | 12/2001 |
| WO | 2002041700 A1 | 5/2002 |
| WO | 02100192 W | 12/2002 |
| WO | 2002096852 A1 | 12/2002 |
| WO | 2007013616 A1 | 2/2007 |
| WO | 2007061753 A2 | 5/2007 |
| WO | 2007061795 A1 | 5/2007 |

(56) References Cited

FOREIGN PATENT DOCUMENTS

| | | |
|---|---|---|
| WO | 2007149672 A2 | 12/2007 |
| WO | 2008057965 A2 | 5/2008 |
| WO | 2008093892 A1 | 8/2008 |
| WO | 2008147723 A1 | 12/2008 |
| WO | 2008147725 A1 | 12/2008 |
| WO | 2009012051 A1 | 1/2009 |
| WO | 2010038911 A1 | 4/2010 |
| WO | 11094423 W | 8/2011 |
| WO | 2011094423 A1 | 8/2011 |
| WO | 2011105561 A1 | 9/2011 |
| WO | 2011106114 A1 | 9/2011 |
| WO | 2011112892 A1 | 9/2011 |
| WO | 2012083251 A1 | 6/2012 |
| WO | 2012107205 A1 | 8/2012 |
| WO | 2012109506 A1 | 8/2012 |
| WO | 2012166164 A1 | 12/2012 |
| WO | 2013096420 W | 6/2013 |
| WO | 2013148177 A1 | 10/2013 |
| WO | 2014104408 A1 | 7/2014 |
| WO | 2014146135 A2 | 9/2014 |
| WO | 2014153000 A1 | 9/2014 |
| WO | 2015023928 A1 | 2/2015 |
| WO | 2015024218 A1 | 2/2015 |
| WO | 2015117011 A1 | 8/2015 |
| WO | 2016036578 A1 | 3/2016 |
| WO | 2016049236 A1 | 3/2016 |
| WO | 2016073251 A1 | 5/2016 |
| WO | 16085919 W | 6/2016 |
| WO | 16085924 W | 6/2016 |
| WO | 16086233 W | 6/2016 |
| WO | 2016100689 A1 | 6/2016 |
| WO | 17053980 W | 3/2017 |
| WO | 2017059414 A1 | 4/2017 |
| WO | 2017095932 A1 | 6/2017 |
| WO | 17120480 W | 7/2017 |
| WO | 17189994 W | 11/2017 |
| WO | 2017196933 A1 | 11/2017 |
| WO | 2018013739 A2 | 1/2018 |
| WO | 2018102447 A2 | 6/2018 |
| WO | 2019071182 A1 | 4/2019 |
| WO | 2019071187 A1 | 4/2019 |
| WO | 2019071188 A1 | 4/2019 |
| WO | 2019071220 A1 | 4/2019 |
| WO | 2019071254 A1 | 4/2019 |
| WO | 19177634 W | 9/2019 |
| WO | 2019177634 A1 | 9/2019 |
| WO | 19222601 W | 11/2019 |
| WO | 2020172276 W | 8/2020 |
| WO | 2020202193 W | 10/2020 |
| WO | 2020237060 A1 | 11/2020 |
| WO | 2021038830 W | 3/2021 |
| WO | 2021038832 W | 3/2021 |
| WO | 2021049864 W | 3/2021 |
| WO | 2021081417 A1 | 4/2021 |
| WO | 2021090989 A1 | 5/2021 |
| WO | 2021091322 A1 | 5/2021 |
| WO | 2021091327 A1 | 5/2021 |
| WO | 2021125070 A1 | 6/2021 |
| WO | 2021132439 W | 7/2021 |

OTHER PUBLICATIONS

Mikulasova M., et al. (2005) Genotoxic effects of the hydroxycinnamic acid derivatives—caffeic, chlorogenic and cichoric acids. Biologia (Bratisl.) 60, 275-279.

Minuzzi Becker A., et al. (2019) Spray-dried yerba mate extract capsules: clinical evaluation and antioxidant potential in healthy individuals. Plant oods Hum. Nutr. 74, 495-500 [plus supplementary tables]. DOI:10.1007/s11130-019-00764-4.

Miranda D. D. C., et al. (2008) Protective effects of mate tea (*Ilex paraguariensis*) on H2O2-induced DNA damage and DNA repair in mice. Mutagenesis 23, 261-265. DOI:10.1093/mutage/gen011.

Miura et al., "Molecularly imprinted polymer for chlorogenic acid by modified precipitation polymerization and its application to extraction of chlorogenic acid from Eucommia ulmodies leaves," Journal of Pharmaceutical and Biomedical Analysis, 114 (2015) 139-144.

Moeenfard, et al., "Quantification of Caffeoylquinic Acids in Coffee Brews by HPLC-DAD," Journal of Analytical Methods in Chemistry, Dec. 21, 2014.

Monteiro M., et al. (2007) Chlorogenic acid compounds from coffee are differentially absorbed and metabolized in humans. J. Nutr. 137, 2196-2201. DOI:10.1093/jn/137.10.2196.

Moura de Oliveira D., et al. (2017) Bioavailability of chlorogenic acids in rats after acute ingestion of maté tea (*Ilex paraguariensis*) or 5-caffeoylquinic acid. Eur. J Nutr. 56, 2541-2556. DOI:10.1007/s00394-016-1290-1.

Murdande, et al., "Aqueous solubility of crytalline and amorphous drugs: challenges in measurement," Pharmaceutical Development and Technology, 2011.

Murdande, et al., "Solubility Advantage of amorphous pharmaceuticals: I. A thremodynamic analysis," Wiley InterScience, 2009.

Murshedkav, Tooba, "Effect of crystalline to amorphous coversion on solubility of cefuroxime axetil," Univeristy of Rhode Island, 2002.

Naimi, et al., "Rosemary Extract as a Potential Anti-Hyperglycemic Agent: Current Evidence and Future Perspectives", Sep. 1, 2017, Nutrients; vol. 9, Issue 9, pp. 1-19.

Nakamura S., et al. (2006) [Pharmacokinetics of chlorogenic acids absorbed in human plasma and their metabolites following oral ingestion of coffee drink]. Yakuri to Chiryo [Jpn. Pharmacol. Ther.] 34, 1239-1246.

Nalte, YK, et al., Solubility Enhancement of Nevirapine by Cocrystallisation Technique. Journal of Pharmacy Research. Aug. 21, 2015, vol. 9, No. 8; pp. 556-561. ISSN:0974-6943.

Naylor L. H., et al. (2021) Acute dose-response effect of coffee-derived chlorogenic acids on the human vasculature in healthy volunteers: a randomized controlled trial. Am. J. Clin. Nutr. 113, 370-379. DOI:10.1093/ajcn/nqaa312.

Nguyen et al., "Facile preparation of water soluble curcuminoids extracted from turmeric (*Curcuma longa* L.) power by using steviol glucosides," Food Chemistry, 2017, 214, 366-373.

Nicoud, et al., "Estimation of the solubility of metastable polymorphs: A critical review," Cryst. Growth Des., 2018.

Notice of Opposition in EP2934181.

Nowacki L. C., et al. (2021) Ilex paraguariensis extract as an alternative to pain medications. Acta Pharm. 71, 383-398. DOI:10.2478/acph-2021-0029.

Ochiai R., et al. (2019) Effect of chlorogenic acids on cognitive function in mild cognitive impairment: a randomized controlled crossover trial. J. Alzheimers Dis. 72, 1209-1216 [plus supplementary tables]. DOI:10.3233/jad-190757.

Ohta et al., "Characterization of Novel Steviol Glycosides from Leaves of Stevia rebaudiana Morita," 2010, J. Appl. Glycosci., 57, 199-209.

Olthof M. R., et al. (2001a) Consumption of high doses of chlorogenic acid, present in coffee, or of black tea increases plasma total homocysteine concentrations in humans. Am. J. Clin. Nutr. 73, 532-538. DOI:10.1093/ajcn/73.3.532.

Olthof M. R., et al. (2001b) Chlorogenic acid and caffeic acid are absorbed in humans. J. Nutr. 131, 66-71. DOI:10.1093/jn/131.1.66.

Olthof M. R., et al. (2003) Chlorogenic acid, quercetin-3-rutinoside and black tea phenols are extensively metabolized in humans. J. Nutr. 133, 1806-1814 [erratum, 133, 2692]. DOI:10.1093/jn/133.6.1806.

Onakpoya I. J., et al. (2015) The effect of chlorogenic acid on blood pressure: a systematic review and meta-analysis of randomized clinical trials. J. Hum. Hypertens. 29, 77-81 [plus supplementary data]. DOI:10.1038/ihh.2014.46.

Park I., et al. (2017) Effects of subacute ingestion of chlorogenic acids on sleep architecture and energy metabolism through activity of the autonomic nervous system: a randomised, placebo-controlled, double-blinded cross-over trial. Br. J. Nutr. 117, 979-984. DOI:10.1017/S0007114517000587.

Pereira Panza V., et al. (2019) Effect of mate tea (*Ilex paraguariensis*) on the expression of the leukocyte NADPH oxidase subunit p47phox

(56) References Cited

OTHER PUBLICATIONS and on circulating inflammatory cytokines in healthy men: a pilot study. Int. J. Food Sci. Nutr. 70, 212-221DOI:10.1080/09637486. 2018.1486393.
Phenolaeis.com Accessed Aug. 24, 2022 Palm Fruit Extract compositions and applications.
Phenolaeis.com Accessed Sep. 9, 2020 Palm Fruit Bioactives Complex.
Pimpley et al. "The chemistry of chlorogenic acid from green coffee and its role in attenuation of obesity and diabetes" at https://pubmed.ncbi.nlm.nih.gov/32633686. (Year: 2020).
Plumb G. W., et al. (1999) Metabolism of chlorogenic acid by human plasma, liver, intestine and gut microflora. J. Sci. Food Agric. 79, 390-392. DOI:10.1002/(SICI)1097-0010(19990301)79:3<390::AID-JSFA258>3.0.CO;2-0.
Prakash et al., "Catalytic Hydrogenation of the Sweet Principles of Stevia rebaudiana, Rebaudioside B, Rebaudioside C, and Rebaudioside D and Sensory Evaluation of Their Reduced Derivatives", Int. J. Mol. Sci. 2012, 13, 15126-15136; doi:10.3390/ijms131115126.
Prakash Indra et al: "Synthesis and Sensory Evaluation of ent-Kaurane Diterpene Glycosides", Molecules, [Online] vol. 17, No. 8, Jan. 1, 2012 (Jan. 1, 2012), pp. 8908-8916, XP055839039, DOI: 10.3390/molecules17088908 Retrieved from the Internet: URL:https://www.ncbi.nlm.nih.gov/pmc/artic les/PMC6268950/pdf/molecules-17-08908.pdf> [retrieved on Aug. 5, 2021].
Prakash, "Characterization and sensory evaluation of a hexa B-D-glucopyranosyl diterpene from Stevia rebaudiana," Natural Products Communications, 2013, 8:1523-1526.
Prakash, et al., "Development of novel functional confectionery using low reduced sugar," Indian Journal of Drugs, 2016, 4(4), 141-148.
Renouf M., et al. (2014) Dose-response plasma appearance of coffee chlorogenic and phenolic acids in adults. Mol. Nutr. Food Res. 58, 301-309. DOI:10.1002/mnfr.201300349.
Richling E., et al. (2012) Dose-response relationship of chlorogenic acids in humans. Naunyn Schmiedebergs ArchPharmacol. 385, S75 [abstract 327]. DOI:10.1007/s00210-012-0736-0.
Rocha D. S., et al. (2018) Effect of yerba mate (*Ilex paraguariensis*) extract on the metabolism of diabetic rats. Biomed. Pharmacother. 105, 370-376 [plus supplementary figure]. DOI:10.1016/j.biopha. 2018.05.132.
Rogerio De Sousa W., et al. (2019) Evaluation of reproductive toxicology of aqueous extract of yerba mate (*Ilex paraguariensis* A. St.-Hil.), a traditional South American beverage. J. Med. Food 22, 97-101. DOI:10.1089/imf.2018.0060.
Rogers et al., "Changes to the content of sugars, sugar alcohols, myo-inositol, carboxylic acids and inorganic anions in developing grains from different varieties of Robusta (*Coffea canephora*) and Arabica (*C. arabica*) coffees," Plant Science, 1999, 149, 115-123.
Roy, G., "Bitterness: reduction and inhibition," Trends Food Sci Tech, 1992, 3, 85-91.
Sanchez Boado L., et al (2018) Effects of Ilex paraguariensis polyphenols on magnesium absortion and iron bioavailability: preliminary study. J. Food Res. 7, 114-126. DOI:10.5539/jfr.v7n2p114.
Sarria B., et al. (2020a) Yerba mate may prevent diabetes according to a crossover, randomized, controlled study in humans. Proc. Nutr. Soc. 79, OCE2, E245 DOI:10.1017/S0029665120001937.
Sarria B., et al. (2020b) Yerba mate improves cardiovascular health in normocholesterolemic and hypercholesterolemic subjects. Proc. Nutr. Soc. 79, OCE2, E635. DOI: 10.1017/S0029665120005844.
Schwarz et al., "Investigation of plant extracts for the protection of processed foods against lipid oxidation." Eur Food Res Technol, 2001, 212:319-328.
Shibata et al., "Glucosylation of steviol and steviol-glucosides in extracts from Stevia rebaudiana Bertoni," Plant Physiol., 1991, 95, 152-156.
Shinomiya K., et al. (2004) Effects of chlorogenic acid and its metabolites on the sleep-wakefulness cycle in rats. Eur. J. Pharmacol. 504, 185-189. DOI:10.1016/j.ejphar.2004.09.054.
Shiraishi et al., "Taste-Masking Effect of Chlorogenic Acid (CGA) on Bitter Drugs Evaluated by Taste Sensor and Surface Plasmon Resonance on the Basis of CGA-Drug Interactions," 2017, 65(2):127-133, Chem Pharm Bull (Tokyo).
Simao Do Carmo L., et al. (2013) The effects of yerba mate (*Ilex paraguariensis*) consumption on IL-1, IL-6, TNF-α and IL-10 production by bone marrow cells in Wistar rats fed a high-fat diet. Int J Vitam Nutr Res 83, 26-35. DOI:10.1024/0300-9831/a000142.
Sirima Puangpraphant et al: "Dicaffeoylquinic acids in Verba mate (*Ilex paraguariensis* St. Hilaire) inhibit NF-&kgr;B nucleus translocation in macrophages and induce apoptosis by activating caspases-8 and -3 in human colon cancer cells", Molecular Nutrition & Food Research, vol. 55, No. 10, Oct. 8, 2011 (Oct. 8, 2011), pp. 1509-1522, XP055175515, ISSN: 1613-4125, DOI: 10.1002/mnfr. 201100128.
Freedman S. O., et al. (1961) Chlorogenic acid: an allergen in green coffee bean. Nature 192, 241-243. DOI:10.1038/192241a0.
Freedman S. O., et al. (1964) Antigenic and allergenic properties of chlorogenic acid man, rabbit, guinea pig. Can. Med. Assoc. J. 90, 473-474.
Fu et al., "Production of chlorogenic acid and its derivatives in hairy root cultures of Stevia rebaudiana," Jan. 14, 2015, Journal of Agriculatural and Food Chemistry, 63(1):262-268.
Gawel-Beben et al., "Stevia rebuadiana Bert. Leaf extracts as a multifunctional source of natural antioxidants," Molecules, Mar. 27, 2015.
Gebara K. S., et al. (2020) A randomized crossover intervention study on the effect a standardized maté extract (*Ilex paraguariensis* A. St.-Hil.) in Men predisposed to cardiovascular risk. Nutrients, 13, 14 [14pp]. DOI:10.3390/nu13010014.
Giordani, Antonio, "The amorphous form in drug development," Crystal Forms, 2012.
Gómez-Juaristi M., Martínez-López S., Sarria B., Bravo L. and Mateos R. (2018) Absorption and metabolism of yerba mate phenolic compounds in humans. Food Chem. 240, 1028-1038. DOI:10. 1016/j.foodchem.2017.08.003.
Gonthier M.-P., et al. (2006) Microbial metabolism of caffeic acid and its esters chlorogenic and caftaric acids by human faecal microbiota in vitro. Biomed. Pharmacother. 60, 536-540. DOI:10. 1016/j.biopha.2006.07.084.
Grzesiuk J. D., et al (2012) Evaluation of mutagenicity and antimutagenicity of Ilex paraguariensi} A. St.-Hil.: Aquifoliaceae infusion on Allium cepa assay. Arq. Cienc. Saude UNIPAR 16, 73-78. DOI:10.25110/arqsaude.v16i2.2012.4840.
Gu R., et al. (2007) Simultaneous determination of 1,5-dicaffeoylquinic acid and its active metabolites in human plasma by liquid chromatography-tandem mass spectrometry for pharmacokinetic studies. J. Chromatogr. B. 852, 85-91. DOI:10.1016/j.jchromb.2006. 12.055.
Hancock, B. C., et al. "What is the true solubility advantage for amorphous pharmaceuticals?," Pharm Res, 17:397-404, 2000.
Hernandes L. C., et al. (2016) Cytotoxicity and genotoxicity of chlorogenic acid alone or associated with the demethylating drug 5-azacytidine in Jurkat cells. Toxicol. Lett. 258, Suppl. S, S56 [abstract OSC01-007]. DOI:10.1016/i.toxlet.2016.06.1295.
Hernandez T et al., "Variations in the phenolic composition of fruit juices with different treatments," European Food Research and Technology, vol. 204, No. 2, 1997, p. 151-155.
Hildebrand, Joel, "Theory of solubility," Physical Review, 1923.
IARC (1991) Mate. In Coffee, Tea, Mate, Methylxanthines and Methylglyoxal. IARC Working Group, Feb. 27-Mar. 6, 1990, Lyon. IARC Monographs on the Evaluation of Carcinogenic Risks to Humans, vol. 51, pp. 273-287. World Health Organization (WHO), International Agency for Research on Cancer (IARC).
IARC (2018) Drinking mate and very hot beverages. In Drinking Coffee, Mate, and Very Hot Beverages. Expert Opinions of IARC Working Group on the Evaluation of Carcinogenic Risks to Humans, May 24-31, 2016, Lyon, France. IARC Monographs on the Evaluation of Carcinogenic Risks to Humans, vol. 116, pp. 427-496. Lyon, France: International Agency for Research on Cancer (IARC), Lyon, France.
Islam, et al., "Particle crystallization during spray drying in humid air," Journal of Food Engineering, 2010.

(56) References Cited

OTHER PUBLICATIONS

Jeon et al., "Contents of chlorogenic acids and caffeine in various coffee-related products," Journal of Advanced Research, 17 (2019), 85-94.
Jin S., et al. (2015) Chlorogenic acid improves late diabetes through adiponectin receptor signaling pathways in db/db mice. PLoS One 10, e0120842 [15pp]. DOI:10.1371/journal.pone.0120842.
Journal of the Brewing Society of Japan, 1959, vol. 54, No. 4, pp. 239-242.
Julia Y.Q. Low et al, "Psychophysical Evaluation of Sweetness Functions Across Multiple Sweeteners", Chemical Senses.,vol. 42, No. 2, Oct. 20, 2016 (Oct. 20, 2016), p. 111-120.
Kato M., et al. (2018) Effect of chlorogenic acid intake on cognitive function in the elderly: a pilot study. Evid. Based. Complement. Alternat. Med. 2018, Article ID 8608497 [8pp]. DOI:10.1155/2018/8608497.
Kellie P Burris et al, "Composition and Bioactive Properties of Yerba Mate (Ilex paraguariensis A. St.-Hil.): A Review", Chillán Jun. 2012 (Jun. 2012), p. 268-275.
Kim H. J., et al. (2012) Effect of green mate in overweight volunteers: a randomised placebo-controlled human study. J. Funct. Foods 4, 287-293. DOI:10.1016/j.jff.2011.12.005.
Kim S.-Y., et al. (2015) Anti-obesity effects of Yerba Mate (Ilex paraguariensis): a randomized, double-blind, placebo-controlled clinical trial. BMC Complement. Altern. Med. 15, 338 [8pp]. DOI:10.1186/s12906-015-0859-1.
Klein G. A., et al (2011) Mate tea (Ilex paraguariensis) improves glycemic and lipid profiles of type 2 diabetes and pre-diabetes individuals: a pilot study. J. Am. Coll. Nutr. 30, 320-332.
Kremr et al., "Unremitting Problems with Chlorogenic Acid Nomenclature: A Review," Quim. Nova, vol. 39, No. 4, 530-533, 2016.
Kren, V., et al., "Glycosides in Medicine: The Role of Glycosidic Residue in Biological Activity", Current Medicinal Chemistry, 2001, 8, 1313-1338.
Kroyer, G., "Stevioside and Stevia-sweetener in food: application, stability and interaction with food ingredients," J. Verbr. Lebensm., 2010, 5:225-229.
Kujawska M (2018) Yerba mate (Ilex paraguariensis) beverage: nutraceutical ingredient or conveyor for the intake of medicinal plants? Evidence from Paraguayan folk medicine. Evid. Based. Complement. Alternat. Med. 2018, Article ID 6849317 [17pp]. DOI:10.1155/2018/6849317.
Ky et al., "Camparison of Five Purification Methods for Chlorogenic Acids in Green Coffee Beans (Coffea sp.)," J. Agric. Food Chem. 1997, 45, 786-790, obtained from https://horizon.documentation.ird.fr/exl-doc/pleins_textes/pleins_textes_6/b_fdi_47-48/010010457.pdf.
Laird Layton L., et al. (1964) Pure chlorogenic acid is not allergenic in atopy to green coffee: A specific protein probably is involved. Nature 203, 188-189. DOI:10.1038/203188a0.
Lee et al., "Chicoric acid: chemistry distribution, and production," Frontiers in Chemistry, 2013, 1(40).
Leitão A. C. and Braga R. S. (1994) Mutagenic and genotoxic effects of mate (Ilex paraguariensis) in prokaryotic organisms. Braz. J. Med. Biol. Res. 27, 1517-1525.
Lin M., et al. (2013) Evaluation of the potential sensitization of chlorogenic Acid: a meta-analysis. Evid. Based. Complement. Alternat. Med. 2013, Article ID 208467 DOI:10.1155/2013/208467.
Liquid Stevia and Liquid Stevia (flavored) from Stevita Co., 2012.
Liu B., et al. (2017) Preparation, phytochemical investigation, and safety evaluation of chlorogenic acid products from Eupatorium adenophorum. Molecules 22, 67 [12pp]. DOI:10.3390/molecules22010067.
Liu Na, et al., "Review on Stevia rebaudiana research abroad in 2015", Sugar Crops of China. 2017, 39(1): 57-64.
Liu Z., et al. (2010) Evaluation of the immunosensitizing potential of chlorogenic acid using a popliteal lymph node assay in BALB/c mice. Food Chem. Toxicol. 48, 1059-1065. DOI:10.1016/j.fct.2010.01.024.

Lorena Deladino et al: "Major Phenolics in Yerba Mate Extracts (Ilex paraguariensis) and Their Contribution to the Total Antioxidant Capacity", Food and Nutrition Sciences, vol. 04, Aug. 1, 2013 (Aug. 1, 2013), pp. 154-162, XP055588480, ISSN: 2157-944X, DOI: 10.4236/fns.2013.48A019.
Lowell F. C. (1965) Allergenicity of chlorogenic acid. J. Allergy 36, 308. DOI:10.1016/0021-8707(65)90091-2.
Maietta et al., "Artichoke (Cynara cardunculus L. var. scolymus) waste as a natural source of carbonyl trapping and antiglycative agents," Food Research International, 100 (2017) 780-790.
Marques V. X. and Farah A. (2010) Urinary excretion of chlorogenic acids and metabolites in humans after green mate (I. paraguariensis) consumption. FASEB J. 24, 1, Suppl., [abstract 922.1]. DOI:10.1096/fasebj.24.1_supplement.922.1.
Masuda, et al., "Powder Technology Handbook," Taylor & Francis, 2006.
Matsumoto R. L. T., et al. (2009) Effects of maté tea (Ilex paraguariensis) ingestion on mRNA expression of antioxidant enzymes, lipid peroxidation, and total antioxidant status in healthy young women. J. Agric. Food Chem. 57, 1775-1780. DOI:10.1021/jf803096g.
Meilgaard MC, Civille GV, and Carr BT (2007). Sensory Evaluations Techniques, CRC Press, Boca Raton, FL.
Meinhart et al., "Analysis of chlorogenic acids isomers and caffeic acid in 89 herbal infusions (tea)," Journal of Food Composition and Analysis, 73 (2018) 76-82.
Meinhart et al., "Chlorogenic acid isomer contents in 100 plants commercialized in Brazil," Food Research International, 99 (2017) 522-530.
Meireles et al., "Stevia (Stevia rebaudiana bertoni):—Futuristic view of the sweeter side of life," Floriculture, Ornamental and Plant Biotechnology vol. IV, 2006, Global Science Books.
Mello F. W., et al. (2018) Maté consumption association with upper aerodigestive tract cancers: a systematic review and meta-analysis. Oral Oncol. 82, 37-47 [plus supplementary data]. DOI:10.1016/j.oraloncology.2018.04.023.
Song Z., et al. (2014) [Effect of chlorogenic acid at high dose on expression of hepatic inflammatory cytokines mRNA induced by lipopolysaccharides]. Ying Yang Xue Bao [Acta Nutr. Sin.] 36, 481-485.
Song, "Lenalidomide-Gallic Acid Cocrystals with Constant High Solubility", Crystal Growth & Design, 2015, 15, pp. 4869-4875.
Souza S. J., et al. (2017) Effect of chocolate and mate tea on the lipid profile of individuals with HIV/AIDS on antiretroviral therapy: A clinical trial. Nutrition 43-44, 61-68. DOI:10.1016/j.nut.2017.06.017.
Stalmach A., et al. (2009) Metabolite profiling of hydroxycinnamate derivatives in plasma and urine after the ingestion of coffee by humans: identification of biomarkers of coffee consumption. Drug Metab. Dispos. 37, 1749-1758. DOI:10.1124/dmd.109.028019.
Stalmach A., et al. (2010) Bioavailability of chlorogenic acids following acute ingestion of coffee by humans with an ileostomy. Arch. Biochem. Biophys. 501, 98-105. DOI:10.1016/j.abb.2010.03.005.
Standard Method Performance Requirements (SMPRs) for Determination of Phenolic Compounds in Dietary Supplements and Dietary Ingredients Containing Echinacea, Sep. 22, 2017, AOAC International.
Stich H. F., et al. (1981) A comparative genotoxicity study of chlorogenic acid (3-O-caffeoylquinic acid). Mutat. Res. 90, 201-212. DOI:10.1016/0165-1218(81)90001-X.
Stukelj, et al., "Direct measurement of amorphous solubility," Analytical Chemistry, 2019.
Suarez-Quiroz et al., "Isolation of green coffee chlorogenic acids using activated carbon," Journal of Food Composition and Analysis, 2014, 33:55-58.
Sunup® Commercially available stevia sweetened green coffee bean beverage, purchased Jun. 2018.
Suzuki A., et al. (2006) Chlorogenic acid attenuates hypertension and improves endothelial function in spontaneously hypertensive rats. J. Hypertens. 24, 1065-1073. DOI:10.1097/01.hjh.0000226196.67052.c0.
Sweet Drops™ Liquid Stevia Product, 2012.

(56) References Cited

OTHER PUBLICATIONS

Tanaka, O., "Improvement of taste of natural sweeteners," Pure & Appl. Chem., 69(4):975-683, 1997.
Trugo et al., Chlorogenic Acid Composition of Instant Coffees, Analyst, Mar. 1984, vol. 109, pp. 263-266.
Tyrer, D., "The theory of solubility," The Journal of Physical Chemistry, 1912.
U.S. FDA (1993) Appendix I. Table 14. Conversion table for test chemical treatment doses used in PAFA. In Priority Based Assessment of Food Additives (PAFA) Database. U.S. Food and Drug Administration (U.S. FDA), Center for Food Safety & Applied Nutrition (CFSAN), Washington, DC, p. 58.
U.S. FDA (2018) Part 182—Substances generally recognized as safe. Section §182.20—Essential oils, oleoresins (solvent-free), and natural extractives (including distillates). In: U.S. Code of Federal Regulations (CFR). Title 21: Food and Drugs. (U.S. Food and Drug Administration). U.S. Government Printing Office (GPO), Washington, DC.
Upreti, Mani et al., "Solubility Enhancement of Steviol Glycosides and Characterization of Their Inclusion Complexes with Gamma-Cyclodextrin", Int. J. Mol. Sci. 2011, 12, 7529-7553.
Vargas Alves R. J., et al. (2008) The evaluation of maté (*Ilex paraguariensis*) genetic toxicity in human lymphocytes by the cytokinesis-block in the micronucleus assay. Toxicol. In Vitro 22, 695-698. DOI:10.1016/j.tiv.2007.11.005.
Wang Shaojia, et al., "Progress of functional components in Stevia rebaudiand Bertoni", Science and Technology of Food Industry. 2017, vol. 38, No. 20.
Wang Y., et al. (2018) [Effects of chlorogenic acid on growth performance, serum immunoglobulins, intestinal mucosa morphology, digestive and absorptive capacity of piglets]. Chin. J. Anim. Nutr. 30, 1136-1145 [DOI:10.7506/spkx1002-6630-201709026.
Wantanabe T., et al. (2019) Coffee abundant in chlorogenic acids reduces abdominal fat in overweight adults: a randomized, double-blind, controlled trial. Nutrients 11, 1617 [13pp]. DOI:10.3390/nu11071617.
Wei Z.-M., et al. (2010) [Clinical tolerability of 1,5-dicaffeoylquinic acid tablets]. Zhongguo Xin Yao Za Zhi [Chin. J. New Drugs] 19, 106-108.
Weidel et al., "A Rapid Method for Quantifying Chlorogenic Acid Levels in Potato Samples," Journal of AOAC International, vol. 97, No. 3, Nov. 3, 2014.
Whole Foods 365 Stevia Extract Liquid, 2012.
Wildermuth et al., "Chlorogenic acid oxidation and its reaction with sunflower proteins to form green-colored complexes," Comprehensive Reviews in Food Science and Food Safety, 2016, vol. 15, 829-843.
Wnuk M., et al. (2009) Evaluation of the cyto- and genotoxic activity of yerba mate (*Ilex paraguariensis*) in human lymphocytes in vitro. Mutat. Res. 679, 18-23. DOI:10.1016/j.mrgentox.2009.07.017.
Written Opinion of WO 2012/082587, Jun. 13, 2013.
Yang B., et al. (2005) Metabolic profile of 1,5-dicaffeoylquinic acid in rats, an in vivo and in vitro study. Drug Metab. Dispos. 33, 930-936. DOI:10.1124/dmd.104.002154.
Yara Queiroz et al: The Chlorogenic Acid and Caffeine Content of Verba Mate (*Ilex paraguariensis*) Beverages11, Jan. 1, 2005 (Jan. 1, 2005), pp. 91-95, XP055715126, Retrieved from the Internet: URL:https://media.enfasis.com/adjuntos/146 /documentos/000/134/0000134821.pdf [retrieved on Jul. 15, 2020].
Yu S., et al. (2015) Yerba mate (*Ilex paraguariensis*) improves microcirculation of volunteers with high blood viscosity: a randomized, double-blind, placebo-controlled trial. Exp. Gerontol. 62, 14-22 [plus supplementary tables]. DOI:10.1016/j.exger.2014.12.016.
Zhu Y., et al. (2017) [Effect of caffeine and chlorogenic acid on body weight, lipid accumulation and the expression of lipid metabolism-related genes in high-fat diet-fed mice]. Shipin Kexue [Food Sci.] 38, 162-167 DOI:10.7506/spkx1002-6630-201709026.
Zuniga L. Y., et al. (2018) Effect of chlorogenic acid administration on glycemic control, insulin secretion, and insulin sensitivity in patients with impaired glucose tolerance. J. Med. Food 21, 469-473. DOI:10.1089/jmf.2017.0110.
Abeywardena M. Y., et al. (2010) Acute administration of chlorogenic acid reduces blood pressure in the rat. Hypertension 55, 1493 [abstract 002]. DOI:10.1161/HYP.0b013e3181df4279.
Albas C. S., et al (2014) Avaliação da genotoxicidade da *Ilex paraguariensis* (erva mate) pelo teste do micronúcleo / [Evaluation of the genotoxicity of *Ilex paraguariensis* (yerba mate) by micronucleus test]. Rev. Bras. Plantas Med. 16, 2, Suppl 1, 345-349 [Portuguese, English abstract]. DOI:10.1590/1983-084X/12_058.
Alkhatib A. and Atcheson, R. (2017) Yerba maté (*Ilex paraguariensis*) metabolic, satiety, and mood state effects at rest and during prolonged exercise. Nutrients 9, 882 [15pp]. DOI:10.3390/nu9080882.
Ana Covarrubias-Cárdenas et al, "Antioxidant Capacity and UPLC-PDA ESI-MS Phenolic Profile of Stevia rebaudiana Dry Powder Extracts Obtained by Ultrasound Assisted Extraction", Agronomy,vol. 8, No. 9, Aug. 31, 2018 (Aug. 31, 2018), p. 170.
Analysis of the chemical constituents of Stevia rebausiana and its sweetness Reb M structure, Mar. 20, 2012, Journal of Beijing University of Chemical Technology (Natural Science).
Anonymous, "Sparkling Organic Grapefruit Ginger Soda", GNPD 2012, retrieved from www.gnpd.comDatabase accession No. 1790955.
Anonymous, "Stevia production process | Cargill no-calories sweeteners | Cargill", Nov. 4, 2020 (Nov. 4, 2020), Retrieved from the Internet: URL:https://www.cargill.com/food-beverage/emea/stevia-based-sweeteners-production-process.
Anonymous, "Steviol Glycosides Based Table Sweetener", GNPD-Dec. 14, 2018 (Dec. 14, 2018), Database accession No. 6205393.
Aranda Gonzalez, et al., "Effect of different drying methods on the composition of steviol glycosides in Stevia rebaudiana Bertoni leaves," Int. Agrophys., 2017, 31, 139-144.
Arthur, R., "'The stevia story has changed!' PureCircle on the evolution of the natural sweetener," Mar. 11, 2019, Beveragedaily.com.
Augustijns and Brewster, "Solvent systems and their selection in pharmaceutics and biopharmaceutics," Springer, 2009.
Baeza Gema et al: "Dihydrocaffeic acid, a major microbial metabolite of chlorogenic acids, shows similar protective effect than a yerba mate phenolic extract against oxidative stress in HepG2 cells", Food Research International, Elsevier, Amsterdam, NL, vol. 87, Jun. 17, 2016 (Jun. 17, 2016), pp. 25-33, XP029671195, ISSN: 0963-9969, DOI:10.1016/J.FOODRES.2016.06.011.
Balsan G., et al. (2019) Effect of yerba mate and green tea on paraoxonase and leptin levels in patients affected by overweight or obesity and dyslipidemia: a randomized clinical trial. Nutr. J. 18, 5 [10pp]. DOI:10.1186/s12937-018-0426-y.
Bariana D. S., et al. (1965) Chlorogenic acid: further evidence for its antigenic and allergenic activity. Nature 207, 1155-1157. DOI:10.1038/2071155a0.
Bartoshuk et al., "Sweet Taste of Water Induced by Artichoke," Dec. 1, 1972, Science, 178 (4064), 988-990.
Berte et al. (2011) J. Agric. Food Chem. 59: 5523-5527. (Year: 2011).
Bidau C. J., et al. (2004) Evaluation of the genotoxicity of aqueous extracts of Ilex paraguariensis St. Hil. (*Aquifoliaceae*) using the Allium test. Cytologia 69, 109-117. DOI:10.1508/cytologia.69.109.
Boaventura B. C., et al (2012) Association of mate tea (*Ilex paraguariensis*) intake and dietary intervention and effects on oxidative stress biomarkers of dyslipidemic subjects. Nutrition 28, 657-664. DOI:10.1016/j.nut.2011.10.017.
Boaventura B. C., et al (2013) Antioxidant potential of mate tea (*Ilex paraguariensis*) in type 2 diabetic mellitus and pre-diabetic individuals. J. Funct. Foods 5, 1057-1064. DOI:10.1016/j.jff.2013.03.001.
Boaventura B. C., et al (2015) Effect of yerba mate (*Ilex paraguariensis* A. St. Hil.) infusion obtained by freeze concentration technology on antioxidant status of healthy individuals. LWT Food Sci. Technol. 62, 948-954. DOI:10.1016/j.lwt.2015.02.028.
Boaventura, B. C. B., et al (2013). Enhancement of bioactive compounds content and antioxidant activity of aqueous extract of

(56) References Cited

OTHER PUBLICATIONS mate (*Ilex paraguariensis* A. St. Hil.) through freeze concentration technology. Food Research International, 53, 686e692.
Borges M. C., et al. (2013) The effect of mate tea (*Ilex paraguariensis*) on metabolic and inflammatory parameters in high-fat diet-fed Wistar rats. Int. J. Food Sci. Nutr. 64, 561-569. DOI:10.3109/09637486.2012.759188.
Bortoluzzi M.-C., et al (2014) Frequency of micronucleus in oral epithelial cells after exposure to mate-tea in healthy humans. Med. Oral Patol. Oral Cir. Bucal. 19, e345-e349. DOI:10.4317/medoral.19570.
Brent, Rhea, "Investigating differences in solubility between crystalline and amorphous forms of pharmaceuticals," AstraZeneca, Mat 2006.
Brittain, Harry, "Thermodynamic vs. kinetic solubility: knowing which is which," American Pharmaceutical Review, 2014.
Carvalho Ribeiro M., et al (2017) The effects of roasted yerba mate (*Ilex paraguariensis* A. ST. Hil.) consumption on glycemia and total serum creatine phosphokinase in patients with traumatic brain injury. J. Funct. Foods 28, 240-245. DOI:10.1016/j.jff.2016.11.
Chang, et al., "Stability studies of stevioside and Rebaudioside A in carbonated beverages," J. Agric. Food Chem., 1983, 31, 409-412.
Chaube S. and Swinyard C. A. (1976) Teratological and toxicological studies of alkaloidal and phenolic compounds from *Solanum tuberosum* L. Toxicol. Appl. Pharmacol. 36, 227-237. DOI:10.1016/0041-008X(76)90002-8.
Chen J., et al. (2018) Dietary chlorogenic acid improves growth performance of weaned pigs through maintaining antioxidant capacity and intestinal digestion and absorption function. J. Anim. Sci. 96, 1108-1118. DOI:10.1093/jas/skx078.
Chiou, et al., "A comparison of crystallisation approaches in spray drying," Jounral of Food Engineering, 2008.
Cilliers, et al., "Total polyphenols in apples and ciders; correlation with chlorogenic acid," Journal of Food Science, vol. 55, No. 5, 1990, pp. 1458-1459.
Clifford, "Chlorogenic acids and other cinnamates—nature, occurance, and dietary burden," Journal of the Science of Food and Agriculture, 79:362-372 (1999).
Coquerel, Gerard, "Crystallization of molecular systems from solution: phase diagrams, supersturation, and other basic concepts," Chem Soc Rev, 2014.
Craig et al., "Performance review of a fast HPLC-UV method for the quantification of chorogenic acids in green coffee bean extracts," Talanta, 154 (2016) 481-485.
Crammer and R I Kan B: II Properties and syntheses of sweetening agents, Chemical Society Reviews, Royal Society of Chemistry, UK, vol. 6, Jan. 1, 1977 (Jan. 1, 1977), pp. 431-465, XP009150156, ISSN: 0306-0012 p. 437, paragraph 2—p. 438, paragraph 1.
Cros et al., "Solvent Extraction of Oil and Chlorogenic Acid from Green Cofffee Part I: Equilibrium Data," Journal of Food Engineering 10 (1989) 1-11.
Cuesta A., et al (2018) Efecto agudo del consumo de yerba mate (*Ilex paraguariensis*) sobre el ritmo cardíaco en pacientes derivados para estudio Holter [Acute effect of yerba mate (*Ilex paraguariensis*) consumption on heart rhythm in patients referred for Holter study] [epub ahead of print]. Arch. Cardiol. Mex. xxx, Jun. 2, 2018 [1-6] [Spanish, English abstract]. DOI:10.1016/j.acmx.2018.05.004.
De Andrade F., Coehlo de Albuquerque C. A., Maraschin M. and da Silva E. L. (2012) Safety assessment of yerba mate (*Ilex paraguariensis*) dried extract: results of acute and 90 days subchronic toxicity studies in rats and rabbits. Food Chem. Toxicol. 50, 328-334. DOI:10.1016/j.fct.2011.08.028.
De Meneses Fujii et al. (2014) Yerba Mate (*Ilex paraguariensis*) modulates NF-kappaB pathway and AKT expression in the liver of rats fed on a high-fat diet. Int. J. Food Sci. Nutr. 65, 967-976. DOI:10.3109/09637486.2014.945153.
De Morais E. C., et al (2009) Consumption of yerba mate (*Ilex paraguariensis*) improves serum lipid parameters in healthy dyslipidemic subjects and provides an additional LDL-cholesterol reduction in individuals on statin therapy. J. Agric. Food Chem. 57, 8316-8324. DOI:10.1021/jf901660g.
Deladino L., et al., "Major phenolics in Yerba mate extracts(*Ilex paraguariensis*) and their contribution to the total antioxidant capacity," Food and Nutritional Science, 4, 2013.
Douglass, et al., "Kinetics of dissolution of an amorphous solid," J. Phys. Chem. B, 2018.
DuBois, G. E., et al., "Concentration-Response relationship of sweeteners," ACS Syposium Series, 1991.
Edgar Naegele, "Determination of Chlorogenic Acid in Coffee Products According to DIN 10767," Sep. 1, 2016, Agilent Technology, INC.
Eklund A. (1975) Effect of chlorogenic acid in a casein diet for rats. Nutritional and pathological observations. Nutr. Metab. 18, 258-264. DOI:10.1159/000175603.
Enokuchi Y., et al. (2020) Effects of chlorogenic acids on menopausal symptoms in healthy women: a randomized, placebo-controlled, double-blind, parallel-group trial. Nutrients 12, 3757 [12pp]. DOI:10.3390/nu12123757.
Erk T., et al. (2012) Dose-dependent absorption of chlorogenic acids in the small intestine assessed by coffee consumption in ileostomists. Mol. Nutr. Food Res. 56, 1488-1500. DOI:10.1002/mnfr.201200222.
Folwarczna J., et al. (2012) Effects of caffeic and chlorogenic acids on bone mechanical properties in female rats. Bone 50, Suppl. 1, S158 [abstract PP306]. DOI:10.1016/j.bone.2012.02.495.
Fonseca C. A., et al (2000) Nontoxic, mutagenic, and clastogenic activities of mate-chimarrao (*Ilex paraguariensis*). J. Environ. Pathol. Toxicol. Oncol. 19, 333-346.
Frank J., et al. (2003) The dietary hydroxycinnamate caffeic acid and its conjugate chlorogenic acid increase vitamin E and cholesterol concentrations in Sprague-Dawley rats. J. Agric. Food Chem. 51, 2526-2531. DOI:10.1021/if026127k.
Amazon [online], Aug. 7, 2012 [Retrieval Date: Mar. 28, 2024], Internet: <URL: https://amzn.asia/d/jcWACRC>.
Hariprasad "Cocrystals of Ethenzamide: Study of Structural and Physicochemical Properties", Cryst. Growth Des. 2016; 16: 4473-4481 (Year: 2016).
Kuminek "Cocrystals to facilitate delivery of poorly soluble compounds beyond-rule-of-5", Adv. Drug Deliv. Rev. 2016; 101: 143-166 (Year: 2016).
Molina-Calle et al., "Development and application of a quantitative method based on LC-QqQ MS/MS for determination of steviol glycosides in Stevia leaves", Talanta 154 (2016) 263-269.

STEVIOL GLYCOSIDE COMPOSITIONS WITH REDUCED SURFACE TENSION

CROSS REFERENCE TO RELATED APPLICATIONS

This application is a Continuation of U.S. application Ser. No. 16/374,388, filed Apr. 3, 2019, which is a Continuation of International Application No. PCT/US2018/054804, filed Oct. 8, 2018, which claims the benefit of U.S. Provisional Application No. 62/569,279, filed Oct. 6, 2017, each of which is incorporated by reference herein in its entirety. This application claims the benefit of U.S. Provisional Application Ser. No. 62/676,722, filed May 2018, which application is incorporated by reference herein in its entirety.

FIELD

The present disclosure generally relates to steviol glycoside compositions with reduced surface tension having one or more surface tension reducing compounds and one or more steviol glycosides. The present disclosure also discloses methods of making and using these steviol glycoside compositions with reduced surface tension.

BACKGROUND

Traditionally, sugars such as sucrose and fructose have been used to provide a sweetened taste to foods, beverages, pharmaceuticals, and oral hygiene/cosmetic products. While these sugars can provide a taste preferred by consumers, they are caloric. In the last decades, as consumers have become more conscious of caloric intake, there has been increased interest in reducing the amount of caloric sugars in products. One approach to reduce the amount of these sugars has been to replace caloric sugars with non-caloric sweeteners. Non-caloric sweeteners can provide a sweetened taste to foods, beverages, pharmaceuticals, and oral hygiene/cosmetic products without adding calories. Steviol glycosides are an example of high intensity non-caloric sweeteners that can provide a sweetened taste to products without adding calories.

Steviol glycosides are glycosides of steviol, a diterpene compound and are about 150 to 450 times sweeter than sugar. Examples of steviol glycosides are described in WO 2013/096420 (see, e.g., listing in FIG. 1); and in Ohta et. al., "Characterization of Novel Steviol Glycosides from Leaves of *Stevia rebaudiana* Morita," J. Appl. Glycosi., 57, 199-209 (2010) (See, e.g., Table 4 at p. 204). Structurally, the diterpene glycosides are characterized by a single base, steviol, and differ by the presence of carbohydrate residues at positions C13 and C19, as presented in FIGS. 2a-2k of PCT Patent Publication WO 2013/096420. Steviol glycosides can include one or more of dulcoside A, stevioside, steviolbioside, rubusoside and/or one or more of rebaudioside A, B, C, D, E, F, G, H, I, J, K, L, M, N, and/or O.

While steviol glycoside can provide a sweetened taste to products, there can be challenges to preparing products with steviol glycoside. In some cases, there may be advantages to preparing a product comprising steviol glycoside composition with reduced surface tension. For example, consumers may prefer a product comprising a steviol glycoside composition with reduced surface tension. Such products can include beverages such as carbonated soda drinks, flavored waters, carbonated flavored waters, and other beverages. Such products can also include dry sweetener compositions, dry drink mixes, and concentrated liquid drink mixes.

Although conventional surfactants can be used to reduce surface tension in food applications, there may be drawbacks to their use with steviol glycoside products. For example, many consumers select steviol glycoside products because these consumers prefer products with natural ingredients. These consumers may not desire a steviol glycoside product with conventional surfactant agents. Likewise, some consumers may prefer a steviol glycoside product made from natural ingredients. Similarly, some consumers may prefer a steviol glycoside product with an ingredient label that lists natural ingredients. Therefore, these consumers may prefer steviol glycoside products with a surface tension reducing compound isolated from a natural source such as a botanical source.

It is an object of the present disclosure to provide a surface tension reducing compound for steviol glycoside compositions with reduced surface tension, for example in the preparation of foods, beverages, pharmaceuticals, and oral hygiene/cosmetic products with steviol glycoside. It is also an object of the present disclosure to provide a surface tension reducing compound isolated from a natural source such as a botanical source.

SUMMARY

The present disclosure generally relates to steviol glycoside compositions comprising a steviol glycoside and a surface tension reducing compound in an amount effect to reduce surface tension. One aspect provides a steviol glycoside composition with reduced surface tension, the composition comprising an aqueous solution of a steviol glycoside and a surface tension reducing compound in an amount effective to reduce surface tension by at least 10% when compared to a steviol glycoside solution without a surface tension reducing compound. In some aspects, the steviol glycoside composition with reduced surface tension comprises the surface tension reducing compound in an amount effective to reduce surface tension by at least 20%, at least 30%, at least 40%, at least 50%, at least 60%, at least 70%, at least 80% or at least 90% compared to a steviol glycoside solution without the surface tension reducing compound. In some aspects, the steviol glycoside comprises one or more steviol glycosides selected from the group consisting of rebaudioside A, rebaudioside B, rebaudioside C, rebaudioside D, rebaudioside E, rebaudioside F, rebaudioside M, rubusoside, dulcoside A, rebaudioside I, rebaudioside Q, rebaudioside N, rebaudioside O, 1,2-stevioside, 1,3-stevioside, steviol-1,2-bioside, steviol-1,3-bioside, steviol-13-O-glucoside (13-SMG), and steviol-19-O-glucoside (19-SMG). In other aspects, the steviol glycoside comprises one or more steviol glycosides selected from the group consisting of rebaudioside D and rebaudioside M.

In some aspects, the surface tension reducing compound comprises one or more compounds selected from the group consisting of a quinic acid, caffeic acid, ferulic acid, sinapic acid, p-coumaric acid, an ester of quinic acid, an ester of caffeic acid, an ester of ferulic acid, an ester of sinapic acid, an ester of p-coumaric acid, an ester of caffeic acid and quinic acid, an ester of caffeic acid and quinic acid comprising a single caffeic acid moiety, an ester of caffeic acid and quinic acid comprising more than one caffeic acid moiety, an ester of ferulic acid and quinic acid, an ester of ferulic acid and quinic acid comprising a single ferulic acid moiety, an ester of ferulic acid and quinic acid comprising more than one ferulic acid moiety, an ester of sinapic acid and quinic acid, an ester of sinapic acid and quinic acid comprising a single sinapic acid moiety, an ester of sinapic acid and quinic acid comprising more than one sinapic acid moiety, an ester of p-coumaric acid and quinic acid, an ester of p-coumaric acid and quinic acid comprising a single p-coumaric acid moiety, an ester of p-coumaric acid and quinic acid comprising more than one p-coumaric acid moiety, a caffeic ester of 3-(3,4-dihydroxyphenyl)lactic acid, an ester of caffeic acid and tartaric acid, an ester of caffeic acid and tartaric acid comprising a single caffeic acid moiety, an ester of caffeic acid and tartaric acid comprising more than one caffeic acid moiety, salt thereof and/or isomers thereof. In other aspects, the surface tension reducing compound comprises one or more compounds selected from the group consisting of chlorogenic acid, neochlorogenic acid, cryptochlorogenic acid, 3-O-caffeoylquinic acid, 4-O-caffeoylquinic acid, 5-O-caffeoylquinic acid, 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, 4,5-dicaffeoylquinic acid, 3-O-feruloylquinic acid, 4-O-feruloylquinic acid, 5-O-feruloylquinic acid, 3,4-diferuloylquinic acid, 3,5-diferuloylquinic acid, 4,5-diferuloylquinic acid, rosmarinic acid, cichoric acid, caftaric acid, monocaffeoyltartaric acid, dicaffeoyltartaric acid and salts and/or isomers thereof. In some aspects, the surface tension reducing compound comprises one or more compounds selected from the group consisting of chlorogenic acid, neochlorogenic acid, cryptochlorogenic acid, 3-O-caffeoylquinic acid, 4-O-caffeoylquinic acid, 5-O-caffeoylquinic acid, 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, and 4,5-dicaffeoylquinic acid. In other aspects, the surface tension reducing compound is enriched for one or more dicaffeoylquinic acids, and salts thereof. In some aspects, the surface tension reducing compound comprises 10% or more, 15% or more, 20% or more, 25% or more, 30% or more, 35% or more, 40% or more, 45% or more, or 50% or more dicaffeoylquinic acids, and salts thereof.

In some aspects, the composition comprises a final concentration of steviol glycoside of between about 1 ppm to about 1000 ppm, about 1 ppm to about 10000 ppm, about 1 ppm to about 100000 ppm, about 1 ppm to about 200000 ppm, or about 1 ppm to about 300000 ppm. In some aspects, the composition comprises a final concentration of steviol glycoside of between about 100 ppm to about 5000 ppm, about 200 ppm to about 5000 ppm, 300 ppm to about 5000 ppm, 400 ppm to about 5000 ppm, 500 ppm to about 5000 ppm, 600 ppm to about 5000 ppm, 700 ppm to about 5000 ppm, 800 ppm to about 5000 ppm, 900 ppm to about 5000 ppm, or 1000 ppm to about 5000 ppm. In other aspects, the composition comprises a final concentration of surface tension reducing compound of between about 1 ppm to about 1000 ppm, about 1 ppm to about 10000 ppm, about 1 ppm to about 100000 ppm, about 1 ppm to about 200000 ppm, or about 1 ppm to about 300000 ppm. In some aspects, the composition comprises a final concentration of surface tension reducing compound of between about 100 ppm to about 5000 ppm, about 200 ppm to about 5000 ppm, 300 ppm to about 5000 ppm, 400 ppm to about 5000 ppm, 500 ppm to about 5000 ppm, 600 ppm to about 5000 ppm, 700 ppm to about 5000 ppm, 800 ppm to about 5000 ppm, 900 ppm to about 5000 ppm, or 1000 ppm to about 5000 ppm. In some aspects, the composition comprises a ratio of surface tension reducing compound to steviol glycoside of 0.1:1 to 5:1, about 0.5:1 to 4:1, or about 1:1 to 3:1.

In some aspects, the surface tension reducing compound is prepared from a botanical source. In some aspects, the botanical source is selected from the group consisting of eucommoia ulmoides, honeysuckle, *Nicotiana benthamiana*, globe artichoke, cardoon, *Stevia, Stevia rebaudiana*, monkfruit, coffee, coffee beans, green coffee beans, tea, white tea, yellow tea, green tea, oolong tea, black tea, red tea, post-fermented tea, bamboo, heather, sunflower, blueberries, cranberries, bilberries, grouseberries, whortleberry, lingonberry, cowberry, huckleberry, grapes, chicory, eastern purple coneflower, echinacea, Eastern pellitory-of-the-wall, Upright pellitory, Lichwort, Greater celandine, Tetterwort, Nipplewort, Swallowwort, Bloodroot, Common nettle, Stinging nettle, Potato, Potato leaves, Eggplant, Aubergine, Tomato, Cherry tomato, Bitter apple, Thorn apple, Sweet potato, apple, Peach, Nectarine, Cherry, Sour cherry, Wild cherry, Apricot, Almond, Plum, Prune, Holly, Yerba mate, Mate, *Ilex paraguariensis*, Guayusa, Yaupon Holly, Kuding, Guarana, Cocoa, Cocoa bean, Cacao, Cacao bean, Kola nut, Kola tree, Cola nut, Cola tree, Hornwort, Ostrich fern, Oriental ostrich fern, Fiddlehead fern, Shuttlecock fern, Oriental ostrich fern, Asian royal fern, Royal fern, Bracken, Brake, Common bracken, Eagle fern, Eastern brakenfern, dandelion, algae, seagrasses, Clove, Cinnamon, Indian bay leaf, Nutmeg, Bay laurel, Bay leaf, Basil, Great basil, Saint-Joseph's-wort, Thyme, Sage, Garden sage, Common sage, Culinary sage, Rosemary, Oregano, Wild marjoram, Marjoram, Sweet marjoram, Knotted marjoram, Pot marjoram, Dill, Anise, Star anise, Fennel, Florence fennel, Tarragon, Estragon, Mugwort, Licorice, Liquorice, Soy, Soybean, Soyabean, Soya vean, Wheat, Common wheat, Rice, Canola, Broccoli, Cauliflower, Cabbage, Bok choy, Kale, Collard greens, Brussels sprouts, Kohlrabi, Winter's bark, Elderflower, Assa-Peixe, Greater burdock, Valerian, and Chamomile. In some aspects, the botanical source is yerba mate, chicory, rosemary, and/or *Stevia*.

One aspect provides a beverage concentrate solution with reduced surface tension, the solution comprising a steviol glycoside and a surface tension reducing compound in an amount effective to reduce surface tension by at least 10% during at least six-fold dilution of the concentrate solution. In some aspects, the steviol glycoside comprises one or more steviol glycosides selected from the group consisting of rebaudioside D and rebaudioside M. In some aspects, the surface tension reducing compound comprises one or more compounds selected from the group consisting of a quinic acid, caffeic acid, ferulic acid, sinapic acid, p-coumaric acid, an ester of quinic acid, an ester of caffeic acid, an ester of ferulic acid, an ester of sinapic acid, an ester of p-coumaric acid, an ester of caffeic acid and quinic acid, an ester of caffeic acid and quinic acid comprising a single caffeic acid moiety, an ester of caffeic acid and quinic acid comprising more than one caffeic acid moiety, an ester of ferulic acid and quinic acid, an ester of ferulic acid and quinic acid comprising a single ferulic acid moiety, an ester of ferulic acid and quinic acid comprising more than one ferulic acid moiety, an ester of sinapic acid and quinic acid, an ester of sinapic acid and quinic acid comprising a single sinapic acid moiety, an ester of sinapic acid and quinic acid comprising more than one sinapic acid moiety, an ester of p-coumaric acid and quinic acid, an ester of p-coumaric acid and quinic acid comprising a single p-coumaric acid moiety, an ester of p-coumaric acid and quinic acid comprising more than one p-coumaric acid moiety, a caffeic ester of 3-(3,4-dihydroxyphenyl)lactic acid, an ester of caffeic acid and tartaric acid, an ester of caffeic acid and tartaric acid comprising a single caffeic acid moiety, an ester of caffeic acid and tartaric acid comprising more than one caffeic acid moiety, salt thereof and/or isomers thereof. In some aspects, the surface tension reducing compound comprises one or more compounds selected from the group consisting of chlorogenic acid, neochlorogenic acid, cryptochlorogenic acid, 3-O-caffeoylquinic acid, 4-O-caffeoylquinic acid, 5-O-caffeoylquinic acid, 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, 4,5-dicaffeoylquinic acid, 3-O-feruloylquinic acid, 4-O-feruloylquinic acid, 5-O-feruloylquinic acid, 3,4-diferuloylquinic acid, 3,5-diferuloylquinic acid, 4,5-diferuloylquinic acid, rosmarinic acid, cichoric acid, caftaric acid, monocaffeoyltartaric acid, dicaffeoyltartaric acid and salts and/or isomers thereof. In some aspects, the surface tension reducing compound comprises one or more compounds selected from the group consisting of chlorogenic acid, neochlorogenic acid, cryptochlorogenic acid, 3-O-caffeoylquinic acid, 4-O-caffeoylquinic acid, 5-O-caffeoylquinic acid, 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, and 4,5-dicaffeoylquinic acid. In some aspects, the surface tension reducing compound is enriched for one or more dicaffeoylquinic acids, and salts thereof. In some aspects, the surface tension reducing compound comprises 10% or more, 15% or more, 20% or more, 25% or more, 30% or more, 35% or more, 40% or more, 45% or more, or 50% or more dicaffeoylquinic acids, and salts thereof.

In some aspects, the concentrate solution further comprises a steviol glycoside concentration of between about 100 ppm to about 5000 ppm, about 200 ppm to about 5000 ppm, 300 ppm to about 5000 ppm, 400 ppm to about 5000 ppm, 500 ppm to about 5000 ppm, 600 ppm to about 5000 ppm, 700 ppm to about 5000 ppm, 800 ppm to about 5000 ppm, 900 ppm to about 5000 ppm, or 1000 ppm to about 5000 ppm. In some aspects, concentrate solution further comprises a concentration of surface tension reducing compound of between about 100 ppm to about 5000 ppm, about 200 ppm to about 5000 ppm, 300 ppm to about 5000 ppm, 400 ppm to about 5000 ppm, 500 ppm to about 5000 ppm, 600 ppm to about 5000 ppm, 700 ppm to about 5000 ppm, 800 ppm to about 5000 ppm, 900 ppm to about 5000 ppm, or 1000 ppm to about 5000 ppm. In some aspects, the concentrate solution further comprises a concentration of surface tension reducing compound of between about 1000 ppm to about 10000 ppm, about 1000 ppm to about 9000 ppm, 1000 ppm to about 8000 ppm, 1000 ppm to about 7000 ppm, 1000 ppm to about 6000 ppm, 1000 ppm to about 5000 ppm, or 1800 ppm to about 5400 ppm. In some aspects, the concentrate solution further comprises a ratio of surface tension reducing compound to steviol glycoside of 0.1:1 to 5:1, about 0.5:1 to 4:1, or about 1:1 to 3:1.

In some aspects, the concentrate solution further comprises surface tension reducing compound prepared from yerba mate, chicory, rosemary, and/or *Stevia*. In some aspects, the concentrate solution has a pH of 1.5 to 4.

One aspect provides a steviol glycoside composition comprising an admixture of steviol glycoside and surface tension reducing compound, wherein an aqueous solution prepared from the steviol glycoside composition has a reduced surface tension compared to a steviol glycoside solution without surface tension reducing compound. In some aspects, the steviol glycoside comprises one or more steviol glycosides selected from the group consisting of rebaudioside D and rebaudioside M. In some aspects, the steviol glycoside comprises rebaudioside A. In some aspects, the surface tension reducing compound comprises one or more compounds selected from the group consisting of chlorogenic acid, neochlorogenic acid, cryptochlorogenic acid, 3-O-caffeoylquinic acid, 4-O-caffeoylquinic acid, 5-O-caffeoylquinic acid, 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, 4,5-dicaffeoylquinic acid, 3-O-feruloylquinic acid, 4-O-feruloylquinic acid, 5-O-feruloylquinic acid, 3,4-diferuloylquinic acid, 3,5-diferuloylquinic acid, 4,5-diferuloylquinic acid, rosmarinic acid, cichoric acid, caftaric acid, monocaffeoyltartaric acid, dicaffeoyltartaric acid and salts and/or isomers thereof. In some aspects, the surface tension reducing compound comprises one or more compounds selected from the group consisting of chlorogenic acid, neochlorogenic acid, cryptochlorogenic acid, 3-O-caffeoylquinic acid, 4-O-caffeoylquinic acid, 5-O-caffeoylquinic acid, 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, and 4,5-dicaffeoylquinic acid. In some aspects, the surface tension reducing compound is enriched for one or more dicaffeoylquinic acids, and salts thereof. In some aspects, the surface tension reducing compound comprises 10% or more, 15% or more, 20% or more, 25% or more, 30% or more, 35% or more, 40% or more, 45% or more, or 50% or more dicaffeoylquinic acids, and salts thereof. In some aspects, the admixture comprises a ratio of surface tension reducing compound to steviol glycoside of 0.1:1 to 5:1, about 0.5:1 to 4:1, or about 1:1 to 3:1. In some aspects, the surface tension reducing compound is prepared from one or more botanical sources selected from the group consisting of yerba mate, chicory, rosemary, and *Stevia*. In some aspects, the steviol glycoside composition further comprises a buffering system to provide a pH of 1.5 to 4 in to the aqueous solution prepared from the steviol glycoside composition.

One aspect provides a method for reducing surface tension in a steviol glycoside solution, the method comprising contacting a steviol glycoside and a surface tension reducing compound to prepare any of the steviol glycoside compositions with reduced surface tension described above. In some aspects, the surface tension is reduced by at least 10%, at least 20%, at least 30%, at least 40%, at least 50%, at least 60%, at least 70%, at least 80% or at least 90% compared to a steviol glycoside solution without the surface tension reducing compound.

One aspect provides a method for producing a reduced surface tension steviol glycoside solution, the method comprising preparing any of the reduced steviol glycoside compositions described above. In some aspects, the surface tension is reduced by at least 10%, at least 20%, at least 30%, at least 40%, at least 50%, at least 60%, at least 70%, at least 80% or at least 90% compared to a steviol glycoside solution without surface tension reducing compound.

DETAILED DESCRIPTION

The disclosure relates generally to steviol glycoside compositions with reduced surface tension comprising a steviol glycoside and a surface tension reducing compound in an amount effective to reduce surface tension of the steviol glycoside composition.

In some aspects, the term surface tension refers to a tension of a surface film of a liquid caused by attraction of molecules in the surface layer by a bulk of the liquid which tends to minimize surface area. In other aspects, an aqueous solution with reduced surface tension may exhibit an increase in foam formation upon introduction of a gas, may result in a foam that lasts longer over time, and/or may exhibit a smaller bubble size of the gas in the aqueous solution and/or in the foam. For example, a steviol glycoside composition with a surface tension reducing compound can comprise a reduced surface tension when compared with a similar composition without the surface tension reducing compound.

An example of a steviol glycoside composition with reduced surface tension comprises an aqueous solution of a steviol glycoside and surface tension reducing compound in an amount effective to reduce surface tension. In some aspects, a steviol glycoside composition with reduced surface tension comprises an aqueous solution of a steviol glycoside and a surface tension reducing compound in an amount effective to reduce surface tension by at least 10%. In other aspects, a steviol glycoside composition with reduced surface tension comprises an aqueous solution of a steviol glycoside and a surface tension reducing compound in an amount effective to reduce surface tension by at least 10%, 15%, 20%, 25%, 30%, 35%, 40%, 45%, 50%, 55%, 60%, 65%, 70%, 75%, 80%, 85%, 90%, 95% or more.

In some aspects, the aqueous solution comprises primarily water. The aqueous solution can also be buffered with any suitable buffering system, including, but not limited to, one or more buffers such as a phosphate, a citrate, ascorbate, lactate, acetate, and the like. The buffer can comprise 1-1000 mM of the anion component. In other aspects, the aqueous solution comprises a citrate/phosphate buffer. In some aspects, citrate/phosphate buffer can have a pH of 2 to 4.

The amounts of steviol glycoside in the steviol glycoside composition and the surface tension reducing composition can be expressed in relation to one another, or to the total amount of steviol glycosides (TSG), such as a weight percentage of the total amount of steviol glycosides (TSG), or to the total amount of surface tension reducing compound, or a ratio, or range of ratios, expressed as a weight percent, or molar percent.

Figure 1:
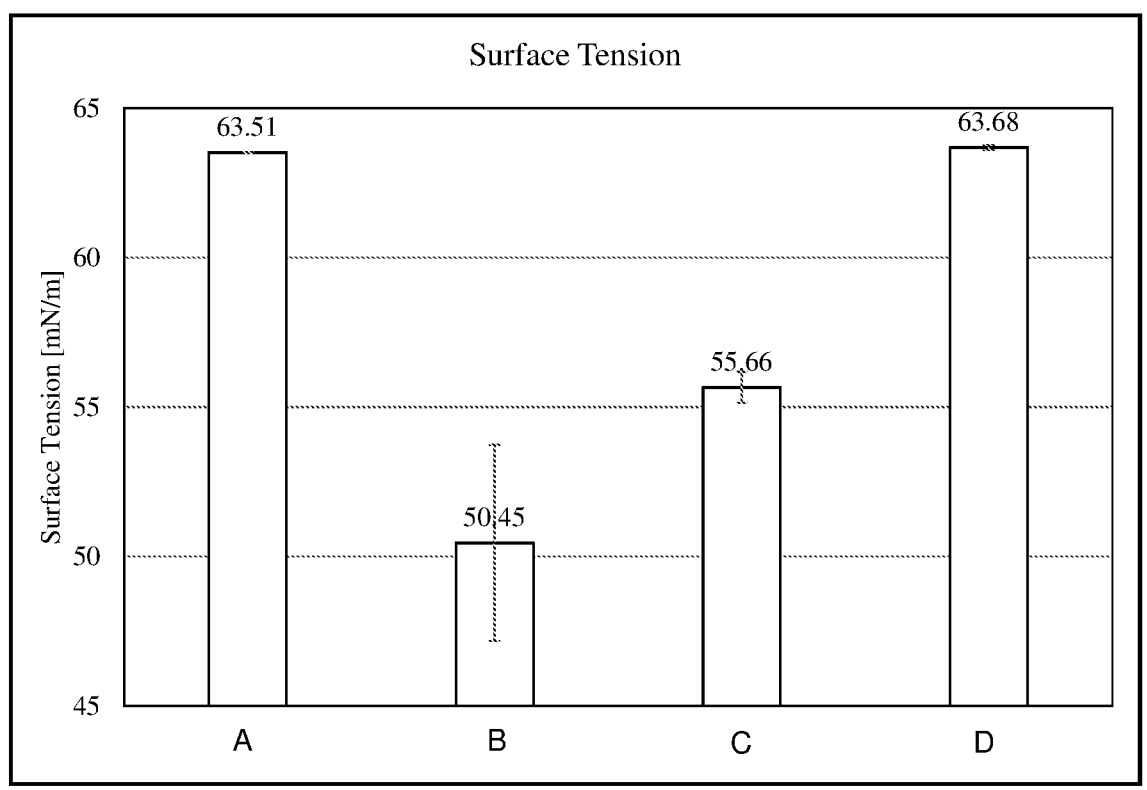
FIG. 1 shows surface tension measurements for a control solution of a steviol glycoside blend (RM80), a control solution of surface tension reducing compound(isolated from yerba mate), a test solution of steviol glycoside blend with surface tension reducing compound(isolated from yerba mate), and a test solution of steviol glycoside with chlorogenic acid(commercial preparation).

The steviol glycoside composition can include one or more steviol glycosides. In some aspects, the term steviol glycoside refers to Rebaudioside A (Reb A) (CAS #58543-16-1), Rebaudioside B (Reb B) (CAS #58543-17-2), Rebaudioside C (Reb C) (CAS #63550-99-2), Rebaudioside D (Reb D) (CAS #63279-13-0), Rebaudioside E (Reb E) (CAS #63279-14-1), Rebaudioside F (Reb F) (CAS #438045-89-7), Rebaudioside M (Reb M) (CAS #1220616-44-3), Rubusoside (CAS #63849-39-4), Dulcoside A (CAS #64432-06-0), Rebaudioside I (Reb I) (MassBank Record: FU000332), Rebaudioside Q (Reb Q), Rebaudioside O (Reb O), Rebaudioside N (Reb N) (CAS #1220616-46-5), 1,2-Stevioside (CAS # 57817-89-7), 1,3-Stevioside (Reb G), Steviol-1,2-Bioside (MassBank Record: FU000299), Steviol-1,3-Bioside, Steviol-13-O-glucoside (13-SMG), Steviol-19-O-glucoside (19-SMG), and steviol glycoside having 1, 2, 3, 4, 5, 6, 7, 8, 9, 10 or sugar additions (e.g., glucose, rhamnose, and/or xylose), and isomers thereof. See FIG. 1; see also, Steviol Glycosides Chemical and Technical Assessment 69th JECFA, 2007, prepared by Harriet Wallin, Food Agric. Org.

Exemplary steviol glycosides can include rebaudioside M, rebaudioside D, rebaudioside A, rebaudioside B, rebaudioside N, and/or stevioside. In some aspects, one or more of the steviol glycosides are produced by fermentation by an engineered microorganism. For example, rebaudioside D and M can be produced by an engineered organism and then isolated to produce a steviol glycoside composition of primarily rebaudioside D and rebaudioside M as the predominant steviol glycoside species. In other aspects, the steviol glycoside composition can comprise rebaudioside D and rebaudioside M in an amount greater than other steviol glycosides. In some aspects, one or more of the steviol glycosides are isolated from *Stevia rebaudiana*.

In some aspects, steviol glycosides can include rebaudioside A. For example, steviol glycosides can include blends of rebaudioside A and one or more other steviol glycosides. An example of a blend of rebaudioside A with one or more other steviol glycosides comprises 60% or more rebaudioside A (RA60). Another example of a blend of rebaudioside A with one or more other steviol glycosides comprises 80% or more rebaudioside A (RA80). Another example of a blend of rebaudioside A with one or more other steviol glycosides comprises 95% or more rebaudioside A (RA95). In other aspects, steviol glycosides can include blends of one or more of RebA, RebB, RebC, RebD, RebE, RebF, RebM, rubusoside, dulcoside A, RebI, RebQ, 1,2 stevioside, 1,3 stevioside, steviol-1,2-bioside, steviol-1,3-bioside, 13-SMG, 19-SMG, a tri-glycosylated steviol glycoside, a tetra-glycosylated steviol glycoside, a penta-glycosylated steviol glycoside, a hexa-glycosylated steviol glycoside, a hepta-glycosylated steviol glycoside, and isomers thereof.

In some aspects, the steviol glycoside composition can optionally be described in terms of amounts of rebaudioside M and rebaudioside D. For example, rebaudioside M and rebaudioside D can be present in the composition in a total amount of about 80% (wt) or greater (RM80), 90% (wt) or greater (RM90), or 95% (wt) or greater (RM95), of a total amount steviol glycosides in the composition. Rebaudioside M can be the predominant steviol glycoside in the composition, and can be present, for example, in an amount in the range of about 50% to about 95%, about 70% to about 90%, or about 75% to about 85% of the total amount steviol glycosides in the composition. Rebaudioside D can be in an amount less than Rebaudioside M, such as in an amount in the range of about 5% to about 25%, about 10% to about 20%, or about 10% to about 15% of the total amount steviol glycosides in the composition.

The steviol glycoside composition can optionally be expressed in terms of amounts of other known steviol glycosides that are present in lower amounts. For example, the composition can include one or more of rebaudioside A, rebaudioside B, or stevioside in an amount of about 5% (wt) or less, about 2% (wt) or less, or about 1% (wt) or less, of a total amount of steviol glycosides in the composition.

The amount of steviol glycosides in the steviol glycoside composition with reduced surface tension can vary. Steviol glycosides can be present in the steviol glycoside composition with reduced surface tension in any amount desired for the particular use. For example, steviol glycosides can be present in the steviol glycoside composition with reduced surface tension at a total steviol glycoside concentration from about 1 ppm to about 1000 ppm, from about 1 ppm to about 10000 ppm, from about 1 ppm to about 100000 ppm, from about 1 ppm to about 200000 ppm, or from about 1 ppm to about 300000 ppm. In some aspects, steviol glycosides can be present in the steviol glycoside composition with reduced surface tension at a total steviol glycoside concentration from about 100 ppm to about 5000 ppm, about 200 ppm to about 5000 ppm, 300 ppm to about 5000 ppm, 400 ppm to about 5000 ppm, 500 ppm to about 5000 ppm, 600 ppm to about 5000 ppm, 700 ppm to about 5000 ppm, 800 ppm to about 5000 ppm, 900 ppm to about 5000 ppm, or 1000 ppm to about 5000 ppm. In some aspects, steviol glycosides can be present in the steviol glycoside composition with reduced surface tension at a total steviol glycoside concentration from about 1000 ppm to about 5000 ppm, about 2000 ppm to about 5000 ppm, about 3000 ppm to about 5000 ppm, or about 4000 ppm to about 5000 ppm. In some aspects, steviol glycosides can be present in the steviol glycoside composition with reduced surface tension at a total steviol glycoside concentration of or greater than about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, or 100000 ppm. In some aspects, steviol glycosides can be present in the steviol glycoside composition with reduced surface tension at a total steviol glycoside concentration of or greater than about 200000 ppm. In some aspects, steviol glycosides can be present in the steviol glycoside composition with reduced surface tension at a total steviol glycoside concentration of or greater than about 300000 ppm. Unless otherwise expressly stated, ppm is on a by weight basis.

The amount of an individual steviol glycoside in the steviol glycoside composition with reduced surface tension can vary. For example, an individual steviol glycoside can be present in the steviol glycoside composition with reduced surface tension at a concentration from about 1 ppm to about 1000 ppm, from about 1 ppm to about 10000 ppm, from about 1 ppm to about 100000 ppm, from about 1 ppm to about 200000 ppm, or from about 1 ppm to about 300000 ppm. In some aspects, an individual steviol glycoside can be present in the steviol glycoside composition with reduced surface tension at a concentration from about 100 ppm to about 5000 ppm, about 200 ppm to about 5000 ppm, 300 ppm to about 5000 ppm, 400 ppm to about 5000 ppm, 500 ppm to about 5000 ppm, 600 ppm to about 5000 ppm, 700 ppm to about 5000 ppm, 800 ppm to about 5000 ppm, 900 ppm to about 5000 ppm, or 1000 ppm to about 5000 ppm. In some aspects, an individual steviol glycoside can be present in the steviol glycoside composition with reduced surface tension at a concentration from about 1000 ppm to about 5000 ppm, about 2000 ppm to about 5000 ppm, about 3000 ppm to about 5000 ppm, or about 4000 ppm to about 5000 ppm. In some aspects, an individual steviol glycoside can be present in the steviol glycoside composition with reduced surface tension at a concentration of or greater than about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, or 100000 ppm. In some aspects, an individual steviol glycoside can be present in the steviol glycoside composition with reduced surface tension at a concentration of or greater than about 200000 ppm. In some aspects, an individual steviol glycoside can be present in the steviol glycoside composition with reduced surface tension at a concentration of or greater than about 300000 ppm. Unless otherwise expressly stated, ppm is on a by weight basis The amount of an individual steviol glycoside in the steviol glycoside composition with reduced surface tension can vary. For example, RebA can be present in the steviol glycoside composition with reduced surface tension at a concentration from about 1 ppm to about 1000 ppm, from about 1 ppm to about 10000 ppm, from about 1 ppm to about 100000 ppm, from about 1 ppm to about 200000 ppm, or from about 1 ppm to about 300000 ppm. In some aspects, RebA can be present in the steviol glycoside composition with reduced surface tension at a concentration from about 100 ppm to about 5000 ppm, about 200 ppm to about 5000 ppm, 300 ppm to about 5000 ppm, 400 ppm to about 5000 ppm, 500 ppm to about 5000 ppm, 600 ppm to about 5000 ppm, 700 ppm to about 5000 ppm, 800 ppm to about 5000 ppm, 900 ppm to about 5000 ppm, or 1000 ppm to about 5000 ppm. In some aspects, RebA can be present in the steviol glycoside composition with reduced surface tension at a concentration from about 1000 ppm to about 5000 ppm, about 2000 ppm to about 5000 ppm, about 3000 ppm to about 5000 ppm, or about 4000 ppm to about 5000 ppm. In some aspects, RebA can be present in the steviol glycoside composition with reduced surface tension at a concentration of or greater than about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, or 100000 ppm. In some aspects, RebA can be present in the steviol glycoside composition with reduced surface tension at a concentration of or greater than about 200000 ppm. In some aspects, RebA can be present in the steviol glycoside composition with reduced surface tension at a concentration of or greater than about 300000 ppm. Unless otherwise expressly stated, ppm is on a by weight basis.

The amount of an individual steviol glycoside in the steviol glycoside composition with reduced surface tension can vary. For example, RebM can be present in the steviol glycoside composition with reduced surface tension at a concentration from about 1 ppm to about 1000 ppm, from about 1 ppm to about 10000 ppm, from about 1 ppm to about 100000 ppm, from about 1 ppm to about 200000 ppm, or from about 1 ppm to about 300000 ppm. In some aspects, RebM can be present in the steviol glycoside composition with reduced surface tension at a concentration from about 100 ppm to about 5000 ppm, about 200 ppm to about 5000 ppm, 300 ppm to about 5000 ppm, 400 ppm to about 5000 ppm, 500 ppm to about 5000 ppm, 600 ppm to about 5000 ppm, 700 ppm to about 5000 ppm, 800 ppm to about 5000 ppm, 900 ppm to about 5000 ppm, or 1000 ppm to about 5000 ppm. In some aspects, RebM can be present in the steviol glycoside composition with reduced surface tension at a concentration from about 1000 ppm to about 5000 ppm, about 2000 ppm to about 5000 ppm, about 3000 ppm to about 5000 ppm, or about 4000 ppm to about 5000 ppm. In some aspects, RebM can be present in the steviol glycoside composition with reduced surface tension at a concentration of or greater than about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, or 100000 ppm. In some aspects, RebM can be present in the steviol glycoside composition with reduced surface tension at a concentration of or greater than about 200000 ppm. In some aspects, RebM can be present in the steviol glycoside composition with reduced surface tension at a concentration of or greater than about 300000 ppm. Unless otherwise expressly stated, ppm is on a by weight basis.

In some aspects, the steviol glycosides comprise a high concentration steviol glycoside solution. In some aspects, a high concentration steviol glycoside solution comprises a steviol glycoside solution comprising a total amount of steviol glycosides (TSG) of 1% or more. A high concentration steviol glycoside solution can comprise a steviol glycoside solution comprising a total amount of steviol glycosides (TSG) of 1%, 2%, 3%, 4%, 5%, 6%, 7%, 8%, 9%, 10% or more. A high concentration steviol glycoside solution can comprise a steviol glycoside solution comprising a total amount of steviol glycosides (TSG) of 11%, 12%, 13%, 14%, 15%, 16%, 17%, 18%, 19%, 20% or more. A high concentration steviol glycoside solution can comprise a steviol glycoside solution comprising a total amount of steviol glycosides (TSG) of 21%, 22%, 23%, 24%, 25%, 26%, 27%, 28%, 29%, 30% or more. A high concentration steviol glycoside solution can comprise one or more of the steviol glycosides described above. For example a high steviol glycoside solution can comprise one or more of RebA, RebB, RebC, RebD, RebE, RebF, RebM, rubusoside, dulcoside A, RebI, RebQ, 1,2 stevioside, 1,3 stevioside, steviol-1,2-bioside, steviol-1,3-bioside, 13-SMG, 19-SMG, a tri-glycosylated steviol glycoside, a tetra-glycosylated steviol glycoside, a penta-glycosylated steviol glycoside, a hexa-glycosylated steviol glycoside, a hepta-glycosylated steviol glycoside, and isomers thereof.

Examples of surface tension reducing compounds include: caffeic acid, an ester of caffeic acid, an ester of caffeic acid and quinic acid, an ester of caffeic acid and quinic acid comprising a single caffeic acid moiety (e.g., chlorogenic acid, cryptochlorogenic acid, and neochlorogenic acid; structures of each are provided herein), an ester of caffeic acid and quinic acid comprising more than one caffeic acid moiety (e.g., 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, and 4,5-dicaffeoylquinic acid; structures of each are provided herein); ferulic acid, an ester of ferulic acid, an ester of ferulic acid and quinic acid, an ester of ferulic acid and quinic acid comprising a single ferulic acid moiety, an ester of ferulic acid and quinic acid comprising more than one ferulic acid moiety; quinic acid, an ester of quinic acid; tartaric acid, a tartaric acid derivative, an ester of tartaric acid (e.g. caftaric acid or cichoric acid), an ester of a tartaric acid derivative, 3-(3,4-dihydroxyphenyl)lactic acid, a 3-(3,4-dihydroxyphenyl)lactic acid derivative, an ester of 3-(3,4-dihydroxyphenyl)lactic acid (e.g. rosmarinic acid), an ester of a 3-(3,4-dihydroxyphenyl)lactic acid derivative, p-coumaric acid, an ester of p-coumaric acid, an ester of p-coumaric acid and quinic acid, an ester of p-coumaric acid and quinic acid comprising a single p-coumaric acid moiety, an ester of p-coumaric acid and quinic acid comprising more than one p-coumaric acid moiety; sinapic acid, an ester of sinapic acid, an ester of sinapic acid and quinic acid, an ester of sinapic acid and quinic acid comprising a single sinapic acid moiety, an ester of sinapic acid and quinic acid comprising more than one sinapic acid moiety; and 3-O-feruloylquinic acid, 4-O-feruloylquinic acid, 5-O-feruloylquinic acid, 3,4-diferuloylquinic acid, 3,5-diferuloylquinic acid, and 4,5-diferuloylquinic acid.

Caffeic acid has the structure:

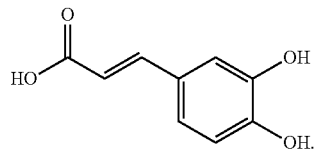 [SMILES: O=C(O)/C=C/c1ccc(O)c(O)c1]

Ferulic acid has the structure:

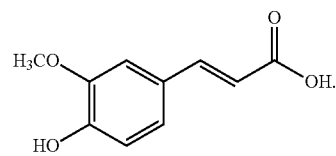 [SMILES: COc1cc(/C=C/C(=O)O)ccc1O]

p-Coumaric acid has the structure:

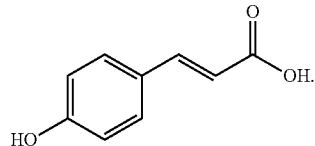 [SMILES: O=C(O)/C=C/c1ccc(O)cc1]

Sinapic acid has the structure:

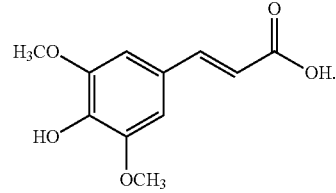

Quinic acid has the structure:

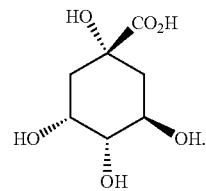 [SMILES: O=C(O)[C@]1(O)C[C@@H](O)[C@@H](O)[C@H](O)C1]

3-(3,4-dihydroxyphenyl)lactic acid has the structure:

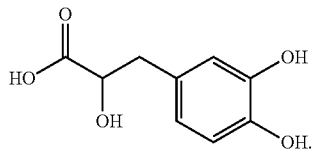

Tartaric acid has the structure:

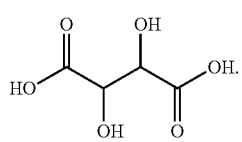

and can be in the D and L forms.

Examples of the esters of the various acids contemplated herein include the ester of caffeic acid and quinic acid, which includes monocaffeoylquinic acids (e.g., chlorogenic acid, neochlorogenic acid, and cryptochlorogenic acid), and dicaffeoylquinic acids (e.g., 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, and 4,5-dicaffeoylquinic acid), and salts thereof:

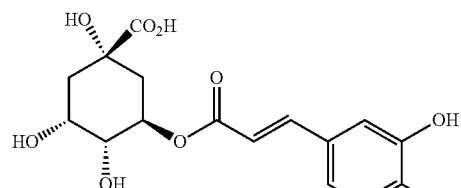

Chlorogenic acid

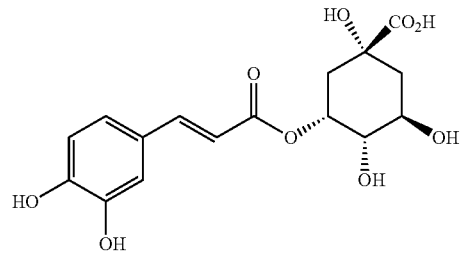

Neochlorogenic acid

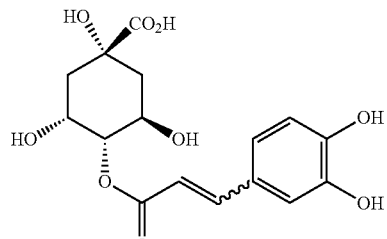

Cryptochlorogenic acid

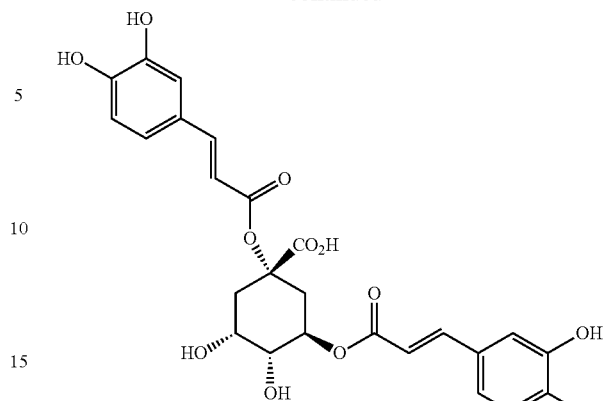

1,5-Dicaffeoylquinic acid

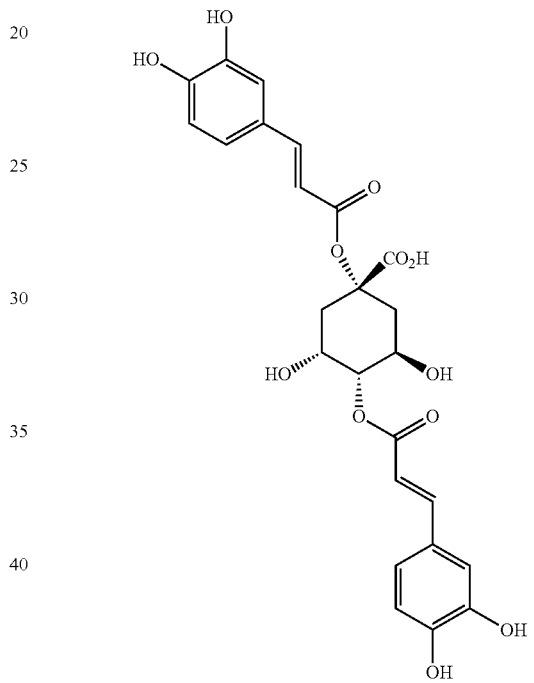

1,4-Dicaffeoylquinic acid

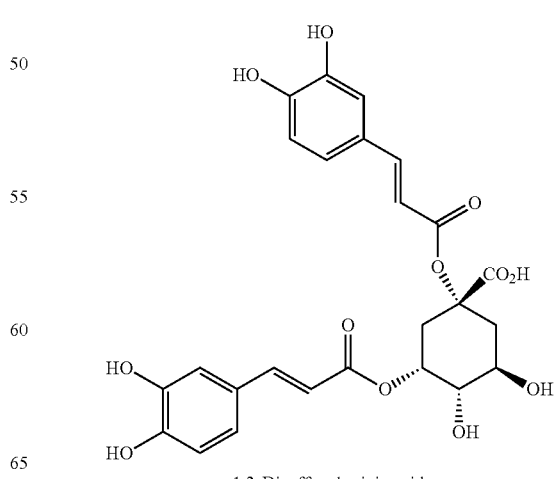

1,3-Dicaffeoylquinic acid

-continued

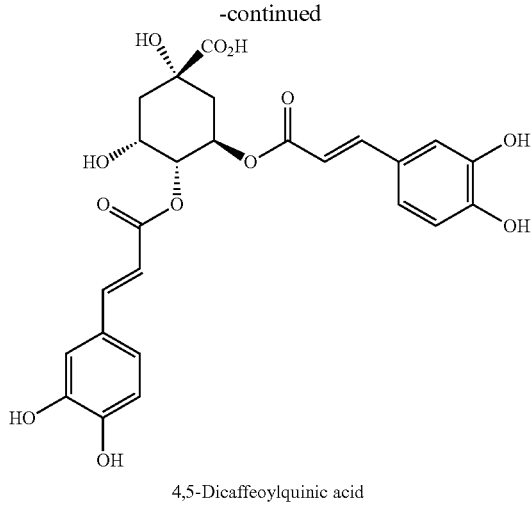

4,5-Dicaffeoylquinic acid

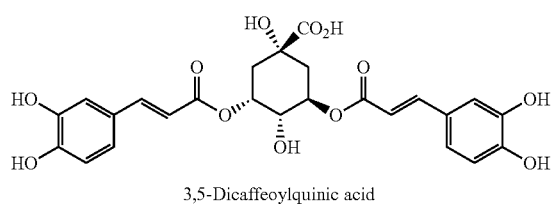

3,5-Dicaffeoylquinic acid

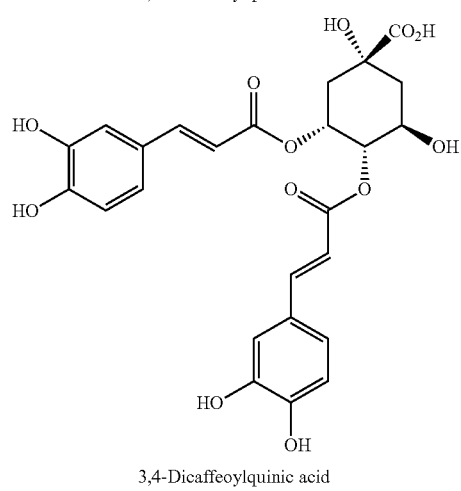

3,4-Dicaffeoylquinic acid with 4,5-dicaffeoylquinic acid, 3,5-dicaffeoylquinic acid, and 3,4-dicaffeoylquinic acid being most prevalent in the compositions contemplated herein and most prevalent in abundant in *Stevia*, yerba mate, globe artichoke, and green coffee bean.

Examples of the esters of the various acids contemplated herein include the ester of caffeic acid and tartaric acid, which includes cichoric acid having the structure:

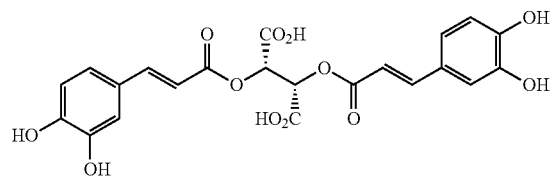 [SMILES: O=C(/C=C/c1ccc(O)c(O)c1)O[C@H](C(=O)O)[C@H](OC(=O)/C=C/c1ccc(O)c(O)c1)C(=O)O]

which has two caffeic acid molecules linked to a tartaric acid core; and caftaric acid having the structure:

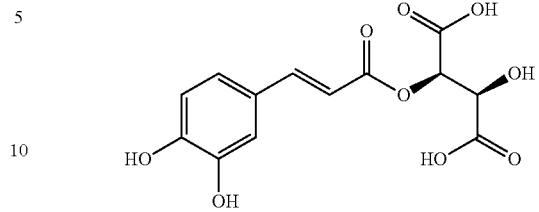

which has one caffeic acid molecule linked to a tartaric acid core.

Examples of the esters of the various acids contemplated herein include the ester of caffeic acid and 3-(3,4-dihydroxyphenyl)lactic acid including, for example, rosmarinic acid, which has the structure:

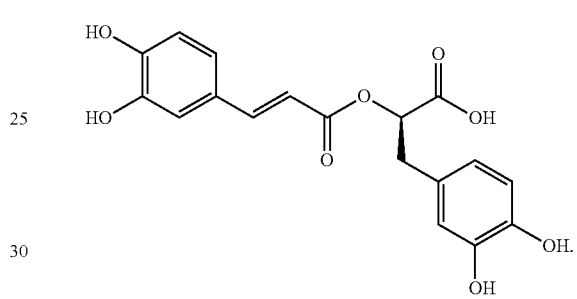

Each of the caffeic acid, monocaffeoylquinic acids, dicaffeoylquinic acids and other surface tension reducing compounds can be considered weak acids and can each exist in at least one of their conjugate acid form, conjugate base form (e.g., in their salt form), and mixed conjugate acid-conjugate base form, wherein a fraction (e.g., mole fraction) of the compounds exist in the conjugate acid form and another fraction exist in the conjugate base form. The fraction of conjugate acid form to conjugate base form for the caffeic acid, monocaffeoylquinic acids, dicaffeoylquinic acids, and other surface tension reducing compounds will depend on various factors, including the pKa of each compound and the pH of the composition.

Examples of salts of caffeic acid, monocaffeoylquinic acids, dicaffeoylquinic acids, and other surface tension reducing compounds include, but are not limited to, quaternary ammonium, sodium, potassium, lithium, magnesium, and calcium salts of caffeic acid, monocaffeoylquinic acids, dicaffeoylquinic acids, monoferuloylquinic acids, and diferuloylquinic acids, and other surface tension reducing compounds and the like.

In some aspects, the surface tension reducing compound can be enriched for one or more of caffeic acid, monocaffeoylquinic acids, and dicaffeoylquinic acids. The term "enriched" refers to an increase in an amount of one of caffeic acid, monocaffeoylquinic acids, and dicaffeoylquinic acids relative to one or more other compounds that are present in the surface tension reducing compound. A surface tension reducing compound that is enriched for one or more of caffeic acid, monocaffeoylquinic acids, and dicaffeoylquinic acids can reduce surface tension of the steviol glycoside composition with reduced surface tension.

In some aspects, a surface tension reducing compound enriched for one or more dicaffeoylquinic acids can reduce surface tension of the steviol glycoside composition with reduced surface tension. A surface tension reducing compound that is enriched for dicaffeoylquinic acids can comprise 10% or more, 15% or more, 20% or more, 25% or more, 30% or more, 35% or more, 40% or more, 45% or more, or 50% or more, 60% or more, 70% or more, or 80% or more, or 90% or more dicaffeoylquinic acids. In other aspects, a surface tension reducing compound that is enriched for dicaffeoylquinic acids can comprise 10% or more, 15% or more, 20% or more, 25% or more, 30% or more, 35% or more, 40% or more, 45% or more, or 50% or more, 60% or more, 70% or more, or 80% or more, or 90% or more of a combination of one or more of 1,3-dicaffeoylquinic acid, 1,4-dicaffeoylquinic acid, 1,5-dicaffeoylquinic acid, 3,4-dicaffeoylquinic, 3,5-dicaffeoylquinic acid, and 4,5-dicaffeoylquinic acid, and salts thereof.

The amount of surface tension reducing compound in the steviol glycoside composition with reduced surface tension can vary. Surface tension reducing compound can be present in the steviol glycoside composition with reduced surface tension in any amount desired for the particular use. For example, surface tension reducing compound can be present in the steviol glycoside composition with reduced surface tension at from about 1 ppm to about 1000 ppm, from about 1 ppm to about 10000 ppm, from about 1 ppm to about 100000 ppm, from about 1 ppm to about 200000 ppm, or from about 1 ppm to about 300000 ppm. In some aspects, surface tension reducing compound can be present in the steviol glycoside composition with reduced surface tension at about 100 ppm to about 5000 ppm, about 200 ppm to about 5000 ppm, 300 ppm to about 5000 ppm, 400 ppm to about 5000 ppm, 500 ppm to about 5000 ppm, 600 ppm to about 5000 ppm, 700 ppm to about 5000 ppm, 800 ppm to about 5000 ppm, 900 ppm to about 5000 ppm, or 1000 ppm to about 5000 ppm. In some aspects, surface tension reducing compound can be present in the steviol glycoside composition with reduced surface tension at from about 1000 ppm to about 5000 ppm, about 2000 ppm to about 5000 ppm, about 3000 ppm to about 5000 ppm, or about 4000 ppm to about 5000 ppm. In some aspects, surface tension reducing compound can be present in the steviol glycoside composition with reduced surface tension at or greater than about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, or 100000 ppm. In some aspects, surface tension reducing compound can be present in the steviol glycoside composition with reduced surface tension at or greater than about 200000 ppm. In some aspects, surface tension reducing compound can be present in the steviol glycoside composition with reduced surface tension at or greater than about 300000 ppm. Unless otherwise expressly stated, ppm is on a by weight basis.

The amount of an individual surface tension reducing compound species in the steviol glycoside composition with reduced surface tension can vary. For example, an individual surface tension reducing compound species can be present in the steviol glycoside composition with reduced surface tension at a concentration from about 1 ppm to about 1000 ppm, from about 1 ppm to about 10000 ppm, from about 1 ppm to about 100000 ppm, from about 1 ppm to about 200000 ppm, or from about 1 ppm to about 300000 ppm. In some aspects, an individual surface tension reducing compound species can be present in the steviol glycoside composition with reduced surface tension at a concentration from about 100 ppm to about 5000 ppm, about 200 ppm to about 5000 ppm, 300 ppm to about 5000 ppm, 400 ppm to about 5000 ppm, 500 ppm to about 5000 ppm, 600 ppm to about 5000 ppm, 700 ppm to about 5000 ppm, 800 ppm to about 5000 ppm, 900 ppm to about 5000 ppm, or 1000 ppm to about 5000 ppm. In some aspects, an individual surface tension reducing compound species can be present in the steviol glycoside composition with reduced surface tension at a concentration from about 1000 ppm to about 5000 ppm, about 2000 ppm to about 5000 ppm, about 3000 ppm to about 5000 ppm, or about 4000 ppm to about 5000 ppm. In some aspects, an individual surface tension reducing compound species can be present in the steviol glycoside composition with reduced surface tension at a concentration of or greater than about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, or 100000 ppm. In some aspects, an individual surface tension reducing compound species can be present in the steviol glycoside composition with reduced surface tension at a concentration of or greater than about 200000 ppm. In some aspects, an individual surface tension reducing compound species can be present in the steviol glycoside composition with reduced surface tension at a concentration of or greater than about 300000 ppm. Unless otherwise expressly stated, ppm is on a by weight basis The amount of an individual surface tension reducing compound species in the steviol glycoside composition with reduced surface tension can vary. For example, dicaffeoylquinic acid can be present in the steviol glycoside composition with reduced surface tension at a concentration from about 1 ppm to about 1000 ppm, from about 1 ppm to about 10000 ppm, from about 1 ppm to about 100000 ppm, from about 1 ppm to about 200000 ppm, or from about 1 ppm to about 300000 ppm. In some aspects, dicaffeoylquinic acid can be present in the steviol glycoside composition with reduced surface tension at a concentration from about 100 ppm to about 5000 ppm, about 200 ppm to about 5000 ppm, 300 ppm to about 5000 ppm, 400 ppm to about 5000 ppm, 500 ppm to about 5000 ppm, 600 ppm to about 5000 ppm, 700 ppm to about 5000 ppm, 800 ppm to about 5000 ppm, 900 ppm to about 5000 ppm, or 1000 ppm to about 5000 ppm. In some aspects, dicaffeoylquinic acid can be present in the steviol glycoside composition with reduced surface tension at a concentration from about 1000 ppm to about 5000 ppm, about 2000 ppm to about 5000 ppm, about 3000 ppm to about 5000 ppm, or about 4000 ppm to about 5000 ppm. In some aspects, dicaffeoylquinic acid can be present in the steviol glycoside composition with reduced surface tension at a concentration of or greater than about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, or 100000 ppm. In some aspects, dicaffeoylquinic acid can be present in the steviol glycoside composition with reduced surface tension at a concentration of or greater than about 200000 ppm. In some aspects, dicaffeoylquinic acid can be present in the steviol glycoside composition with reduced surface tension at a concentration of or greater than about 300000 ppm. Unless otherwise expressly stated, ppm is on a by weight basis.

In some aspects, the surface tension reducing compound may be isolated from botanical sources. Various botanical sources comprise surface tension reducing compounds and surface tension reducing compounds can be isolated from these plants. Some examples of botanical sources from which surface tension reducing compounds can be isolated include eucommoia ulmoides, honeysuckle, *Nicotiana benthamiana*, globe artichoke, cardoon, *Stevia, Stevia Rebaudiana*, monkfruit, coffee, coffee beans, green coffee beans, tea, white tea, yellow tea, green tea, oolong tea, black tea, red tea, post-fermented tea, bamboo, heather, sunflower, blueberries, cranberries, bilberries, grouseberries, whortleberry, lingonberry, cowberry, huckleberry, grapes, chicory, eastern purple coneflower, echinacea, Eastern pellitory-of-the-wall, Upright pellitory, Lichwort, Greater celandine, Tetterwort, Nipplewort, Swallowwort, Bloodroot, Common nettle, Stinging nettle, Potato, Potato leaves, Eggplant, Aubergine, Tomato, Cherry tomato, Bitter apple, Thorn apple, Sweet potato, apple, Peach, Nectarine, Cherry, Sour cherry, Wild cherry, Apricot, Almond, Plum, Prune, Holly, Yerba mate, Mate, *Ilex paraguariensis*, Guayusa, Yaupon Holly, Kuding, Guarana, Cocoa, Cocoa bean, Cacao, Cacao bean, Kola nut, Kola tree, Cola nut, Cola tree, Hornwort, Ostrich fern, Oriental ostrich fern, Fiddlehead fern, Shuttlecock fern, Oriental ostrich fern, Asian royal fern, Royal fern, Bracken, Brake, Common bracken, Eagle fern, Eastern brakenfern, dandelion, algae, seagrasses, Clove, Cinnamon, Indian bay leaf, Nutmeg, Bay laurel, Bay leaf, Basil, Great basil, Saint-Joseph's-wort, Thyme, Sage, Garden sage, Common sage, Culinary sage, Rosemary, Oregano, Wild marjoram, Marjoram, Sweet marjoram, Knotted marjoram, Pot marjoram, Dill, Anise, Star anise, Fennel, Florence fennel, Tarragon, Estragon, Mugwort, Licorice, Liquorice, Soy, Soybean, Soyabean, Soya vean, Wheat, Common wheat, Rice, Canola, Broccoli, Cauliflower, Cabbage, Bok choy, Kale, Collard greens, Brussels sprouts, Kohlrabi, Winter's bark, Elderflower, Assa-Peixe, Greater burdock, Valerian, and Chamomile. In some aspects, the botanical source is yerba mate, chicory, rosemary, and/or *Stevia*.

Some plants may produce surface tension reducing compounds that are enriched for one or more of caffeic acid, monocaffeoylquinic acids, and dicaffeoylquinic acids and can reduce surface tension of the steviol glycoside composition with reduced surface tension. For example, surface tension reducing compounds isolated from yerba mate plant (*Ilex paraguariensis*) are enriched for dicaffeoylquinic acids and can reduce surface tension of the steviol glycoside composition with reduced surface tension. In other aspects, surface tension reducing compounds isolated from yerba mate plant that are enriched for dicaffeoylquinic acids can comprise 10% or more, 15% or more, 20% or more, 25% or more, 30% or more, 35% or more, 40% or more, 45% or more, or 50% or more, 60% or more, 70% or more, or 80% or more, or 90% or more of a combination of one or more of 1,3-dicaffeoylquinic acid, 1,4-dicaffeoylquinic acid, 1,5-dicaffeoylquinic acid, 3,4-dicaffeoylquinic, 3,5-dicaffeoylquinic acid, and 4,5-dicaffeoylquinic acid, and salts thereof. For example, surface tension reducing compounds isolated from other plants can be enriched for dicaffeoylquinic acids and can reduce surface tension of the steviol glycoside composition with reduced surface tension. In other aspects, surface tension reducing compounds isolated from other plants that are enriched for dicaffeoylquinic acids can comprise 10% or more, 15% or more, 20% or more, 25% or more, 30% or more, 35% or more, 40% or more, 45% or more, or 50% or more, 60% or more, 70% or more, or 80% or more, or 90% or more of a combination of one or more of 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, and 4,5-dicaffeoylquinic acid, and salts thereof.

In some aspects, the surface tension reducing compound can be a blend of surface tension reducing compound isolated from more than one botanical source. The surface tension reducing compound can be a blend of surface tension reducing compound isolated from more than one botanical source.

In some aspects, the ratio of surface tension reducing compound to steviol glycoside in the steviol glycoside composition with reduced surface tension can vary. The ratio of surface tension reducing compound to steviol glycoside in the steviol glycoside composition with reduced surface tension can be in any amount effective to reduce surface tension. For example, the ratio of surface tension reducing compound to steviol glycoside can be from about 0.1:1 to 10:1. In some aspects, the ratio of surface tension reducing compound to steviol glycoside can be in the range of about 0.1:1 to 5:1, about 0.5:1 to 4:1, or about 1:1 to 3:1. In other aspects, the ratio of surface tension reducing compound to steviol glycoside is about 1:1, 2:1, 3:1, 4:1, 5:1, 6:1, 7:1, 8:1, 9:1, or 10:1. In other aspects, the ratio of surface tension reducing compound to steviol glycoside is about 0.1:1, 0.2:1, 0.3:1, 0.4:1, 0.5:1, 0.6:1, 0.7:1, 0.8:1, or 0.9:1. In other aspects, the ratio of surface tension reducing compound to steviol glycoside is about 1.1:1, 1.2:1, 1.3:1, 1.4:1, 1.5:1, 1.6:1, 1.7:1, 1.8:1, or 1.9:1. In other aspects, the ratio of surface tension reducing compound to steviol glycoside is about 2.1:1, 2.2:1, 2.3:1, 2.4:1, 2.5:1, 2.6:1, 2.7:1, 2.8:1, or 2.9:1. In other aspects, the ratio of surface tension reducing compound to steviol glycoside is about 3.1:1, 3.2:1, 3.3:1, 3.4:1, 3.5:1, 3.6:1, 3.7:1, 3.8:1, or 3.9:1. In other aspects, the ratio of surface tension reducing compound to steviol glycoside is about 4.1:1, 4.2:1, 4.3:1, 4.4:1, 4.5:1, 4.6:1, 4.7:1, 4.8:1, or 4.9:1.

In some aspects, the steviol glycoside composition with reduced surface tension can comprise an surface tension reducing compound in an amount effective to reduce the surface tension compared to a steviol glycoside solution without an surface tension reducing compound. This reduction in surface tension can be at least 1%, at least 2%, at least 3%, at least 4%, at least 5%, at least 6%, at least 7%, at least 8%, at least 9%, at least 10%, at least 11%, at least 12%, at least 13%, at least 14%, or at least 15%. The reduction in surface tension can be at least 20%, 30%, 40%, 50%, 60%, 70%, 80%, or 90%. The reduction in surface tension can refer to a reduction in initial surface tension of the steviol glycoside composition with reduced surface tension comprising an surface tension reducing compound compared to similar a similar steviol glycoside composition without the surface tension reducing compound. The reduction in surface tension can also refer to a reduction in surface tension of the steviol glycoside composition with reduced surface tension comprising an surface tension reducing compound compared to similar a similar steviol glycoside composition without the surface tension reducing compound over time. The reduction in surface tension can also refer to a reduction in surface tension of the steviol glycoside composition with reduced surface tension comprising an surface tension reducing compound compared to similar a similar steviol glycoside composition without the surface tension reducing compound at equilibrium.

In some aspects, surface tension can be measured by various methods known to the skilled person. A tensiometer can be used to measure surface tension by various methods, including, but not limited to Du Noüy ring method, Du Noüy-Padday method, Wilhelmy plate method, spinning drop method, pendant drop method, bubble pressure method, drop volume method, capillary rise method, stalagmometric method, sessile drop method, vibrational frequency of levitated drops, resonant oscillations of spherical and hemispherical liquid drop.

In some aspects, the steviol glycoside composition with reduced surface tension can comprise additives, flavors, colors, fillers, bulking agents, and other additives including, but not limited to, carbohydrates, polyols, amino acids and their corresponding salts, poly-amino acids and their corresponding salts, sugar acids and their corresponding salts, nucleotides, organic acids, inorganic acids, organic salts including organic acid salts and organic base salts, inorganic salts, bitter compounds, flavorants and flavoring ingredients, astringent compounds, proteins or protein hydrolysates, surfactants, emulsifiers, weighing agents, gums, antioxidants, colorants, flavonoids, alcohols, polymers and combinations thereof, caffeine, quinine, urea, bitter orange oil, naringin, quassia, and salts thereof, vanillin, vanilla extract, mango extract, cinnamon, citrus, coconut, ginger, viridiflorol, almond, menthol (including menthol without mint), cola, lemon, lime, root beer, sarsaparilla, orange, grape skin extract, grape seed extract, chitosan, pectin, pectic, pectinic, polyuronic, polygalacturonic acid, starch, food hydrocolloid or crude extracts thereof (e.g., gum acacia Senegal (Fibergum™), gum acacia seyal, carageenan), poly-L-lysine (e.g., poly-L-a-lysine or poly-L-e-lysine), poly-L-ornithine (e.g., poly-L-a-ornithine or poly-L-e-ornithine), polypropylene glycol, polyethylene glycol, poly(ethylene glycol methyl ether), polyarginine, polyaspartic acid, polyglutamic acid, polyethylene imine, alginic acid, sodium alginate, propylene glycol alginate, and sodium polyethyleneglycolalginate, sodium hexametaphosphate and its salts, and other cationic polymers and anionic polymers. In some aspects, one or more additives is present in the steviol glycoside composition with reduced surface tension at about 0.1 ppm to about 4,000 ppm.

An example of a steviol glycoside composition with reduced surface tension includes a beverage concentrate solution with reduced surface tension comprising a steviol glycoside and an surface tension reducing compound in an amount effective to reduce surface tension by at least 10% during at least six-fold dilution of the concentrate solution. Another example of a beverage concentrate solution with reduced surface tension comprises a steviol glycoside and a surface tension reducing compound in an amount effective to reduce surface tension by at least 1%, at least 2%, at least 3%, at least 4%, at least 5%, at least 6%, at least 7%, at least 8%, at least 9%, at least 10%, at least 11%, at least 12%, at least 13%, at least 14%, or at least 15% during at least six-fold dilution of the concentrate solution. Another example of a beverage concentrate solution with reduced surface tension comprises a steviol glycoside and an surface tension reducing compound in an amount effective to reduce surface tension by at least 20%, 30%, 40%, 50%, 60%, 70%, 80%, or 90% during at least six-fold dilution of the concentrate solution.

In some aspects, the beverage concentrate solution with reduced surface tension comprises a throw syrup for preparing a carbonated soda drink. The beverage concentrate solution with reduced surface tension can also comprise other drink concentrates used to prepare beverages. In other aspects, the beverage concentrate solution with reduced surface tension comprises a throw syrup for preparing a carbonated soda drink in a soda fountain. In some aspects, the beverage concentrate solution with reduced surface tension comprises an aqueous solution. The aqueous solution can comprise primarily water. The aqueous solution can also comprise a buffer such as a citrate/phosphate buffer. The citrate/phosphate buffer can have a pH of 1.5 to 4.

In some aspects, the beverage concentrate solution with reduced surface tension is diluted before use as a beverage. For example, the beverage concentrate solution with reduced surface tension can be diluted in a soda fountain by diluting with a stream of carbonated water as the beverage is dispensed. This diluting of the beverage concentrate solution with reduced surface tension with the stream of carbonated water can dilute the beverage concentrate solution with reduced surface tension by about 6 to 7 times. The surface tension reducing compound can be present in the beverage concentrate solution with reduced surface tension in an effective amount to reduce surface tension during this dilution as the beverage is dispensed. In some aspects, the beverage concentrate solution with reduced surface tension comprises a total steviol glycoside concentration of about 2400 to 4200 ppm. In other aspects, the beverage concentrate solution with reduced surface tension comprises an surface tension reducing compound concentration of 1800 to 5400 ppm. In some aspects, the beverage concentrate solution with reduced surface tension comprises an surface tension reducing compound concentration of 1800 to 1000 ppm.

The beverage concentrate solution with reduced surface tension can also be diluted by mixing with water (or carbonated water) before use as a beverage by a consumer. For example, the beverage concentrate solution with reduced surface tension can be diluted with water or other similar solution such as carbonated water and then mixed. The surface tension reducing compound can be present in the beverage concentrate solution with reduced surface tension in an effective amount to reduce surface tension during the dilution and mixing of the beverage. In some aspects, the beverage concentrate solution with reduced surface tension comprises a total steviol glycoside concentration of about 2400 to 4200 ppm. In other aspects, the beverage concentrate solution with reduced surface tension comprises an surface tension reducing compound concentration of about 1800 to 5400 ppm. In other aspects, the beverage concentrate solution with reduced surface tension comprises an surface tension reducing compound concentration of about 1800 to 1000 ppm.

An example of a steviol glycoside composition with reduced surface tension comprises a dry admixture of steviol glycoside and surface tension reducing compound, wherein an aqueous solution prepared from the dry admixture comprises reduced surface tension compared to an aqueous solution prepared from a dry admixture of steviol glycoside without surface tension reducing compound. In some aspects, surface tension is reduced by at least 10%. In other aspects, surface tension is reduced by at least 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65%, 70%, 75%, 80%, 85%, 90%, 95% or more. In some aspects, initial surface tension is reduced by at least 10%. In other aspects, initial surface tension is reduced by at least 10%, 15%, 20%, 25%, 30%, 35%, 40%, 45%, 50%, 55%, 60%, 65%, 70%, 75%, 80%, 85%, 90%, 95% or more. In some aspects, surface tension decreases more quickly over time by at least 10%. In other aspects, surface tension decreases more quickly over time by at least 10%, 15%, 20%, 25%, 30%, 35%, 40%, 45%, 50%, 55%, 60%, 65%, 70%, 75%, 80%, 85%, 90%, 95% or more.

In some aspects, an example of a steviol glycoside composition with reduced surface tension comprises a dry admixture of steviol glycoside and surface tension reducing compound, wherein an aqueous solution prepared from the dry admixture has a reduced surface tension compared to a steviol glycoside solution without surface tension reducing compound. This reduction in surface tension can be at least 1%, at least 2%, at least 3%, at least 4%, at least 5%, at least 6%, at least 7%, at least 8%, at least 9%, at least 10%, at least 11%, at least 12%, at least 13%, at least 14%, or at least 15%. The reduction in surface tension can be at least 20%, 30%, 40%, 50%, 60%, 70%, 80%, or 90%.

In some aspects, the dry admixture is prepared with an aqueous solution comprising primarily water. The aqueous solution can also be buffered with any suitable buffering system, including, but not limited to, one or more buffers such as a phosphate, a citrate, ascorbate, lactate, acetate, and the like. The buffer can comprise 1-1000 mM of the anion component. In other aspects, the aqueous solution comprises a citrate/phosphate buffer. In some aspects, citrate/phosphate buffer can have a pH of 2 to 4.

The amounts of steviol glycoside in the dry admixture and the surface tension reducing compound can be expressed in relation to one another, or to the total amount of steviol glycosides (TSG), such as a weight percentage of the total amount of steviol glycosides (TSG), or to the total amount of surface tension reducing compound, or a ratio, or range of ratios, expressed as a weight percent, or molar percent.

The dry admixture can include one or more steviol glycosides. In some aspects, the term steviol glycoside refers to Rebaudioside A (Reb A) (CAS #58543-16-1), Rebaudioside B (Reb B) (CAS #58543-17-2), Rebaudioside C (Reb C) (CAS #63550-99-2), Rebaudioside D (Reb D) (CAS #63279-13-0), Rebaudioside E (Reb E) (CAS #63279-14-1), Rebaudioside F (Reb F) (CAS #438045-89-7), Rebaudioside M (Reb M) (CAS #1220616-44-3), Rubusoside (CAS #63849-39-4), Dulcoside A (CAS #64432-06-0), Rebaudioside I (Reb I) (MassBank Record: FU000332), Rebaudioside Q (Reb Q), Rebaudioside O (Reb O), Rebaudioside N (Reb N) (CAS #1220616-46-5), 1,2-Stevioside (CAS #57817-89-7), 1,3-Stevioside (Reb G), Steviol-1,2-Bioside (MassBank Record: FU000299), Steviol-1,3-Bioside, Steviol-13-O-glucoside (13-SMG), Steviol-19-O-glucoside (19-SMG), and steviol glycoside having 1, 2, 3, 4, 5, 6, 7, 8, 9, 10 or sugar additions (e.g., glucose, rhamnose, and/or xylose), and isomers thereof. See FIG. 1; see also, Steviol Glycosides Chemical and Technical Assessment 69th JECFA, 2007, prepared by Harriet Wallin, Food Agric. Org.

In some aspects, the dry admixture can include rebaudioside A. For example, the dry admixture can include blends of rebaudioside A and one or more other steviol glycosides. An example of a blend of rebaudioside A with one or more other steviol glycosides comprises 60% or more rebaudioside A (RA60). Another example of a blend of rebaudioside A with one or more other steviol glycosides comprises 80% or more rebaudioside A (RA80). Another example of a blend of rebaudioside A with one or more other steviol glycosides comprises 95% or more rebaudioside A (RA95). In other aspects, steviol glycosides can include blends of one or more of RebA, RebB, RebC, RebD, RebE, RebF, RebM, rubusoside, dulcoside A, RebI, RebQ, 1,2 steviosioside, 1,3 stevioside, steviol-1,2-bioside, steviol-1,3-bioside, 13-SMG, 19-SMG, a tri-glycosylated steviol glycoside, a tetra-glycosylated steviol glycoside, a penta-glycosylated steviol glycoside, a hexa-glycosylated steviol glycoside, a hepta-glycosylated steviol glycoside, and isomers thereof.

In some aspects, the dry admixture can comprise blends of rebaudioside M and rebaudioside D. For example, rebaudioside M and rebaudioside D can be present in the blend in a total amount of about 80% (wt) or greater, 90% (wt) or greater, or 95% (wt) or greater, of a total amount steviol glycosides (TSG) in the composition. Rebaudioside M can be the predominant steviol glycoside in the blend, and can be present, for example, in an amount in the range of about 50% to about 95%, about 70% to about 90%, or about 75% to about 85% of the total amount steviol glycosides (TSG) in the composition. Rebaudioside D can be in an amount less than Rebaudioside M, such as in an amount in the range of about 5% to about 25%, about 10% to about 20%, or about 10% to about 15% of the total amount of steviol glycosides (TSG) in the composition.

The amount of steviol glycosides in the dry admixture can vary. Steviol glycosides can be present in the dry admixture in any amount desired for the particular use. For example, steviol glycosides can be present in the dry admixture at a total concentration from about 1 ppm to about 1000 ppm, from about 1 ppm to about 10000 ppm, from about 1 ppm to about 100000 ppm, from about 1 ppm to about 200000 ppm, or from about 1 ppm to about 300000 ppm. In some aspects, steviol glycosides can be present in the dry admixture at a total concentration from about 100 ppm to about 5000 ppm, about 200 ppm to about 5000 ppm, 300 ppm to about 5000 ppm, 400 ppm to about 5000 ppm, 500 ppm to about 5000 ppm, 600 ppm to about 5000 ppm, 700 ppm to about 5000 ppm, 800 ppm to about 5000 ppm, 900 ppm to about 5000 ppm, or 1000 ppm to about 5000 ppm. In some aspects, steviol glycosides can be present in the dry admixture at a total concentration from about 1000 ppm to about 5000 ppm, about 2000 ppm to about 5000 ppm, about 3000 ppm to about 5000 ppm, or about 4000 ppm to about 5000 ppm. In some aspects, steviol glycosides can be present in the dry admixture at a total concentration of or greater than about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, or 100000 ppm. In some aspects, steviol glycosides can be present in the dry admixture at a total concentration of or greater than about 200000 ppm. In some aspects, steviol glycosides can be present in the dry admixture at a total concentration of or greater than about 300000 ppm. Unless otherwise expressly stated, ppm is on a by weight basis.

The amount of steviol glycoside in the dry admixture can vary. For example, an individual steviol glycoside can be present in the dry admixture at a concentration of about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, or more.

The amount of an individual steviol glycoside species in the dry admixture can vary. For example, an individual steviol glycoside species can be present in the dry admixture at a concentration from about 1 ppm to about 1000 ppm, from about 1 ppm to about 10000 ppm, from about 1 ppm to about 100000 ppm, from about 1 ppm to about 200000 ppm, or from about 1 ppm to about 300000 ppm. In some aspects, an individual steviol glycoside species can be present in the dry admixture at a concentration from about 100 ppm to about 5000 ppm, about 200 ppm to about 5000 ppm, 300 ppm to about 5000 ppm, 400 ppm to about 5000 ppm, 500 ppm to about 5000 ppm, 600 ppm to about 5000 ppm, 700 ppm to about 5000 ppm, 800 ppm to about 5000 ppm, 900 ppm to about 5000 ppm, or 1000 ppm to about 5000 ppm. In some aspects, an individual steviol glycoside species can be present in the dry admixture at a concentration from about 1000 ppm to about 5000 ppm, about 2000 ppm to about 5000 ppm, about 3000 ppm to about 5000 ppm, or about 4000 ppm to about 5000 ppm. In some aspects, an individual steviol glycoside species can be present in the dry admixture at a concentration of or greater than about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, or 100000 ppm. In some aspects, an individual steviol glycoside species can be present in the dry admixture at a concentration of or greater than about 200000 ppm. In some aspects, an individual steviol glycoside species can be present in the dry admixture at a concentration of or greater than about 300000 ppm. Unless otherwise expressly stated, ppm is on a by weight basis The amount of an individual steviol glycoside in the dry admixture can vary. For example, an individual steviol glycoside can be present in the dry admixture at a concentration of about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, or more.

The amount of an individual steviol glycoside species in the dry admixture composition can vary. For example, RebA can be present in the dry admixture at a concentration from about 1 ppm to about 1000 ppm, from about 1 ppm to about 10000 ppm, from about 1 ppm to about 100000 ppm, from about 1 ppm to about 200000 ppm, or from about 1 ppm to about 300000 ppm. In some aspects, RebA can be present in the dry admixture at a concentration from about 100 ppm to about 5000 ppm, about 200 ppm to about 5000 ppm, 300 ppm to about 5000 ppm, 400 ppm to about 5000 ppm, 500 ppm to about 5000 ppm, 600 ppm to about 5000 ppm, 700 ppm to about 5000 ppm, 800 ppm to about 5000 ppm, 900 ppm to about 5000 ppm, or 1000 ppm to about 5000 ppm. In some aspects, RebA can be present in the dry admixture at a concentration from about 1000 ppm to about 5000 ppm, about 2000 ppm to about 5000 ppm, about 3000 ppm to about 5000 ppm, or about 4000 ppm to about 5000 ppm. In some aspects, RebA can be present in the dry admixture at a concentration of or greater than about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, or 100000 ppm. In some aspects, RebA can be present in the dry admixture at a concentration of or greater than about 200000 ppm. In some aspects, RebA can be present in the dry admixture at a concentration of or greater than about 300000 ppm. Unless otherwise expressly stated, ppm is on a by weight basis.

The amount of an individual steviol glycoside species in the dry admixture can vary. For example, RebM can be present in the dry admixture at a concentration from about 1 ppm to about 1000 ppm, from about 1 ppm to about 10000 ppm, from about 1 ppm to about 100000 ppm, from about 1 ppm to about 200000 ppm, or from about 1 ppm to about 300000 ppm. In some aspects, RebM can be present in the dry admixture at a concentration from about 100 ppm to about 5000 ppm, about 200 ppm to about 5000 ppm, 300 ppm to about 5000 ppm, 400 ppm to about 5000 ppm, 500 ppm to about 5000 ppm, 600 ppm to about 5000 ppm, 700 ppm to about 5000 ppm, 800 ppm to about 5000 ppm, 900 ppm to about 5000 ppm, or 1000 ppm to about 5000 ppm. In some aspects, RebM can be present in the dry admixture at a concentration from about 1000 ppm to about 5000 ppm, about 2000 ppm to about 5000 ppm, about 3000 ppm to about 5000 ppm, or about 4000 ppm to about 5000 ppm. In some aspects, RebM can be present in the dry admixture at a concentration of or greater than about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, or 100000 ppm. In some aspects, RebM can be present in the dry admixture at a concentration of or greater than about 200000 ppm. In some aspects, RebM can be present in the dry admixture at a concentration of or greater than about 300000 ppm. Unless otherwise expressly stated, ppm is on a by weight basis.

In some aspects, the dry admixture comprises steviol glycoside at 1%, 2%, 3%, 4%, 5%, 6%, 7%, 8%, 9% 10% or more by weight. The dry admixture can comprise steviol glycoside at 11%, 12%, 13%, 14%, 15%, 16%, 17%, 18%, 19%, 20% or more by weight. The dry mixture can comprise steviol glycoside at 21%, 22%, 23%, 24%, 25%, 26%, 27%, 28%, 29%, 30% or more by weight. The dry mixture can comprise steviol glycoside at 35%, 40%, 45%, 50%, 55%, 60%, 65%, 70%, 75%, 80%, 85%, 90% or more by weight.

The amount of surface tension reducing compound in the dry admixture can vary. Surface tension reducing compound can be present in the dry admixture in any amount desired for the particular use. For example, surface tension reducing compound can be present in the dry admixture at about 1 ppm to about 1000 ppm, from about 1 ppm to about 10000 ppm, from about 1 ppm to about 100000 ppm, from about 1 ppm to about 200000 ppm, or from about 1 ppm to about 300000 ppm. In some aspects, surface tension reducing compound can be present in the dry admixture at about 100 ppm to about 5000 ppm, about 200 ppm to about 5000 ppm, 300 ppm to about 5000 ppm, 400 ppm to about 5000 ppm, 500 ppm to about 5000 ppm, 600 ppm to about 5000 ppm, 700 ppm to about 5000 ppm, 800 ppm to about 5000 ppm, 900 ppm to about 5000 ppm, or 1000 ppm to about 5000 ppm. In some aspects, surface tension reducing compound can be present in the dry admixture at about 1000 ppm to about 5000 ppm, about 2000 ppm to about 5000 ppm, about 3000 ppm to about 5000 ppm, or about 4000 ppm to about 5000 ppm. In some aspects, surface tension reducing compound can be present in the dry admixture at or greater than about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, or 100000 ppm. In some aspects, surface tension reducing compound can be present in the dry admixture at or greater than about 200000 ppm. In some aspects, surface tension reducing compound can be present in the dry admixture at or greater than about 300000 ppm. Unless otherwise expressly stated, ppm is on a by weight basis.

The amount of surface reducing compound in the dry admixture can vary. For example, an individual steviol glycoside can be present in the dry admixture at a concentration of about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, or more.

The amount of an individual surface tension reducing compound species in the dry admixture composition can vary. For example, an individual surface tension reducing compound can be present in the dry admixture at a concentration from about 1 ppm to about 1000 ppm, from about 1 ppm to about 10000 ppm, from about 1 ppm to about 100000 ppm, from about 1 ppm to about 200000 ppm, or from about 1 ppm to about 300000 ppm. In some aspects, an individual surface tension reducing compound species can be present in the dry admixture at a concentration from about 100 ppm to about 5000 ppm, about 200 ppm to about 5000 ppm, 300 ppm to about 5000 ppm, 400 ppm to about 5000 ppm, 500 ppm to about 5000 ppm, 600 ppm to about 5000 ppm, 700 ppm to about 5000 ppm, 800 ppm to about 5000 ppm, 900 ppm to about 5000 ppm, or 1000 ppm to about 5000 ppm. In some aspects, an individual surface tension reducing compound species can be present in the dry admixture at a concentration from about 1000 ppm to about 5000 ppm, about 2000 ppm to about 5000 ppm, about 3000 ppm to about 5000 ppm, or about 4000 ppm to about 5000 ppm. In some aspects, an individual surface tension reducing compound species can be present in the dry admixture at a concentration of or greater than about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, or 100000 ppm. In some aspects, an individual surface tension reducing compound species can be present in the dry admixture at a concentration of or greater than about 200000 ppm. In some aspects, an individual surface tension reducing compound species can be present in the dry admixture at a concentration of or greater than about 300000 ppm. Unless otherwise expressly stated, ppm is on a by weight basis In some aspects, the surface tension reducing compound in the dry admixture can be enriched for one or more of caffeic acid, monocaffeoylquinic acids, and dicaffeoylquinic acids. The term "enriched" refers to an increase in an amount of one of caffeic acid, monocaffeoylquinic acids, and dicaffeoylquinic acids relative to one or more other compounds that are present in the surface tension reducing compound. An surface tension reducing compound that is enriched for one or more of caffeic acid, monocaffeoylquinic acids, and dicaffeoylquinic acids can reduce surface tension of the steviol glycoside composition with reduced surface tension. A surface tension reducing compound that is enriched for dicaffeoylquinic acids can comprise 10% or more, 15% or more, 20% or more, 25% or more, 30% or more, 35% or more, 40% or more, 45% or more, or 50% or more, 60% or more, 70% or more, or 80% or more, or 90% or more dicaffeoylquinic acids. In other aspects, a surface tension reducing compound that is enriched for dicaffeoylquinic acids can comprise 10% or more, 15% or more, 20% or more, 25% or more, 30% or more, 35% or more, 40% or more, 45% or more, or 50% or more, 60% or more, 70% or more, or 80% or more, or 90% or more of a combination of one or more of 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, and 4,5-dicaffeoylquinic acid, and salts thereof.

The amount of an individual surface tension reducing compound species in the admixture can vary. For example, dicaffeoylquinic acid can be present in the admixture at a concentration from about 1 ppm to about 1000 ppm, from about 1 ppm to about 10000 ppm, from about 1 ppm to about 100000 ppm, from about 1 ppm to about 200000 ppm, or from about 1 ppm to about 300000 ppm. In some aspects, dicaffeoylquinic acid can be present in the admixture at a concentration from about 100 ppm to about 5000 ppm, about 200 ppm to about 5000 ppm, 300 ppm to about 5000 ppm, 400 ppm to about 5000 ppm, 500 ppm to about 5000 ppm, 600 ppm to about 5000 ppm, 700 ppm to about 5000 ppm, 800 ppm to about 5000 ppm, 900 ppm to about 5000 ppm, or 1000 ppm to about 5000 ppm. In some aspects, dicaffeoylquinic acid can be present in the admixture at a concentration from about 1000 ppm to about 5000 ppm, about 2000 ppm to about 5000 ppm, about 3000 ppm to about 5000 ppm, or about 4000 ppm to about 5000 ppm. In some aspects, dicaffeoylquinic acid can be present in the admixture at a concentration of or greater than about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, or 100000 ppm. In some aspects, dicaffeoylquinic acid can be present in the admixture at a concentration of or greater than about 200000 ppm. In some aspects, dicaffeoylquinic acid can be present in the admixture at a concentration of or greater than about 300000 ppm. Unless otherwise expressly stated, ppm is on a by weight basis.

The amount of an individual surface tension reducing compound species in the dry admixture can vary. For example, an individual steviol glycoside species can be present in the dry admixture at a concentration of about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, or more.

In some aspects, the dry admixture comprises surface tension reducing compound at 1%, 2%, 3%, 4%, 5%, 6%, 7%, 8%, 9%, 10% or more by weight. The dry admixture can comprise surface tension reducing compound at 11%, 12%, 13%, 14%, 15%, 16%, 17%, 18%, 19%, 20% or more by weight. The dry mixture can comprise surface tension reducing compound at 21%, 22%, 23%, 24%, 25%, 26%, 27%, 28%, 29%, 30% or more by weight. The dry mixture can comprise surface tension reducing compound at 35%, 40%, 45%, 50%, 55%, 60%, 65%, 70%, 75%, 80%, 85%, 90% or more by weight.

In some aspects, the ratio of surface tension reducing compound to steviol glycoside in the dry admixture can vary. The ratio of surface tension reducing compound to steviol glycoside in the dry admixture can be in any amount effective to reduce surface tension. For example, the ratio of surface tension reducing compound to steviol glycoside can be from about 0.1:1 to 10:1. In some aspects, the ratio of surface tension reducing compound to steviol glycoside can be in the range of about 0.1:1 to 5:1, about 0.5:1 to 4:1, or about 1:1 to 3:1. In other aspects, the ratio of surface tension reducing compound to steviol glycoside is about 1:1, 2:1, 3:1, 4:1, 5:1, 6:1, 7:1, 8:1, 9:1, or 10:1. In other aspects, the ratio of surface tension reducing compound to steviol glycoside is about 0.1:1, 0.2:1, 0.3:1, 0.4:1, 0.5:1, 0.6:1, 0.7:1, 0.8:1 or 0.9:1. In other aspects, the ratio of surface tension reducing compound to steviol glycoside is about 1.1:1, 1.2:1, 1.3:1, 1.4:1, 1.5:1, 1.6:1, 1.7:1, 1.8:1, or 1.9:1. In other aspects, the ratio of surface tension reducing compound to steviol glycoside is about 2.1:1, 2.2:1, 2.3:1, 2.4:1, 2.5:1, 2.6:1, 2.7:1, 2.8:1, or 2.9:1. In other aspects, the ratio of surface tension reducing compound to steviol glycoside is about 3.1:1, 3.2:1, 3.3:1, 3.4:1, 3.5:1, 3.6:1, 3.7:1, 3.8:1, or 3.9:1. In other aspects, the ratio of surface tension reducing compound to steviol glycoside is about 4.1:1, 4.2:1, 4.3:1, 4.4:1, 4.5:1, 4.6:1, 4.7:1, 4.8:1, or 4.9:1.

In some aspects, the dry admixture can comprise additives, flavors, colors, fillers, bulking agents, and other additives including, but not limited to those described above. In other aspects, the one or more additives is present in the dry admixture at about 0.1 ppm to about 4,000 ppm. In some aspects, the one or more additives is present in the dry admixture at about 0.1% to about 99% by weight.

In some aspects, the present disclosure is drawn to methods for reducing surface tension in a steviol glycoside solution. For example, a method for reducing surface tension in a steviol glycoside solution can comprise preparing any of the steviol glycoside composition with reduced surface tensions described above. A method for reducing surface tension in a steviol glycoside solution can comprise contacting a steviol glycoside composition and an surface tension reducing compound with an aqueous solution to prepare any of the steviol glycoside composition with reduced surface tensions described above, In other aspects, a method for reducing surface tension in a steviol glycoside solution can comprise contacting a steviol glycoside solution and surface tension reducing solution to prepare one of the steviol glycoside composition with reduced surface tensions described above. In some aspects, a method for reducing surface tension in a steviol glycoside solution can comprise contacting a steviol glycoside solution with dry surface tension reducing compound to prepare one of the steviol glycoside composition with reduced surface tensions described above. Additionally, a method for reducing surface tension in a steviol glycoside solution can comprise contacting a dry steviol glycoside with an surface tension reducing solution to prepare one of the steviol glycoside composition with reduced surface tensions described above. Also, a method for reducing surface tension in a steviol glycoside solution can comprise preparing any of the admixtures of steviol glycoside and surface tension reducing compound as described above and then preparing an aqueous solution using the admixture as described above.

In some aspects, a method for reducing surface tension in a steviol glycoside solution can reduce surface tension by at least 10%, at least 20%, at least 30%, at least 40%, at least 50%, at least 60%, at least 70%, at least 80% or at least 90% compared to a steviol glycoside solution without an surface tension reducing compound. In some aspects, a method for reducing surface tension in a steviol glycoside solution can reduce surface tension by at least 1%, 2%, 3%, 4%, 5%, 6%, 7%, 8%, 9%, 10%, 11%, 12%, 13%, 14%, 15%, 16%, 17%, 18%, 19% or 20% compared to a steviol glycoside solution without an surface tension reducing compound. In other aspects, a method for reducing surface tension in a steviol glycoside solution can reduce initial surface tension by at least 10%, at least 20%, at least 30%, at least 40%, at least 50%, at least 60%, at least 70%, at least 80% or at least 90% compared to a steviol glycoside solution without an surface tension reducing compound. In some aspects, a method for reducing surface tension in a steviol glycoside solution can reduce surface tension over time by at least 10%, at least 20%, at least 30%, at least 40%, at least 50%, at least 60%, at least 70%, at least 80% or at least 90% compared to a steviol glycoside solution without an surface tension reducing compound. In some aspects, a method for reducing surface tension in a steviol glycoside solution can reduce surface tension at equilibrium by at least 10%, at least 20%, at least 30%, at least 40%, at least 50%, at least 60%, at least 70%, at least 80% or at least 90% compared to a steviol glycoside solution without an surface tension reducing compound.

In some aspects, the present disclosure is drawn to methods for reducing surface tension in a steviol glycoside solution. For example, a method for reducing surface tension in a steviol glycoside solution can comprise preparing any of the steviol glycoside composition with reduced surface tensions described above. A method for reducing surface tension in a steviol glycoside solution can comprise contacting a steviol glycoside composition and an surface tension reducing compound with an aqueous solution to prepare any of the steviol glycoside composition with reduced surface tensions described above, In other aspects, a method for reducing surface tension in a steviol glycoside solution can comprise contacting a steviol glycoside solution and a surface tension reducing solution to prepare one of the steviol glycoside composition with reduced surface tensions described above. In some aspects, a method for reducing surface tension in a steviol glycoside solution can comprise contacting a steviol glycoside solution with dry surface tension reducing compound to prepare one of the steviol glycoside composition with reduced surface tensions described above. Additionally, a method for reducing surface tension in a steviol glycoside solution can comprise contacting a dry steviol glycoside with a surface tension reducing solution to prepare one of the steviol glycoside composition with reduced surface tensions described above. Also, a method for reducing surface tension in a steviol glycoside solution can comprise preparing any of the admixtures of steviol glycoside and surface tension reducing compound as described above and then preparing an aqueous solution using the admixture as described above.

In some aspects, a method for reducing surface tension in a steviol glycoside solution can reduce surface tension by at least 10%, at least 20%, at least 30%, at least 40%, at least 50%, at least 60%, at least 70%, at least 80% or at least 90% compared to a steviol glycoside solution without an surface tension reducing compound.

As used herein, the singular forms "a," "an," and "the" include plural referents unless the context clearly dictates otherwise. For example, reference to "a steviol glycoside" means one or more steviol glycosides.

EXAMPLES

The following examples are provided to illustrate the disclosure, but are not intended to limit the scope thereof. All parts and percentages are by weight unless otherwise indicated.

Example 1

A series of surface tension assays were carried out to characterize steviol glycoside compositions with and without surface tension reducing compound. A steviol glycoside blend comprising primarily rebaudioside M (RM80) was used. A surface tension reducing compound was prepared from yerba mate. The yerba mate surface tension reducing compound comprised about 50% dicaffeoylquinic acids. Chlorogenic acid was obtained commercially and comprised primarily monocaffeoylquinic acids.

A control solution of 1000 ppm of the RM80 was prepared and labelled as "A". A control solution of 1000 ppm of the yerba mate surface tension reducing compound was prepared and labelled as "B". A test solution of 1000 ppm of RM80 blend and 1000 ppm of yerba mate surface tension reducing compound was prepared and labelled as "C". A test solution of 1000 ppm of RM80 and 3000 ppm of chlorogenic acid was prepared and labelled as "D". Each solution was also observed visually for foaming. The control solution of 1000 ppm of the yerba mate surface tension reducing compound produced no foam. The test solution of 1000 ppm of RM80 and 1000 ppm of yerba mate surface tension reducing compound produced foam with smaller bubbles than the test solution of 1000 ppm of RM80 and 3000 ppm of chlorogenic acid.

Surface tension measurements of each of the control solutions and test solutions were determined by a Kruss K100MK2 Tensiometer with a roughened platinum and iridium Wilhelmy plate in a 45 mm diameter glass vessel at 20° C. The surface tension of the control solution of 1000 ppm of the RM80 ("A") was 63.51 mN/m (n=2). The surface tension of the control solution of 1000 ppm of the yerba mate surface tension reducing compound ("B") was 50.45 mN/m (n=3). The surface tension of the test solution of 1000 ppm of RM80 and 1000 ppm of yerba mate surface tension reducing compound ("C") was 55.66 mN/m (n=2). The surface tension of the test solution of 1000 ppm of RM80 and 3000 ppm of chlorogenic acid ("D") was 63.68 mN/m (n=2). The surface tension measurements are shown below in Table 1 and in FIG. 1.

TABLE 1

| Sample | RebD/RebM | Surface tension reducing compound | Surface tension (mN/m at 20° at equilibrium) |
|---|---|---|---|
| A | 1000 ppm | — | 63.51 |
| B | — | 1000 ppm of yerba mate surface tension reducing compound | 50.45 |
| C | 1000 ppm | 1000 ppm of yerba mate surface tension reducing compound | 55.66 |
| D | 1000 ppm | 3000 ppm of commercially prepared chlorogenic acid | 63.68 |

The surface tension of the control solution of yerba mate surface tension reducing compound was lower than the surface tension of the control solution of RM80. The surface tension of the test solution of RM80 and yerba mate surface tension reducing compound was lower than the surface tension of the control solution of RM80. The surface tension of the test solution of RM80 and chlorogenic acid was similar to the control solution of RM80. The surface tension assays showed that the yerba mate surface tension reducing compound lowered the surface tension of the RM80 solution. The surface tension assays also showed that the chlorogenic acid likely did not affect the surface tension of the RM80 solution. The surface tension assays showed that the yerba mate surface tension reducing compound, which contained the higher ratio of dicaffeoylquinic acids (~50%), was more effective in reducing the surface tension of the steviol glycoside solution than the chlorogenic acid which comprised primarily monocaffeoylquinic acids.

Figure 2A:
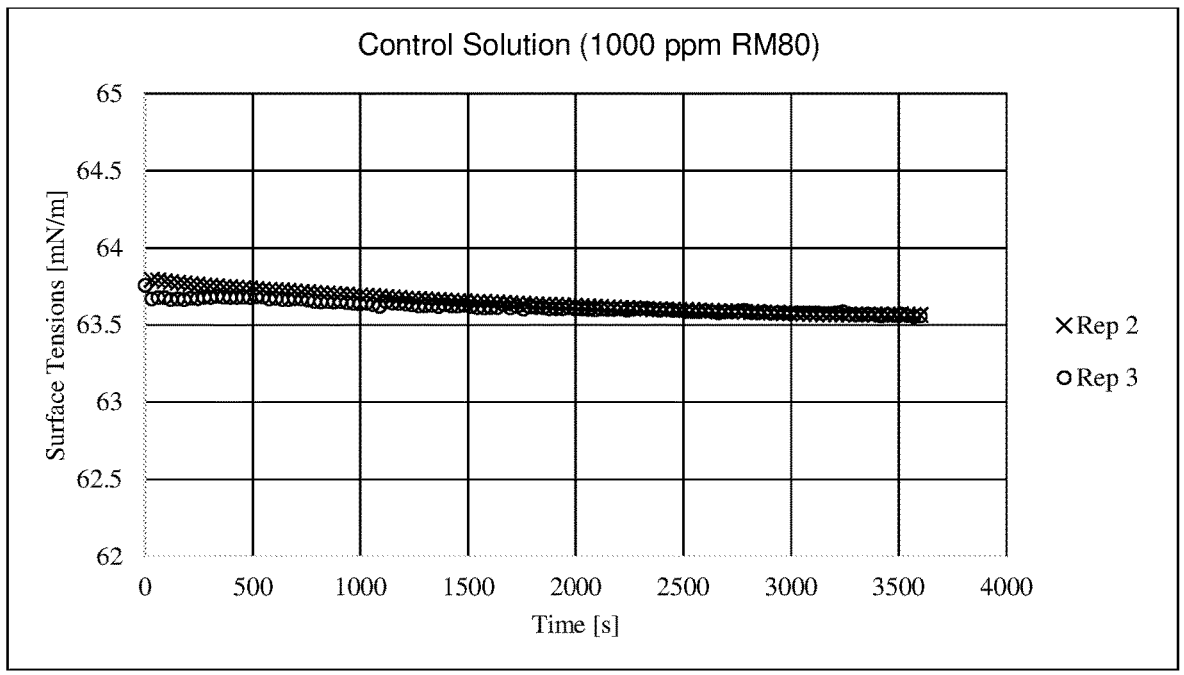
FIG. 2A shows a kinetic surface plot of surface tension over time for a control solution of a steviol glycoside blend(RM80).
Figure 2B:
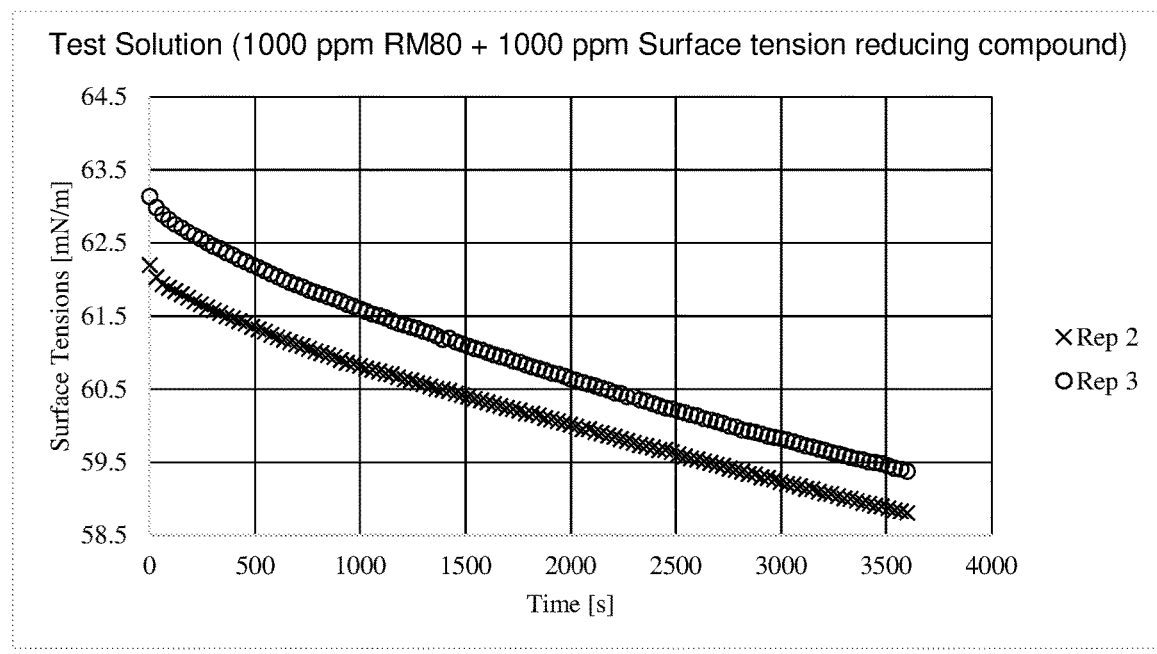
FIG. 2B shows a kinetic surface plot of surface tension over time for a test solution of a steviol glycoside blend (RM80) and a surface tension reducing compound(isolated from yerba mate).

Kinetic surface plots of surface tension over time were also recorded for the control solution of 1000 ppm of the RM80 and the test solution of 1000 ppm of RM80 and 1000 ppm of yerba mate surface tension reducing compound. FIG. 2A shows the kinetic surface plot of surface tension over time for the control solution of 1000 ppm of the RM80 ("A"). FIG. 2B shows the kinetic surface plot of surface tension over time for the test solution of 1000 ppm of RM80 and 1000 ppm of yerba mate surface tension reducing compound ("C"). The test solution of 1000 ppm of RM80 and 1000 ppm of yerba mate surface tension reducing compound showed significant reduction of surface tension over time indicating active diffusion from the bulk solution to the interface layer. The control solution of 1000 ppm of the RM80 exhibited small dynamic ranges (e.g. <1 mN/m).

Example 2

A series of surface tension assays were carried out to characterize steviol glycoside composition with and without surface tension reducing compounds. Highly purified rebaudioside A (~95%), rebaudioside D (>99%), rebaudioside M (>99%) were assayed. Rebaudioside A blend derived from *Stevia* leaf at ≥80% rebaudioside A (RA80) was also used. A surface tension reducing compound was prepared from yerba mate. The yerba mate surface tension reducing compound comprised about 50% dicaffeoylquinic acids.

Control and test solutions were prepared by adding 200 mg of the respective steviol glycoside and/or 200 mg of the surface tension reducing compound to each individual container and then adding 400 ml of ultrapure (18.2 MΩ) water. The individual containers were sealed and shaken to mix. The solutions containing only Reb D or only Reb M were heated to 40-50° C. to fully solubilize the steviol glycoside. The individual containers were allowed to equilibrate at room temperature and then stored at room temperature until assayed. The respective makeup of each solution is shown in Table 2.

TABLE 2

| Sample | Steviol glycoside | Surface tension reducing compound (prepared from yerba mate with ~50% dicaffeoylquinic acids) |
|---|---|---|
| 1 | 500 ppm RebA (~95%) | — |
| 2 | 500 ppm RebA (~95%) | 500 ppm |
| 3 | 500 ppm RebD (>99%) | — |
| 4 | 500 ppm RebD (>99%) | 500 ppm |
| 5 | 500 ppm RebM (>99%) | — |
| 6 | 500 ppm RebM (>99%) | 500 ppm |
| 7 | 500 ppm RA80 | — |
| 8 | 500 ppm RA80 | 500 ppm |
| 9 | — | — |
| 10 | — | 500 ppm |

Figure 3:
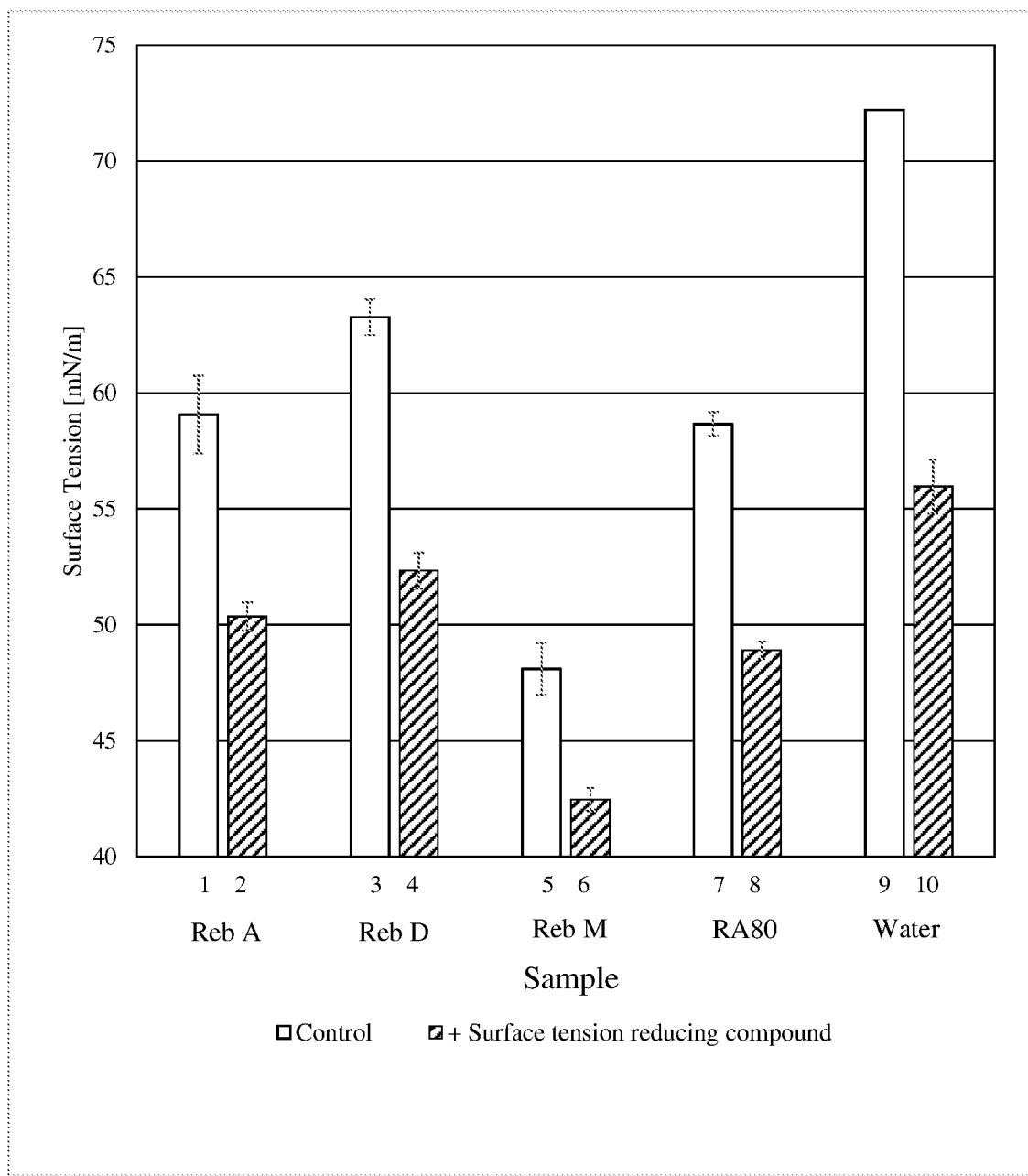
FIG. 3 shows surface tension measurements for solutions of rebaudioside A, rebaudioside D, rebaudioside M, and a blend of rebaudioside A (RA80) with and without surface tension reducing compound(isolated from yerba mate).

Surface tension measurements of each solution were determined by a Kruss K100MK2 Tensiometer with a roughened platinum and iridium Wilhelmy plate (19.9 mm width× 0.2 mm thickness×10 mm height) in a 45 mm diameter glass vessel at 20° C. The settings were as follows: detection speed, 10 mm/min; detection sensitivity, 0.005 g; immersion depth 2.0 mm, values, 10 (per log10 time decade); acquisition, logarithmic; maximum measuring time 21600 s; and vessel, SV10 glass vessel, 43.5 ml, 50 mm. The probe was cleaned with water and flame dried after each measurement. The glass vessel was cleaned thoroughly with water between samples. Deionized water was used as a reference between samples to ensure that no cross-contamination between plate and vessel occurred. Sample containers were gently inverted multiple times to promote thorough mixing. For each sample measurement, 40-50 ml of each sample was transferred to the glass vessel and immediately placed onto the sample stage. Each sample aliquot was magnetically stirred until the surface tension measurement was initiated to prevent surface aging. Samples were measured at equilibrium at 6 h and comprised an average of three data points across all replicates excluding outliers. The surface tension measurements are shown below in Table 3 and in FIG. 3.

TABLE 3

| Sample | Steviol glycoside | Surface tension reducing compound (prepared from yerba mate with ~50% dicaffeoylquinic acids) | Average surface tension measurement (mN/m at 20° at equilibrium) | Standard deviation | Reduction in surface tension |
|---|---|---|---|---|---|
| 1 | 500 ppm RebA (~95%) | — | 59.06623 | 1.67811 | |

TABLE 3-continued

| Sample | Steviol glycoside | Surface tension reducing compound (prepared from yerba mate with ~50% dicaffeoylquinic acids) | Average surface tension measurement (mN/m at 20° at equilibrium) | Standard deviation | Reduction in surface tension |
|---|---|---|---|---|---|
| 2 | 500 ppm RebA (~95%) | 500 ppm | 50.35869 | 1.198573 | 14.74% |
| 3 | 500 ppm RebD (>99%) | — | 63.2594 | 0.765295 | |
| 4 | 500 ppm RebD (>99%) | 500 ppm | 52.33913 | 0.773653 | 17.26% |
| 5 | 500 ppm RebM (>99%) | — | 48.09162 | 1.112912 | |
| 6 | 500 ppm RebM (>99%) | 500 ppm | 42.46702 | 0.498555 | 11.70% |
| 7 | 500 ppm RA80 | — | 58.65504 | 0.519567 | |
| 8 | 500 ppm RA80 | 500 ppm | 48.90965 | 0.380981 | 16.61% |
| 9 | — | — | 72.2 | | |
| 10 | — | 500 ppm | 55.96052 | 1.15176 | 22.49% |

The surface tension measurements showed that the surface tension was reduced for the rebaudioside A with surface tension reducing compound (Sample 2) compared to the rebaudioside A without surface tension reducing compound (Sample 1). The surface tension was reduced by about 14.74%. The surface tension measurements showed that the surface tension was reduced for the rebaudioside D with surface tension reducing compound (Sample 4) compared to the rebaudioside D without surface tension reducing compound (Sample 3). The surface tension was reduced by about 17.26%. The surface tension measurements showed that the surface tension was reduced for the rebaudioside M with surface tension reducing compound (Sample 6) compared to the rebaudioside M without surface tension reducing compound (Sample 5). The surface tension was reduced by about 11.70%. The surface tension measurements showed that the surface tension was reduced for RA80 with surface tension reducing compound (Sample 8) compared to RA80 without surface tension reducing compound (Sample 7). The surface tension was reduced by about 16.61%. The surface tension measurements showed that the surface tension was reduced for water with surface tension reducing compound (Sample 10) compared to water without surface tension reducing compound (Sample 9). The surface tension was reduced by about 22.49%. The surface tension measurements showed that the surface tension reducing compound reduced surface tension for each of the tested steviol glycoside systems.

Example 3

A series of surface tension assays were carried out to characterize steviol glycoside composition with and without different surface tension reducing compounds. A steviol glycoside blend comprising primarily rebaudioside M (RM80) was used. Cichoric acid and rosmarinic acid were used as surface tension reducing compounds.

A control solution of water was prepared. A control solution of 500 ppm of cichoric acid surface tension reducing compound was prepared. A test solution of 500 ppm of RM80 blend and 500 ppm of cichoric acid surface tension reducing compound was prepared. A control solution of 500 ppm of rosmarinic acid surface tension reducing compound was prepared. A test solution of 500 ppm of RM80 and 500 ppm of rosmarinic acid surface tension reducing compound was prepared.

Surface tension measurements of each of the control solutions and test solutions were determined by a Kruss K100MK2 Tensiometer with a roughened platinum and iridium Wilhelmy plate in a 45 mm diameter glass vessel at 20° C. as described above. The surface tension of the control solution of water was 72.2 mN/m. The surface tension of the solution of 500 ppm of cichoric acid surface tension reducing compound was 71.67 mN/m. The surface tension of the test solution of 500 ppm of RM80 blend and 500 ppm of cichoric acid surface tension reducing compound was 45.46 mN/m. The surface tension of the control solution of 500 ppm of rosmarinic acid surface tension reducing compound was 63.08 mN/m. The surface tension of the test solution of 500 ppm of RM80 and 500 ppm of rosmarinic acid surface tension reducing compound was 45.6 nM/m.

Figure 4:
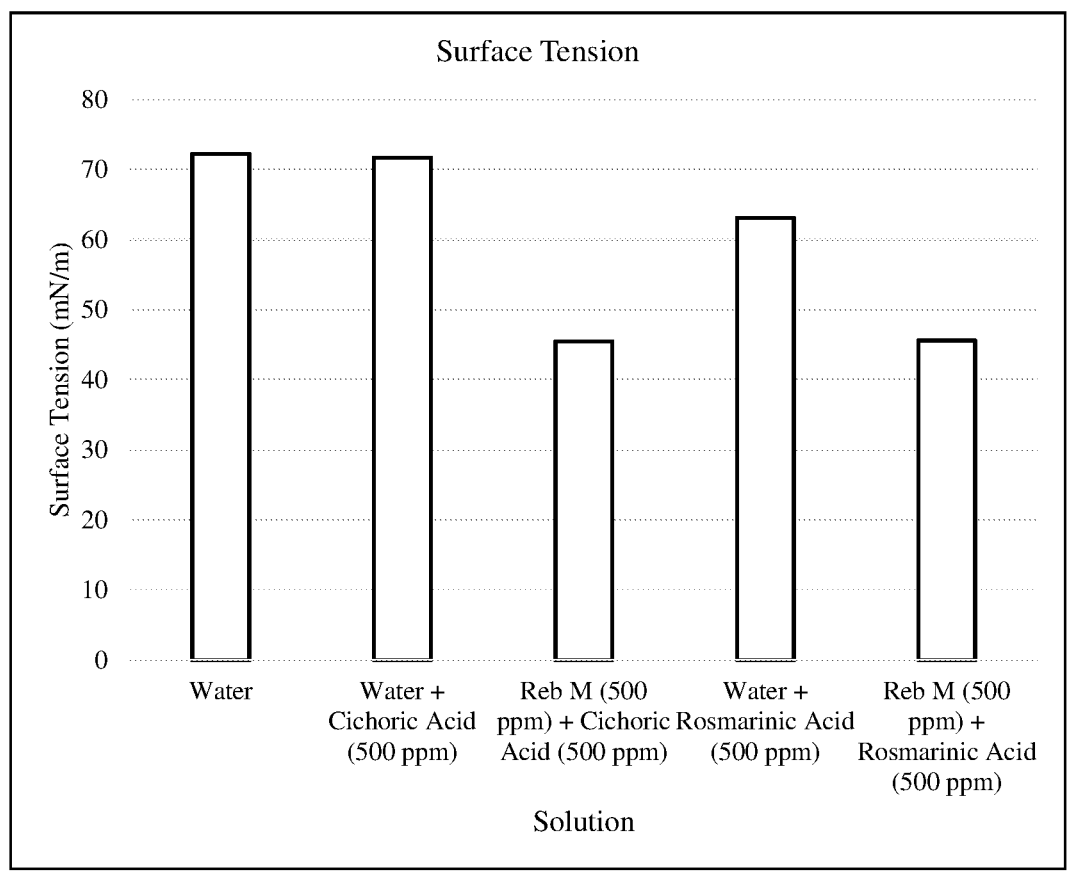
FIG. 4 shows surface tension measurements for solutions of rebaudioside M (RM80) with and without surface tension reducing compound (rosmarinic acid or cichoric acid).

The surface tension measurements are shown below in Table 4 and in FIG. 4.

TABLE 4

| Sample | Steviol glycoside | Surface tension reducing compound | Average surface tension (mN/m at 20° at equilibrium) |
|---|---|---|---|
| Water | — | — | 72.2 |
| Cichoric Acid | — | 500 ppm of cichoric acid | 71.67 |
| RM80 + cichoric acid | 500 ppm of RM80 | 500 ppm of cichoric acid | 45.46 |
| Rosmarinic acid | — | 500 ppm of rosmarinic acid | 63.08 |
| RM80 + rosmarinic acid | 500 ppm of RM80 | 500 ppm of rosmarinic acid | 45.6 |

The surface tension of the control cichoric acid surface tension reducing compound was about the same as the water control, showing that the cichoric acid surface tension reducing compound did not significantly reduce the surface tension. The surface tension of the test solution of 500 ppm of RM80 blend and 500 ppm of cichoric acid surface tension reducing compound was reduced (45.46 mN/m) from the water control (72.2 mN/m) and the control cichoric acid surface tension reducing compound (45.46 mN/m), showing that the test solution had a reduced surface tension compared to the control solutions. The surface tension of the control rosmarinic acid surface tension reducing compound (63.08 mN/m) was reduced compared to the water control (72.2 mN/m), showing that the rosmarinic acid surface tension reducing compound did reduce the surface tension. The surface tension of the test solution of 500 ppm of RM80 blend and 500 ppm of rosmarinic acid surface tension reducing compound was reduced (45.6 mN/m) from the water control (72.2 mN/m) and the control rosmarinic acid surface tension reducing compound (63.08 mN/m), showing that the test solution had a reduced surface tension compared to the control solutions.

Figure 5:
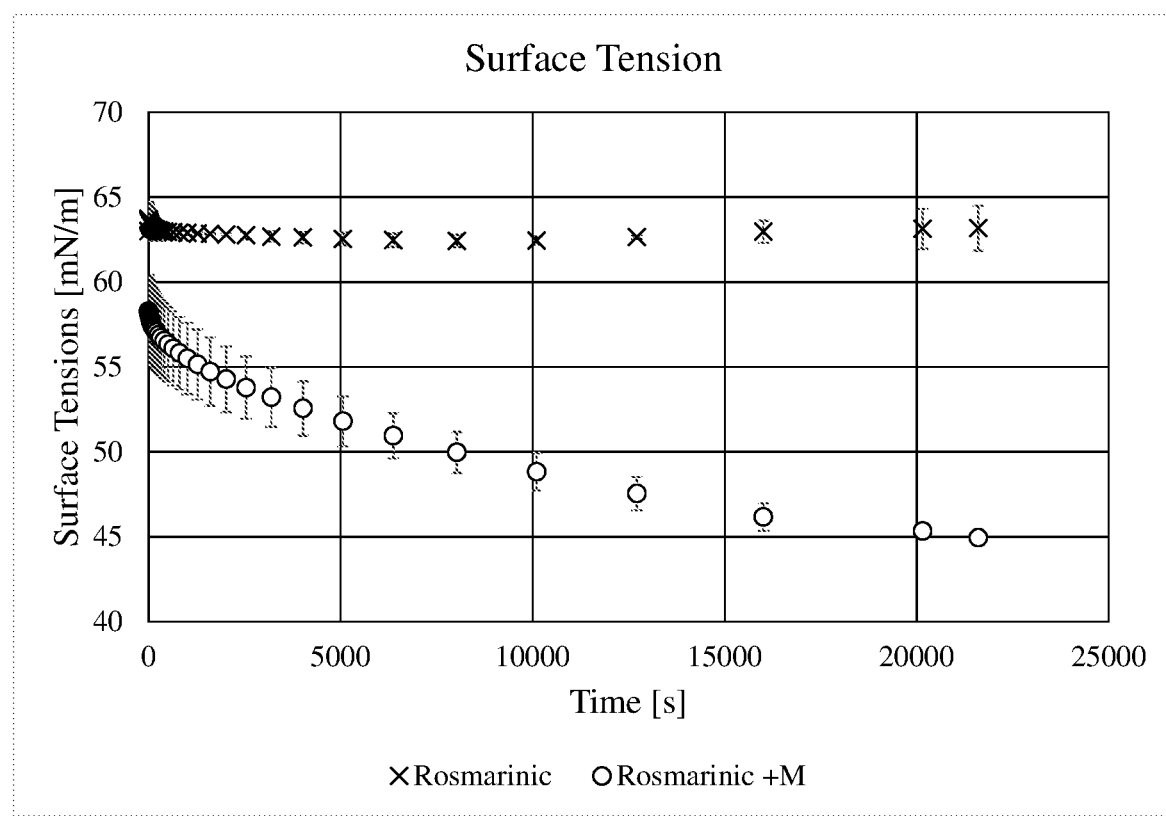
FIG. 5 shows a kinetic surface plot of surface tension over time for a control solution of rosmarinic acid and a test solution of steviol glycoside(RM80) and rosmarinic acid.
Figure 6:
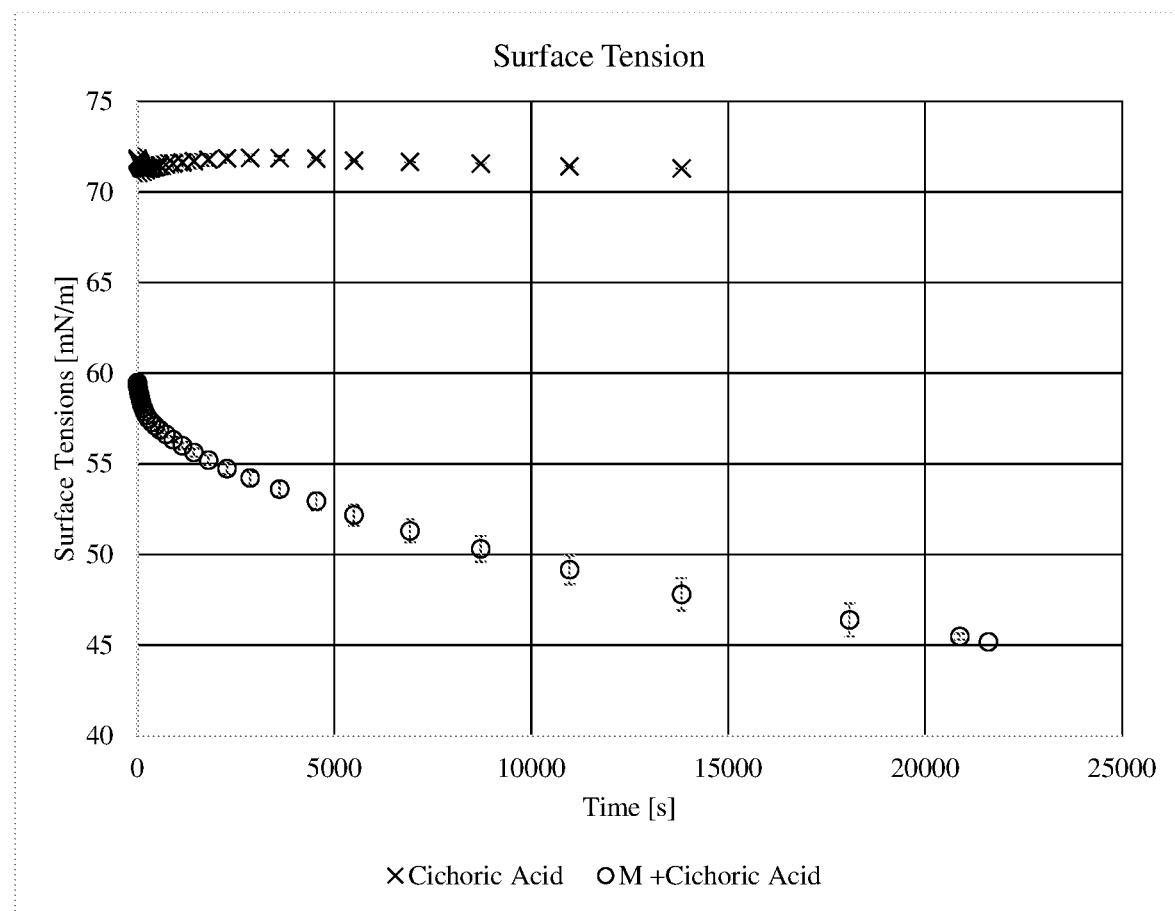
FIG. 6 shows a kinetic surface plot of surface tension over time for a control solution of cichoric acid and a test solution of steviol glycoside(RM80) and cichoric acid.

Kinetic surface plots of surface tension over time were also recorded for the control solution of 500 ppm of the rosmarinic acid surface tension reducing compound and the test solution of 500 ppm of RM80 and 500 ppm of rosmarinic surface tension reducing compound. FIG. 5 shows the kinetic surface plot of surface tension over time for the control solution of 500 ppm of the rosmarinic acid and the test solution of 500 ppm of RM80 and 500 ppm of rosmarinic surface tension reducing compound. FIG. 6 shows the kinetic surface plot of surface tension over time for the control solution of 500 ppm of the cichoric acid and the test solution of 500 ppm of RM80 and 500 ppm of cichoric acid surface tension reducing compound.

The invention claimed is:

1. A method for reducing surface tension in a steviol glycoside solution, the method comprising:
   adding one or more steviol glycosides and a surface tension reducing compound to an aqueous solution to form a steviol glycoside solution; wherein surface tension of the steviol glycoside solution is reduced relative to an equivalent solution lacking the surface tension reducing compound;
   wherein the surface tension reducing compound comprises:
   (i) one or more monocaffeoylquinic acids or salts thereof;
   (ii) at least 20% (wt) of one or more dicaffeoylquinic acids or salts thereof; and
   (iii) at least one of an ester of ferulic acid and quinic acid, an ester of sinapic acid and quinic acid, an ester of p-coumaric acid and quinic acid, an ester of caffeic acid and 3-(3,4-dihydroxyphenyl)lactic acid, an ester of caffeic acid and tartaric acid, and isomers thereof; and
   wherein the one or more steviol glycosides and the surface tension reducing compound are added such that the steviol glycoside solution comprises a 1:0.5 to 1:4 ratio by weight of steviol glycose to surface tension reducing compound.

2. The method of claim 1, wherein surface tension is reduced by at least 10%, at least 20%, at least 30%, at least 40%, at least 50%, at least 60%, at least 70%, at least 80% or at least 90% compared to a steviol glycoside solution without the surface tension reducing compound.

3. The method of claim 1, wherein the surface tension reducing compound comprises at least 30% (wt) of a total of 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, 4,5-dicaffeoylquinic acid, and salts thereof.

4. The method of claim 1, wherein the one or more monocaffeoylquinic acids or salts thereof comprise one or more of neochlorogenic acid, cryptochlorogenic acid, 1,3-dicaffeoylquinic acid, and salts thereof.

5. The method of claim 1, wherein the surface tension reducing compound comprises one or more of 3-O-feruloylquinic acid, 4-O-feruloylquinic acid, 5-O-feruloylquinic acid, 3,4-diferuloylquinic acid, 3,5-diferuloylquinic acid, 4,5-diferuloylquinic acid, and salts thereof.

6. The method of claim 1, wherein the steviol glycoside solution comprises between about 100 ppm and about 5000 ppm steviol glycoside.

7. The method of claim 1, wherein the one or more steviol glycosides comprises rebaudioside D, rebaudioside M, or combination thereof.

8. The method of claim 1, wherein the steviol glycoside solution comprises between 50 wt % and 95 wt % rebaudioside M based on total weight of steviol glycosides in the solution.

9. The method of claim 1, wherein the steviol glycoside solution comprises between 5 wt % and 25 wt % rebaudioside D based on total weight of steviol glycosides in the solution.

10. The method of claim 1, wherein the steviol glycoside solution comprises at least 1 wt % steviol glycosides.

11. The method of claim 1, wherein the steviol glycoside solution comprises a 1:1 to 1:3 ration by weight of steviol glycoside to surface tension reducing compound.

12. The method of claim 1, wherein the aqueous solution comprises a 1:1 to 1:3 ratio by weight of steviol glycoside to total concentration of esters of caffeic acid and quinic acid, esters of ferulic acid and quinic acid, esters of sinapic acid and quinic acid, esters of p-coumaric acid and quinic acid, esters of caffeic acid and 3-(3,4-dihydroxyphenyl) lactic acid, and esters of caffeic acid and tartaric acid.

13. The method of claim 1, additionally comprising the step of preparing a beverage comprising the steviol glycoside solution.

14. A method for preparing a beverage concentrate solution with reduced surface tension, the method comprising:
   adding to an aqueous solution i) one or more steviol glycosides and ii) a surface tension reducing compound to form a beverage concentrate solution, wherein the beverage concentrate solution has reduced surface tension relative to an equivalent beverage concentrate solution lacking the surface tension reducing compound;
   wherein the surface tension reducing compound comprises:
   (i) one or more monocaffeoylquinic acids or salts thereof;
   (ii) at least 20% (wt) of one or more dicaffeoylquinic acids or salts thereof, and
   (iii) at least one of an ester of ferulic acid and quinic acid, an ester of sinapic acid and quinic acid, an ester of p-coumaric acid and quinic acid, an ester of caffeic acid and 3-(3,4-dihydroxyphenyl)lactic acid, an ester of caffeic acid and tartaric acid, and isomers thereof; and
   wherein the one or more steviol glycosides and the surface tension reducing compound are added such that the beverage concentrate solution comprises a 1:0.5 to 1:4 ratio by weight of steviol glycose to surface tension reducing compound.

15. The method of claim 14, wherein the beverage concentrate solution comprises 2400 to 4200 ppm of total steviol glycoside.

16. The method of claim 14, wherein the beverage concentrate solution comprises 1800 to 5400 ppm surface tension reducing compound.

17. The method of claim 14, wherein the beverage concentrate solution includes a buffer and has a pH between 1.5 and 4.

18. The method of claim 14, wherein surface tension is reduced by at least 10%, at least 20%, at least 30%, at least 40%, at least 50%, at least 60%, at least 70%, at least 80% or at least 90% compared to a steviol glycoside solution without the surface tension reducing compound.

19. The method of claim 14, wherein the surface tension reducing compound comprises at least 30% (wt) of a total of 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, 4,5-dicaffeoylquinic acid, and salts thereof.

20. The method of claim 14, wherein the one or more steviol glycosides comprises rebaudioside D, rebaudioside M, or combination thereof.

21. The method of claim 14, wherein the steviol glycoside solution comprises between 50 wt % and 95 wt % rebaudioside M and 5 wt % and 25 wt % rebaudioside D based on total weight of steviol glycosides in the solution.

22. The method of claim 14, wherein the steviol glycoside solution comprises at least 1 wt % steviol glycosides.

23. The method of claim 14, wherein the aqueous solution comprises a 1:1 to 1:3 ratio by weight of steviol glycoside to total concentration of esters of caffeic acid and quinic acid, esters of ferulic acid and quinic acid, esters of sinapic acid and quinic acid, esters of p-coumaric acid and quinic acid, esters of caffeic acid and 3-(3,4-dihydroxyphenyl) lactic acid, and esters of caffeic acid and tartaric acid.

* * * * *

UNITED STATES PATENT AND TRADEMARK OFFICE
CERTIFICATE OF CORRECTION

PATENT NO. : 12,097,231 B2
APPLICATION NO. : 18/328066
DATED : September 24, 2024
INVENTOR(S) : Dan S. Gaspard et al.

It is certified that error appears in the above-identified patent and that said Letters Patent is hereby corrected as shown below:

On the Title Page

In Column 1, page 3, Item (56) Line 5 delete "1250399" and insert -- 1250399 C --, therefor.
In Column 2, page 3, Item (56) Line 69 delete "W" and insert -- A1 --, therefor.
In Column 2, page 3, Item (56) Line 75 delete "W" and insert -- A1 --, therefor.
In Column 1, page 4, Item (56) Line 8 delete "WO 11094423 W 8/2011". Duplicate Entry.
In Column 1, page 4, Item (56) Line 17 delete "W" and insert -- A1 --, therefor.
In Column 1, page 4, Item (56) Line 28 delete "W" and insert -- A1 --, therefor.
In Column 1, page 4, Item (56) Line 29 delete "W" and insert -- A1 --, therefor.
In Column 1, page 4, Item (56) Line 30 delete "W" and insert -- A1 --, therefor.
In Column 1, page 4, Item (56) Line 32 delete "W" and insert -- A1 --, therefor.
In Column 1, page 4, Item (56) Line 35 delete "W" and insert -- A1 --, therefor.
In Column 1, page 4, Item (56) Line 36 delete "W" and insert -- A1 --, therefor.
In Column 1, page 4, Item (56) Line 45 delete "WO 19177634 W 9/2019". Duplicate Entry.
In Column 1, page 4, Item (56) Line 47 delete "W" and insert -- A1 --, therefor.
In Column 1, page 4, Item (56) Line 48 delete "W" and insert -- A1 --, therefor.
In Column 1, page 4, Item (56) Line 49 delete "W" and insert -- A1 --, therefor.
In Column 1, page 4, Item (56) Line 51 delete "W" and insert -- A1 --, therefor.
In Column 1, page 4, Item (56) Line 52 delete "W" and insert -- A1 --, therefor.
In Column 1, page 4, Item (56) Line 53 delete "W" and insert -- A1 --, therefor.
In Column 1, page 4, Item (56) Line 59 delete "W" and insert -- A1 --, therefor.
In Column 2, page 4, Item (56) Line 14 delete "crytalline" and insert -- crystalline --, therefor.
In Column 2, page 4, Item (56) Line 19 delete "coversion" and insert -- conversion --, therefor.
In Column 1, page 5, Item (56) Line 8 delete "al." and insert -- al., --, therefor.
In Column 1, page 5, Item (56) Line 51 delete "al" and insert -- al. --, therefor.
In Column 2, page 5, Item (56) Line 23 delete "Agriculatural" and insert -- Agriculture --, therefor.
In Column 2, page 5, Item (56) Line 41 delete "al" and insert -- al. --, therefor.
In Column 2, page 5, Item (56) Line 42 delete "Ilex" and insert -- {Ilex --, therefor.
In Column 1, page 6, Item (56) Line 9 delete "al," and insert -- al., --, therefor.
In Column 1, page 6, Item (56) Line 16 delete "al," and insert -- al., --, therefor.

Signed and Sealed this
Fourth Day of February, 2025

Coke Morgan Stewart
*Acting Director of the United States Patent and Trademark Office*

CERTIFICATE OF CORRECTION (continued)
U.S. Pat. No. 12,097,231 B2

In Column 1, page 6, Item (56) Line 26 delete "al" and insert -- al. --, therefor.
In Column 2, page 6, Item (56) Line 30 delete "Omamental" and insert -- Ornamental --, therefor.
In Column 2, page 7, Item (56) Line 8 delete "al" and insert -- al. --, therefor.
In Column 2, page 7, Item (56) Line 59 delete "al" and insert -- al. --, therefor.
In Column 2, page 7, Item (56) Line 63 delete "al" and insert -- al. --, therefor.
In Column 2, page 7, Item (56) Line 67 delete "al" and insert -- al. --, therefor.
In Column 2, page 7, Item (56) Line 71 delete "al" and insert -- al. --, therefor.
In Column 1, page 8, Item (56) Line 7 delete "al" and insert -- al. --, therefor.
In Column 1, page 8, Item (56) Line 16 delete "al" and insert -- al. --, therefor.
In Column 1, page 8, Item (56) Line 42 delete "chorogenic" and insert -- chlorogenic --, therefor.
In Column 1, page 8, Item (56) Line 49 delete "Cofffee" and insert -- Coffee --, therefor.
In Column 1, page 8, Item (56) Line 51 delete "al" and insert -- al. --, therefor.
In Column 2, page 8, Item (56) Line 12 delete "al" and insert -- al. --, therefor.
In Column 2, page 8, Item (56) Line 41 delete "al" and insert -- al. --, therefor.

In the Specification

In Column 1, Line 14 delete "May" and insert -- May 25, --, therefor.
In Column 10, Line 17 delete "basis" and insert -- basis. --, therefor.
In Column 11, Line 59 delete "e.g." and insert -- e.g., --, therefor.
In Column 18, Line 22 delete "basis" and insert -- basis. --, therefor.
In Column 25, Line 4 delete "basis" and insert -- basis. --, therefor.
In Column 27, Line 8 delete "basis" and insert -- basis. --, therefor.
In Column 28, Line 29 delete "0.8:1" and insert -- 0.8:1, --, therefor.
In Column 29, Line 50 delete "above," and insert -- above. --, therefor.
In Column 32, Line 8 delete "(18.2 MSΩ)" and insert -- (18.2 MΩ) --, therefor.

In the Claims

In Column 35, Claim 1, Line 24 delete "glycose" and insert -- glycoside --, therefor.
In Column 36, Claim 14, Line 15 delete "thereof," and insert -- thereof; --, therefor.